United States Patent
Shuler et al.

(10) Patent No.: US 8,030,061 B2
(45) Date of Patent: *Oct. 4, 2011

(54) DEVICES AND METHODS FOR PHARMACOKINETIC-BASED CELL CULTURE SYSTEM

(75) Inventors: Michael Shuler, Ithaca, NY (US); Gregory T. Baxter, Salinas, CA (US); Aaron Sin, Ithaca, NY (US); Robert Andrew Harrison, Toronto (CA); Scott Meyers, Norristown, PA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1189 days.

This patent is subject to a terminal disclaimer.

(21) Appl. No.: 11/530,381

(22) Filed: Sep. 8, 2006

(65) Prior Publication Data
US 2007/0020613 A1    Jan. 25, 2007

Related U.S. Application Data

(63) Continuation of application No. 10/133,977, filed on Apr. 25, 2002, now Pat. No. 7,288,405.

(60) Provisional application No. 60/286,493, filed on Apr. 25, 2001.

(51) Int. Cl.
*C12M 3/00* (2006.01)
*C12M 1/34* (2006.01)

(52) U.S. Cl. .......... 435/288.5; 435/373; 435/293.1; 435/294.1

(58) Field of Classification Search .......... 435/373, 435/288.5, 293.1, 294.1
See application file for complete search history.

(56) References Cited

U.S. PATENT DOCUMENTS

| | | | |
|---|---|---|---|
| 3,941,662 A | 3/1976 | Munder et al. |
| 3,948,732 A | 4/1976 | Haddad et al. |
| 4,436,824 A | 3/1984 | Bishop |
| 5,043,260 A | 8/1991 | Jauregui |
| 5,290,684 A | 3/1994 | Kelly |
| 5,486,335 A | 1/1996 | Wilding et al. |
| 5,496,697 A | 3/1996 | Parce et al. |
| 5,498,392 A | 3/1996 | Wilding et al. |
| 5,587,128 A | 12/1996 | Wilding et al. |
| 5,612,188 A | 3/1997 | Shuler et al. |
| 5,637,469 A | 6/1997 | Wilding et al. |
| 5,726,026 A | 3/1998 | Wilding et al. |
| 5,744,366 A | 4/1998 | Kricka et al. |
| 5,820,769 A | 10/1998 | Chou |
| 5,900,160 A | 5/1999 | Whitesides et al. |
| 5,906,828 A | 5/1999 | Cima et al. |

(Continued)

FOREIGN PATENT DOCUMENTS

EP    0539383 B1    9/1996

(Continued)

OTHER PUBLICATIONS

Ausubel, et al. Current Protocols in Molecular Biology. eds. John Wiley & Sons New York NY. 2000 (Table of Contents only).

(Continued)

*Primary Examiner* — William H Beisner
(74) *Attorney, Agent, or Firm* — Wilson Sonsini Goodrich & Rosati

(57) ABSTRACT

Devices, in vitro cell cultures, systems, and methods are provided for microscale cell culture analogous (CCA) device.

65 Claims, 29 Drawing Sheets

U.S. PATENT DOCUMENTS

| | | | |
|---|---|---|---|
| 6,054,277 | A | 4/2000 | Furcht et al. |
| 6,133,030 | A | 10/2000 | Bhatia et al. |
| 6,197,575 | B1 | 3/2001 | Griffith et al. |
| 6,329,195 | B1 | 12/2001 | Pfaller |
| 6,562,616 | B1 | 5/2003 | Toner et al. |
| 6,653,124 | B1 | 11/2003 | Freeman |
| 7,288,405 | B2 * | 10/2007 | Shuler et al. ............... 435/288.5 |
| 2003/0082795 | A1 | 5/2003 | Shuler et al. |
| 2003/0096405 | A1 | 5/2003 | Takayama et al. |
| 2007/0015273 | A1 | 1/2007 | Shuler et al. |
| 2007/0015274 | A1 | 1/2007 | Shuler et al. |
| 2007/0015275 | A1 | 1/2007 | Shuler et al. |
| 2007/0020693 | A1 | 1/2007 | Shuler et al. |
| 2007/0026519 | A1 | 2/2007 | Shuler et al. |
| 2007/0037273 | A1 | 2/2007 | Shuler et al. |
| 2007/0037275 | A1 | 2/2007 | Shuler et al. |
| 2007/0037277 | A1 | 2/2007 | Shuler et al. |
| 2007/0048727 | A1 | 3/2007 | Shuler et al. |
| 2008/0064088 | A1 | 3/2008 | Shuler et al. |
| 2008/0166794 | A1 | 7/2008 | Shuler et al. |
| 2008/0166795 | A1 | 7/2008 | Shuler et al. |

FOREIGN PATENT DOCUMENTS

| | | |
|---|---|---|
| EP | 0637996 B1 | 7/1997 |
| EP | 0823483 A1 | 2/1998 |
| EP | 0637997 B1 | 7/1998 |
| FR | 2786783 A1 | 6/2000 |
| JP | 4-152885 | 5/1992 |
| WO | WO 93/11498 | 6/1993 |
| WO | WO 99/47922 | 9/1999 |

OTHER PUBLICATIONS

Ball, et al. CMATRIX: Software for Physiologically Based Pharmacokinetic Modeling Using a Symbolic Matrix Representation System. Comput. Biol. Med. 1994;24(4):269-276.

Buckpitt, et al. Hepatic and Pulmonary Microsomal Metabolism of Napthalene to Glutathions Adducts: Factors Affecting the Relative Rates of Conjugate Formation. J. Pharmacol. Exp. Ther. 1984; 231(2):291-300.

Cornell Chronicle. Impact of biotechnology examined at symposium. Available at http://www.news.cornell.edu/chronicle/99/9.23.99/biotech_symp.html. Accessed Nov. 7, 2006. (1 page).

Delraso, N.J. In Vitro Methodologies for Enhanced Toxicity Testing. Toxicol. Lett. 1993; 68:91-99.

Funding Proposal No. 96-OLMSA-03-112 to NASA for "Enhancement of cell function in culture by controlled aggregation under microgravity conditions." Approximately 1996.

Funding Proposal No. 9876771 to National Science Foundation for "The nanobiotechnology Center." Approximately 1998.

Funding Proposal to Cornell CAT-biotech grant for "Development of a cell culture analog device for testing chemical toxicity." Approximately 1998.

Funding Proposal to National Science Foundation-NBTC for "Microanalysis of biomolecules." Approximately 2000.

Ghanem, et al. Characterization of a perfusion reactor utilizing mammalian cells on microcarrier beads. Biotechnol Prog. 2000; 16(3):471-9.

Ghanem, et al. Combining cell culture analogue reactor designs and PBPK models to probe mechanisms of naphthalene toxicity. Biotechnol Prog. 2000; 16(3):334-45.

Goodman and Gilman. The Pharmacological Basis of Therapeutics. McGraw-Hill, New York, York, Ninth edition, under sections: Drugs Acting at Synaptic and Neuroeffector Junctional Sites; Drugs Acting on the Central Nervous System; Aytacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppresssion, Drugs Acting on Blood-Forming Organs; Hormones and Hormone Antagonists; Vitamins; Dermatology; Toxicology. 1996.

Haddad, et al. A Methodology for Solving Physiologically Based Pharmacokinetic Models Without the Use of Simulation Software. Toxicol. Lett. 1996; 85(2):113-126.

Haies, et al. Morphometric Study of Rat Lung Cells. Am. Rev. Respir. Dis. 1981; 123:533-541.

Hoang, et al. Physiologically Based Pharmacokinetic Models: Mathematical Fundamentals and Simulation Implementations. Toxicol. Lett. 1995; 79(1-3):99-106.

Hodgson, et al. ADMET-Turning Chemicals into Drugs. Nat. Biotech. 2001; 19:722-726.

Hwang, et al. Ferredoxin Reductase Affect p53-Dependent, 5-Fluorouracil-Induced Apoptosis in Colorectal Cancer Cells. Nat. Med. 2001; 7(10):1111-1117.

Ikeda, et al. Bioactivation of Tegafur to 5-Fluorouracil Is Catalyzed by Cytochrome P-450 2A6 in Human Liver Microsomes in Vitro. Clin. Cancer Res. 2000; 6:4409-4415.

Information related to a presentation for "An 'Animal' on a Chip: Preclinical Evaluation of Pharmaceutical" given at the Biochemical Engineering XI: Molecular Diversity in Bioprocessing Conference on or about Jul. 25, 1999.

Jones, et al. Glowing Jellyfish, Luminescence and a Molecule Called Coelenterazine. Trends Biotechnol. 1999; 17(12):477-481.

Knaak, et al. Development of Partition Coefficients, $V_{max}$ and $K_m$ Values, and Allometric Relationships. Toxicol. Lett. 1995; 79(1-3):87-98.

Koebe, et al. In vitro toxicology in hepatocyte bioreactors-extracellular acidification rate (EAR) in a target cell line indicates hepato-activated transformation of substrates. Toxicology. 2000; 154(1-3):31-44.

Komatsu, et al. Roles of Cytochromes P450 1A2, 2A6, and 2C8 in 5-Fluorouracil Formation from Tegafur, an Anticancer Prodrug, in Human Liver Microsomes. Drug Met. Disp. 2000; 28(12):1457-1463.

Li, et al. Single-Step Procedure for Labeling DNA Strand breaks with Fluorescein- or BODIPY-Conjugated Deoxynucleotides: Detection of Apoptosis and Bromodeoxyuridine Incorporation. Cytometry. 1995; 20:172-180.

Matsuda, et al. Microfabricated Surface Designs for Cell Culture and Diagnosis. ASAIO Journal. 1994; pp. M594-M597.

News From COTABA: 14th Biotechnology Symposium. News From the Cornell Office of Economic Development. Issue 10. Sep. 1999.

Poulin, et al. A Priori Prediction of Tissue: Plasma Partition Coefficients of Drugs to Facilitate the Use of Physiologically-Based Pharmacokinetic Models in Drugs Discovery. J. Pharm. Sci. 2000; 89(1):16-35.

Powers, et al. A microfabricated array bioreactor for perfused 3D liver culture. Biotechnol Bioeng. 2002; 78(3):257-69.

Powers, et al. Functional behavior of primary rat liver cells in a three-dimensional perfused microarray bioreactor. Tissue Eng. 2002; 8(3):499-513.

Rodriguez-Antona, et al. Quantitative RT-PCR Measurement of Human Cytochrome P-450s: Application to Drug Induction Studies. Arch. Biochem. Biophys. 2000; 376(1):109-116.

Schwartz, J. 20 Years Young and Getting Smaller. Cornell Engineering Magazine. vol. 4, No. 3. Published Fall 1998. Available at http://132.236.67.210/engrMagazine/magazine.cfm?issue=FALL1998&page_number=1 §ion=feature4 and http://132.236.67.210/engrMagazine/magazine.cfm?section=feature4&page_number=2 & issue=FALL1998. Accessed Mar. 27, 2007. (Total 5 pages).

Shuler, et al. An "animal" on a chip: Preclinical evaluation of pharmaceuticals. United Engineering Foundation Inc. Jul. 1999.

Shuler, M. L. Presnetated Papers. Available at http://webserver.cheme.cornell.edu/peopleevents/faculty/shuler/presented%20papers.html. Accessed Nov. 13, 2006. (pp. 1-14).

Slob, et al. Structural Identifiability of PBPK Models: Practical Consequences for Modeling Strategies and Study Designs. Crit. Rev. Toxicol. 1997; 27(2):261-272.

Smyth, et al. Markers of Apoptosis: Methods for Elucidating the Mechanism of Apoptotic Cell Death from the Nervous System. Biotechniques. 2000; 32(3):648-665.

Somani, S.M. (Ed.). Chemical Warfare Agents. Academic Press. New York. 1992.

Sweeney, et al. A Cell Culture Analogue of Rodent Physiology: Application to Naphthalene Toxicology. Toxic. In Vitro. 1995; 9(3):307-316.

Williamson, et al. Phosphatidylserine Exposure and Phagocytosis of Apoptotic Cells. Methods in Cell Biology. 2001; 66:339-364.

Wronski, et al. Two-Color, Fluorescence-Based Microplate Assay for Apoptosis Detection. Biotechniques. 2002; 32(3):666-668.

Yamazaki, et al. Rat Cytochrome P450 1A and 3A Enzymes Involved in Bioactivation of Tegafur to 5-Fluorouracil and Autoinduced by Tegafur in Liver Microsomes. Drug Met. Disp. 2000; 29(6):794-797.

Shuler, et al., U.S. Appl. No. 11/470,587, entitled "Devices and methods for pharmacokinetic-based cell culture system," filed Sep. 6, 2006.

Shuler, et al., U.S. Appl. No. 11/470,595, entitled "Devices and methods for pharmacokinetic-based cell culture system," filed Sep. 6, 2006.

Shuler, et al., U.S. Appl. No. 11/530,363, entitled "Devices and methods for pharmacokinetic-based cell culture system," filed Sep. 8, 2006.

Shuler, et al., U.S. Appl. No. 11/530,400, entitled "Devices and methods for pharmacokinetic-based cell culture system," filed Sep. 8, 2006.

Heuschkel, M.O., et al. 1998. Buried microchannels in photopolymer for delivering of solutions to neurons in a network. *Sensors and Actuators*. B48: 356-361.

Final office action dated Dec. 7, 2010 for U.S. Appl. No. 11/436,100.

International Preliminary Report on Patentability dated Jul. 13, 2010 for PCT Application No. US2009/030686.

International search report dated Apr. 25, 2007 for PCT US2006/18951.

International search report dated Nov. 3, 2003 for PCT US2002/13083.

International search report dated Jul. 30, 2010 for PCT Application No. US2009/065781.

International search report dated Aug. 20, 2009 for PCT Application No. US2009/030686.

International Search Report dated Sep. 20, 2007 PCT/US06/43322.

Office action dated Mar. 4, 2010 for U.S. Appl. No. 11/436,100.

Office action dated Apr. 1, 2009 for U.S. Appl. No. 11/436,042.

Office action dated Jun. 23, 2010 for U.S. Appl. No. 11/470,576.

Office action dated Sep. 17, 2010 for U.S. Appl. No. 11/925,677.

Office action dated Sep. 17, 2010 for U.S. Appl. No. 11/925,687.

Office action dated Nov. 18, 2008 for U.S. Appl. No. 10/954,720.

Office action dated Nov. 30, 2007 for U.S. Appl. No. 11/556,956.

Sheridan et al. Initial experience with a composite autologous skin substitute. Burns. Aug. 27, 2001(5):421-4.

Sin, et al. Animal on a chip: a microscale cell culture analog device for evaluating toxicological and pharmacological profiles. Proc. SPIE vol. 4560, 2001; p. 98-101.

Office action dated May 25, 2011 for U.S. Appl. No. 11/925,677.

\* cited by examiner

DEVICES AND METHODS FOR PHARMACOKINETIC-BASED CELL CULTURE SYSTEM

CROSS-REFERENCES TO RELATED APPLICATIONS

The present application is a continuation of commonly assigned U.S. Pat. No. 7,288,405, which issued from U.S. patent application. Ser. No. 10/133,977, filed Apr. 25, 2002, which claims priority to U.S. Provisional Patent Application Ser. No. 60/286,493, filed Apr. 25, 2001, the entirety of which is incorporated herein by reference.

STATEMENT REGARDING GOVERNMENT RIGHTS

This invention was supported at least in part under grant number NAG8-1372 from the National Aeronautics and Space Administration. The U.S. Government may have certain rights in the invention.

FIELD OF THE INVENTION

The field of the invention is cell culture devices and methods of use.

BACKGROUND OF THE INVENTION

Pharmacokinetics is the study of the fate of pharmaceuticals and other biologically active compounds from the time they are introduced into the body until they are eliminated. For example, the sequence of events for an oral drug can include absorption through the various mucosal surfaces, distribution via the blood stream to various tissues, biotransformation in the liver and other tissues, action at the target site, and elimination of drug or metabolites in urine or bile. Pharmacokinetics provides a rational means of approaching the metabolism of a compound in a biological system. For reviews of pharmacokinetic equations and models, see, for example, Poulin and Theil (2000) J Pharm Sci. 89 (1):16-35; Slob et al. (1997) Crit Rev Toxicol. 27 (3):261-72; Haddad et al. (1996) Toxicol Lett. 85 (2):113-26; Hoang (1995) Toxicol Lett. 79 (1-3):99-106; Knaak et al. (1995) Toxicol Lett. 79 (1-3):87-98; and Ball and Schwartz (1994) Comput Biol Med. 24 (4):269-76.

One of the fundamental challenges researchers face in drug, environmental, nutritional, consumer product safety, and toxicology studies is the extrapolation of metabolic data and risk assessment from in vitro cell culture assays to animals. Although some conclusions can be drawn with the application of appropriate pharmacokinetic principles, there are still substantial limitations. One concern is that current screening assays utilize cells under conditions that do not replicate their function in their natural setting. The circulatory flow, interaction with other tissues, and other parameters associated with a physiological response are not found in standard tissue culture formats. For example, in a macroscale cell culture analog (CCA) system, cells are grown at the bottom of chambers. These systems have non-physiological high liquid-to-cell ratios, and have an unrealistic ratio of cell types (e.g., ratio of liver to lung cells). In a variant form of the macroscale CCA system the cells are grown on microcarrier beads. These systems more closely resemble physiological conditions, but are still deficient because they do not mimic physiological conditions accurately enough for predictive studies. Therefore, the resulting assay data is not based on the pattern of drug or toxin exposure that would be found in an animal.

Within living beings, concentration, time and metabolism interact to influence the intensity and duration of a pharmacologic or toxic response. For example, in vivo the presence of liver function strongly affects drug metabolism and bioavailability. Elimination of an active drug by the liver occurs by biotransformation and excretion. Biotransformation reactions include reactions catalyzed by the cytochrome P450 enzymes, which transform many chemically diverse drugs. A second biotransformation phase can add a hydrophilic group, such as glutathione, glucuronic acid or sulfate, to increase water solubility and speed elimination through the kidneys.

While biotransformation can be beneficial, it may also have undesirable consequences. Toxicity results from a complex interaction between a compound and the organism. During the process of biotransformation, the resulting metabolite can be more toxic than the parent compound. The single-cell assays used by many for toxicity screening miss these complex inter-cellular and inter-tissue effects.

Consequently, accurate prediction of human responsiveness to potential pharmaceuticals is difficult, often unreliable, and invariably expensive. Traditional methods of predicting human response utilize surrogates—typically either static, homogeneous in vitro cell culture assays or in vivo animal studies. In vitro cell culture assays are of limited value because they do not accurately mimic the complex environment a drug candidate is subjected to within a human and thus cannot accurately predict human risk. Similarly, while in vivo animal testing can account for these complex inter-cellular and inter-tissue effects not observable from in vitro cell-based assays, in vivo animal studies are extremely expensive, labor-intensive, time consuming, and often the results are of doubtful relevance when correlating human risk.

U.S. Pat. No. 5,612,188 issued to Shuler et al. describes a multicompartmental cell culture system. This culture system uses large components, such as culture chambers, sensors, and pumps, which require the use of large quantities of culture media, cells and test compounds. This system is very expensive to operate and requires a large amount of space in which to operate. Because this system is on such a large scale, the physiological parameters vary considerably from those found in an in vivo situation. It is impossible to accurately generate physiologically realistic conditions at such a large scale.

The development of microscale screening assays and devices that can provide better, faster and more efficient prediction of in vivo toxicity and clinical drug performance is of great interest in a number of fields, and is addressed in the present invention. Such a microscale device would accurately produce physiologically realistic parameters and would more closely model the desired in vivo system being tested.

SUMMARY OF THE INVENTION

Devices, in vitro cell cultures, and methods are provided for a microscale cell culture analog (CCA) device. The devices of the invention permit cells to be maintained in vitro, under conditions with pharmacokinetic parameter values similar to those found in vivo. Pharmacokinetic parameters of interest include interactions between cells, liquid residence time, liquid to cell ratios, relative size of organs, metabolism by cells, shear stress, and the like. By providing a pharmacokinetic-based culture system that mimics the natural state of cells, the predictive value and in vivo relevance of screening and toxicity assays is enhanced.

The microscale culture device comprises a fluidic network of channels segregated into discrete but interconnected chambers. The specific chamber geometry is designed to provide cellular interactions, liquid flow, and liquid residence parameters that correlate with those found for the corresponding cells, tissues, or organs in vivo. The fluidics are designed to accurately represent primary elements of the circulatory or lymphatic systems. In one embodiment, these components are integrated into a chip format. The design and validation of these geometries is based on a physiological-based pharmacokinetic (PBPK) model; a mathematical model that represents the body as interconnected compartments representing different tissues.

The device can be seeded with the appropriate cells for each culture chamber. For example, a chamber designed to provide liver pharmacokinetic parameters is seeded with hepatocytes, and may be in fluid connection with adipocytes seeded in a chamber designed to provide fat tissue pharmacokinetics. The result is a pharmacokinetic-based cell culture system that accurately represents, for example, the tissue size ratio, tissue to blood volume ratio, drug residence time of the animal it is modeling.

In one embodiment, a system includes a first microscale culture device and a control instrument. The first microscale culture device has a number of microscale chambers with geometries that simulate a plurality of in vivo interactions with a culture medium, wherein each chamber includes an inlet and an outlet for flow of the culture medium, and a microfluidic channel interconnecting the chambers. The control instrument is coupled to the first microscale culture device, and includes a computer to acquire data from, and control pharmacokinetic parameters of, the first microscale culture device.

In another embodiment, a computer includes a microprocessor, a general memory, a non-volatile storage element, an input/output interface that includes an interface to a microscale culture device having one or more sensors, and computer software. The computer software is executable on the microprocessor to analyze data from the sensors to measure physiological events in a number of chambers of the microscale culture device, regulate fluid flow rates of a culture medium in the chambers of the microscale culture device, detect biological or toxicological reactions in the chambers of the microscale culture device, and upon detection, change one or more pharmacokinetic parameters of the microscale culture device.

As used herein the singular forms "a" and "the" include plural referents unless the context clearly dictates otherwise. For example, "a compound" refers to one or more of such compounds, while "the cell" includes a particular cell as well as other family members and equivalents thereof as known to those skilled in the art.

BRIEF DESCRIPTION OF THE DRAWINGS

FIG. 5A shows coating a silicon wafer with a positive photoresist material. FIG. 5B shows exposing resist-coated silicon wafer to UV light through a photomaterial. FIG. 5C shows developing the photoresist material. FIG. 5D shows etching silicon. FIG. 5E shows striping the photoresist material and evaporating gold. FIG. 5F shows electroplating nickel. FIG. 5G shows removing silicon and embossing polymer.

DETAILED DESCRIPTION OF THE EMBODIMENTS

The present inventors have developed a microscale cell culture analog (CCA) system. Such a microscale CCA system has many advantages over the earlier macroscale systems. The microscale systems use smaller quantities of reagents, fewer cells (which allow the use of authentic primary cells rather than cultured cells), are more physiologically realistic (e.g., residence times, organ ratios, shear stresses), have a lower device cost, and are smaller in size (multiple tests and statistical analysis available). Moreover, multiple biosensors can be incorporated on the same chip.

In simplest terms, the chip of the present invention provides an accurate in vitro surrogate of an whole animal or human. To accomplish this, an initial design was produced using a physiological-based pharmacokinetic (PBPK) model—a mathematical model that represents the body as interconnected compartments specific for a particular organ. From the PBPK model and published empirical data, a lengthy and extensive development program resulted in a microscale device that accurately mimics the known tissue size ratio, tissue to blood volume ratio, drug residence time, and other important physiological parameters of a whole animal or human. In essence, the chip technology of the present invention is a microscale model of a whole animal or human (~1/1000,000$^{th}$ for human).

Figure 15:
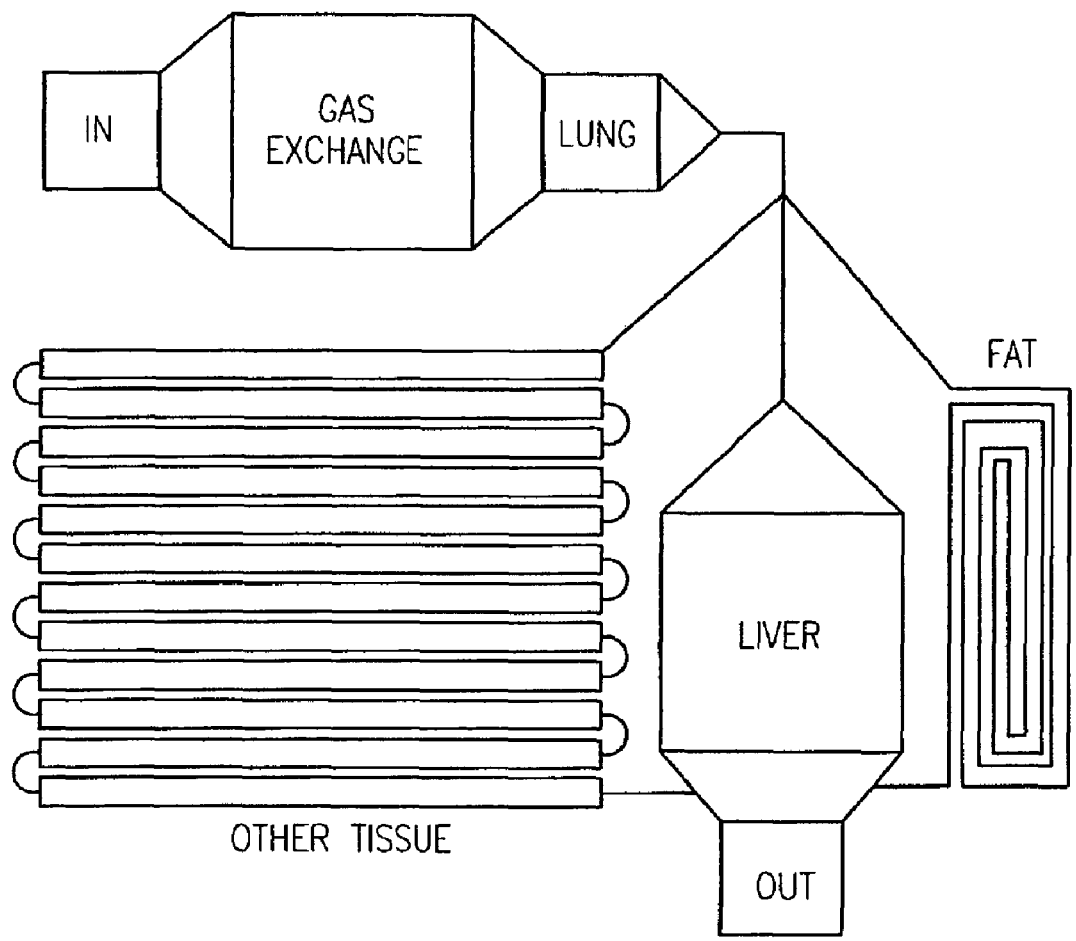
FIG. 15 is a schematic diagram of the four-compartment chip.

In operation, the device replicates a re-circulating multi-organ system by segregating living cells into discrete, interconnected "organ" compartments (see e.g., FIG. 15). The fluidics are designed such that the primary elements of the circulatory system and the interactions of the organ systems are accurately mimicked. Each organ compartment contains a particular cell type carefully selected or engineered to mimic the primary function(s) of the corresponding whole organ (e.g. xenobiotic metabolism by the liver). The cell type may be adherent or non-adherent and derived from standard cell culture lines or primary tissue. Human cells are used for human surrogates or cells from other species as appropriate.

The organ compartments are connected by a re-circulating culture medium that acts as a "blood surrogate." Test agents in the medium are distributed and interact with the cells in the organ compartments much as they would in the human body or whole animal. The effects of these compounds and/or their metabolites on the various cell types are detected by measuring or monitoring key physiological events such as cell death, cell proliferation, differentiation, immune response, or perturbations in metabolism or signal transduction pathways. In addition, pharmacokinetic data can be determined by collecting and analyzing aliquots of the culture medium for drug metabolites.

The microscale chip device of the present invention offers both the cost and throughput advantages of traditional cell culture assays and also the high informational content of whole animal models. Unlike whole animal tests however, the chip is inexpensive and largely disposable. The low fluid volume (~5 µl) of the device provides the high sensitivity and throughput characteristic of microfluidic devices. Moreover, the readout of the device is highly flexible and assay independent—almost any cell type or assay can be used without modification. Numerous biological assays based on optical interrogation and readout (e.g., fluorescence, luminescence) are available, thus making real-time monitoring feasible. Alternatively, standard pathology, biochemical, genomic or proteomic assays can be utilized directly as the system can be designed to be fully compatible with the traditional coverslip (22 mm×22 mm) or 96 well format. Further, genetically engineered cells can be used for specialized end-user applications. In addition, "3D" chips can be used to encompass additional compartments and modules to analyze gastrointestinal tract or blood-brain barrier absorption.

Unlike traditional in vitro assays, the chip of the present invention more closely mimics the complex multi-tissue (liver, lung, adipose, circulatory system, etc.) biology of the whole organism. Drug candidates are exposed to a more realistic animal or human physiological environment thus providing higher and more accurate informational content (e.g., absorption, distribution, bioaccumulation, metabolism, excretion, efficacy and toxicity) than typical in vitro assays. These benefits directly affect the safety and efficacy predictions of drug leads and particularly, their prioritization before entering into expensive and time-consuming non-clinical or clinical trials. This prioritization-increases drug development throughput, reduces the number of animals needed for toxicological screening, decreases the costs of non-clinical studies, and increases the efficiency of clinical trials by allowing rapid and direct assessment of potential toxicity or lack of efficacy prior to entering these trials.

These demonstrate some of the advantages of the chip technology of the present invention. In summary, acquisition of data is rapid when compared to traditional in vitro cell culture assays, animal studies, or clinical trials. The data is also robust, providing highly predictive content not available from traditional in vitro assays. The chip platform is designed such that it is fully compatible with existing assays—either in the standard coverslip or 96 well format. The device itself is configurable for any animal species or combination of multiple organ compartments. Individual chips are priced cost-effectively as disposables. Moreover, the low volume of the device further reduces reagent costs in screening potential compounds.

Unlike currently available technologies, the present chip system greatly increases the success rates not only at the clinical phase, but also in reducing the number of compounds that need to undergo pre-clinical testing. Consequently, a pharmaceutical company can (1) determine which drug candidates have the potential to be toxic to humans early in the development process; (2) better select the animal species that best predict human response; and (3) determine which drug candidate has the potential to be efficacious. Thus, the chip of the present invention greatly increases the success rates and decrease the development time of marketable drugs.

Pharmokinetic-Based Microscale Culture Device

Devices, in vitro cell cultures, and methods are provided for a CCA device. The subject methods and devices provide a means whereby cells are maintained in vitro in a physiologically representative environment, thereby improving the predictive value and in vivo relevance of screening and toxicity assays. A microscale pharmacokinetic culture device of the present invention is seeded with the appropriate cells for each culture chamber, which culture system can then be used for compound screening, toxicity assays, models for development of cells of interest, models of infection kinetics, and the like. An input variable, which may be; for example, a compound, sample, genetic sequence, pathogen, cell (such as a stem or progenitor cell), is added to an established culture system. Various cellular outputs may be assessed to determine the response of the cells to the input variable, including pH of the medium, concentration of $O_2$ and $CO_2$ in the medium, expression of proteins and other cellular markers, cell viability, or release of cellular products into the culture medium.

Figure 18A:
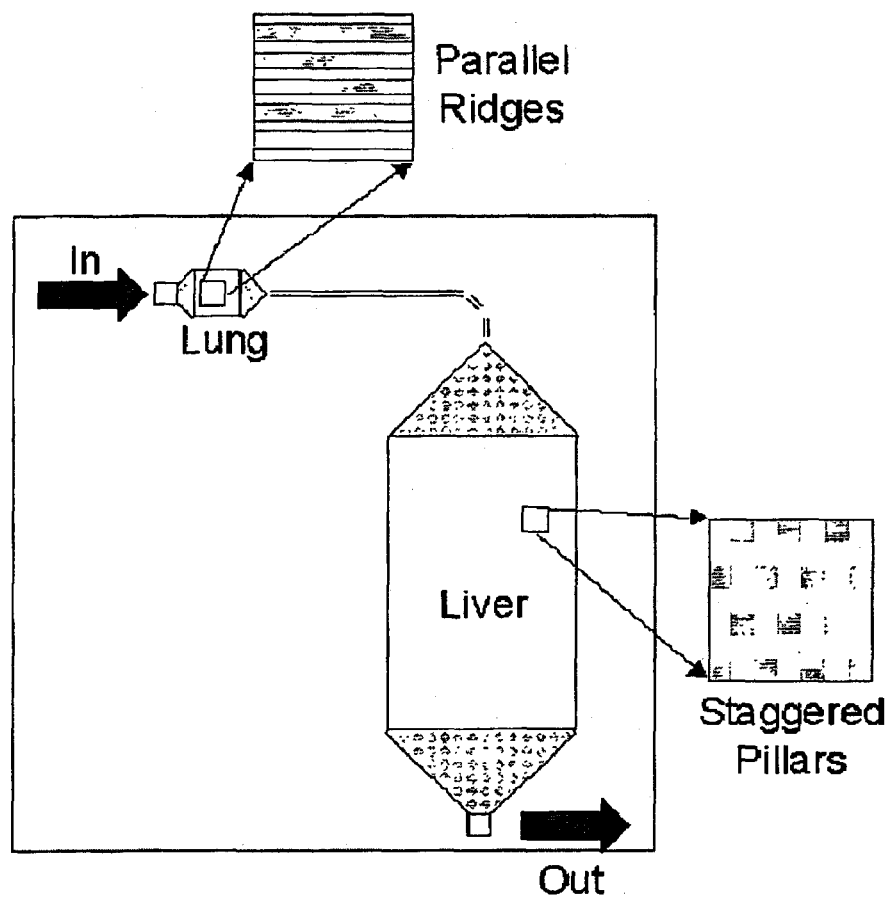
FIG. 18A depicts a "second generation" device.
Figure 18B:
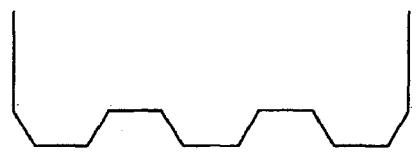
FIG. 18B depicts 5 µm tall ridges in a chamber.
Figure 18C:
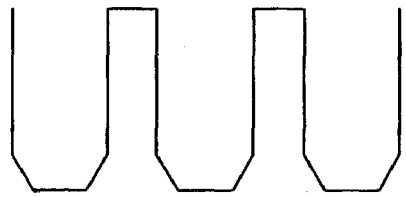
FIG. 18C depicts 20 µm tall pillars in a chamber.

The design and geometry of the culture substrate, or device, provides for the unique growth conditions of the invention. Each device comprises one or more chambers, which are interconnected by fluidic channels. Each chamber may have a geometric configuration distinct from other chamber(s) present on the device. For example, ore embodiment of the device consists of chambers representing lung, liver, and other tissues (FIG. 18A). The lung chamber in this embodiment contains 5 µm tall ridges in order to achieve realistic cell to liquid volume ratio and liquid residence time (FIG. 18B). The liver chamber in this embodiment contains 20 µm tall pillars to achieve realistic cell to liquid volume ratio and liquid residence time (FIG. 18C). The device also comprises inlet and outlet ports so that the culture medium can be circulated.

In one embodiment, the culture device is in a chip format, i.e., the chambers and fluidic channels are fabricated or molded from a fabricated master, such that the device is formed either as a single unit or as a modular system with one or more chambers on separate units. Generally the chip format is provided in a small scale, usually not more than about 10 cm on a side, or even not more than about 5 cm on a side. It may even be only about 2 cm on a side or smaller. In another example, the chip may be housed in a 96 well format in which the individual chips are less than 0.9 cm×0.9 cm. The chambers and fluidic channels are correspondingly micro-scale in size.

In another embodiment, the culture device is in the form of an integrated device consisting of a table-top instrument housing multiple microscale chips fabricated as disposable plastic polymer-based components. The instrument may consist of a base with depressions to accommodate individual cell chips or alternatively, a single "chip" in a standard 96 well format (i.e., 96 individual chips in a 8×12 format). The instrument top, when closed seals the chips and provide fluid interconnects. The instrument contains low volume pumps to re-circulate fluid to the chips and small 3-way valves with injection loops to provide introduction of test compounds, or alternatively draws compounds directly from a 96- or 384-well plate. Multiple compounds can be evaluated simultaneously for efficacy, toxicity, and/or metabolite production using this instrument. The instrument may also integrate on-chip fluorescence detection for real-time physiology monitoring using well-characterized biomarkers.

The device may include a mechanism for obtaining signals from the cells and culture medium. The signals from different chambers and channels can be monitored in real time. For example, biosensors can be integrated or external to the device, which permit real-time readout of the physiological status of the cells in the system.

The present invention provides an ideal system for high-throughput screening to identify positive or negative response to a range of substances such as, for example, pharmaceutical compositions, vaccine preparations, cytotoxic chemicals, mutagens, cytokines, chemokines, growth factors, hormones, inhibitory compounds, chemotherapeutic agents, and a host of other compounds or factors. The substance to be tested can be either naturally-occurring or synthetic, and can be organic or inorganic.

For example, the activity of a cytotoxic compound can be measured by its ability to damage or kill cells in culture. This may readily be assessed by vital staining techniques. The effect of growth/regulatory factors may be assessed by analyzing the cellular content of the matrix, e.g. by total cell counts, and differential cell counts. This may be accomplished using standard cytological and/or histological techniques including the use of immunocytochemical techniques employing antibodies that define type-specific cellular antigens. The effect of various drugs on normal cells cultured in the device may be assessed. For example, drugs that increase red blood cell formation can be tested on bone marrow cultures. Drugs that affect cholesterol metabolism, e.g., by lowering cholesterol production, can be tested on a liver system. Cultures of tumor cells may be used as model systems to test, for example, the efficacy of anti-tumor agents.

The device of the invention may be used as model systems for the study of physiologic or pathologic conditions. For example, in a specific embodiment of the invention, a device can be used as a model for the blood-brain barrier; such a model system can be used to study the penetration of substances through the blood-brain barrier. In an additional embodiment, and not by way of limitation, a device containing mucosal epithelium may be used as a model system to study herpesvirus or papillomavirus infection; such a model system can be used to test the efficacy of anti-viral medications.

The device of the present invention may also be used to aid in the diagnosis and treatment of malignancies and diseases. For example, biopsies of any tissue (e.g., bone marrow, skin, liver) may be taken from a patient suspected of having a malignancy. The patient's culture can be used in vitro to screen cytotoxic and or pharmaceutical compounds in order to identify those that are most efficacious; i.e., those that kill the malignant or diseased cells, yet spare the normal cells. These agents can then be used to therapeutically treat the patient.

In yet another embodiment of the invention, the device can be used in vitro to produce biological products in high yield. For example, a cell that naturally produces large quantities of a particular biological product (e.g., a growth factor, regulatory factor, peptide hormone, antibody), or a host cell genetically engineered to produce a foreign gene product, can be clonally expanded using the in vitro device. If a transformed cell excretes the gene product into the nutrient medium, the product may be readily isolated from the spent or conditioned medium using standard separation techniques (e.g., HPLC, column chromatography, electrophoretic techniques, to name but a few). A "bioreactor" can be devised that would take advantage of the continuous flow method for feeding cultures in vitro. Essentially, as fresh media is passed through the cultures in the device, the gene product will be washed out of the culture along with the cells released from the culture. The gene product can be isolated (e.g., by HPLC column chromatography, electrophoresis) from the outflow of spent or conditioned media.

The present invention also provides a system for screening or measuring the effects of various environmental conditions or compounds on a biological system. For example air or water conditions could be mimicked or varied in the device. The impact of different known or suspected toxic substances could be tested. The present invention further provides a system for screening consumer products, such as cosmetics, cleansers, or lotions. It also provides a system for determining the safety and/or efficacy of nutriceuticals, nutritional supplements, or food additives. The present invention could also be used as a miniature bioreactor or cellular production platform to produce cellular products in quantity.

Typical efficacy or toxicity experiments using the chip format microscale culture device of the present invention are completed within 24 to 48 hours or less depending on experimental design. Extended experiments, however, can be performed in order to test for the effects of chronic exposure (e.g., genotoxicity, carcinogenicity, or latent diseases).

The present invention provides novel devices, systems and methods as set forth within this specification. In general, all technical and scientific terms used herein have the same meaning as commonly understood to one of ordinary skill in the art to which this invention belongs, unless clearly indicated otherwise For clarification, listed below are definitions for certain terms used herein to describe the present invention. These definitions apply to the terms as they are used throughout this specification, unless otherwise clearly indicated.

DEFINITION OF TERMS

Pharmacokinetic-based culture system: An in vitro cell culture system, wherein the cells are maintained under conditions providing pharmacokinetic parameter values that model those found in vivo. A pharmacokinetic culture device comprises a fluidic network of channels segregated into discrete but interconnected chambers, where the specific chamber geometry is designed to provide cellular interactions, liquid flow, and liquid residence parameters that correlate with those found for the corresponding cells, tissue, or organ system in vivo. The device is seeded with cells that are appropriate for conditions being modeled, e.g., liver cells in a liver-based culture chamber, lung cells in a lung-based culture chamber, and the like, to provide the culture system.

The culture systems of the invention provide for at least one pharmacokinetic parameter value that is comparable to values obtained for the cell, tissue, or organ system of interest in vivo, preferably at least two parameter values, and may provide for three or more comparable parameter values. Pharmacokinetic parameters of interest include, for example, interactions between cells, liquid residence time, liquid to cell ratios, metabolism by cells, or shear stress.

By comparable values, it is meant that the actual values do not deviate more than 25% from the theoretical values. For example, the calculated or theoretical value for the liquid residence time in the lung compartment for a rat is 2 seconds and the actual value measured in the lung cell culture chamber of a rat CCA device was 2.5+/−0.7 seconds.

The pharmacokinetic parameter value is obtained by using the equations of a PBPK model. Such equations have been described in the art, for example see Poulin and Theil (2000) J Pharm Sci. 89 (1):16-35; Slob et al. (1997) Crit Rev Toxicol. 27 (3):261-72; Haddad et al. (1996) Toxicol Lett. 85 (2):113-26; Hoang (1995) Toxicol Lett. 79 (1-3):99-106; Knaak et al. (1995) Toxicol Lett. 79 (1-3):87-98; and Ball and Schwartz (1994) Comput Biol Med. 24 (4):269-76, herein incorporated by reference. Phannacokinetic parameters can also be obtained from the published literature, for example see Buckpitt et al., (1984) J. Pharmacol. Exp. Ther. 231:291-300; DelRaso (1993) Toxicol. Lett. 68:91-99; Haies et al., (1981) Am. Rev. Respir. Dis. 123:533-541.

Specific physiologic parameters of interest include tissue or organ liquid residence time, tissue or organ mass, liquid-to-cell volume ratio, cell shear stress, etc. Physiologically relevant parameter values can be obtained empirically according to conventional methods, or can be obtained from values known in the art and publicly available. Pharmacokinetic parameter values of interest are obtained for an animal, usually a mammal, although other animal models can also find use, e.g., insects, fish, reptiles, or avians. Mammals include laboratory animals, e.g., mouse, rat, rabbit, or guinea pig mammals of economic value, e.g. equine, ovine, caprine, bovine, canine, or feline; primates, including monkeys, apes, or humans; and the like. Different values may be obtained and used for animals of different ages, e.g., fetal, neonatal, infant, child, adult, or elderly; and for different physiological states, e.g., diseased, after contact with a pharmaceutically active agent, after infection, or under conditions of altered atmospheric pressure.

Information relevant to the pharmacokinetic parameter values, as well as mass balance equations applicable to various substances to be modeled in the system, is optionally provided in a data processing component of the culture system, e.g., look-up tables in general purpose memory set aside for storage, and the like. These equations represent physiologically-based pharmacokinetic models for various biological/chemical substances in systems.

Pharmacokinetic culture device: The culture device of the invention provides a substrate for cell growth. Each device comprises at least one chamber, usually at least two chambers, and may comprise three or more chambers, where the chambers are interconnected by fluidic channels. The chambers can be on a single substrate or on different substrates. Preferably each chamber has a geometric configuration distinct from other chamber(s) present on the device. The device contains a cover to seal the chambers and channels and comprises at least one inlet and one outlet port that allow for recirculation of the culture medium. The device contains a mechanism to pump the culture medium through the system. The culture medium is designed to maintain viability of the cultured cells. The device contains a mechanism by which test compounds can be introduced to the system.

In one embodiment of the invention, the device is fabricated on a microscale as a single unit of not more than about 2.5 cm in a side, preferably comprising at least two interconnected chambers. The two organ compartments are connected by a channel of from about 50-150 µm wide and 15-25 µm deep. For example, one chamber may represent the lung, comprising an interconnected array of parallel channels, usually at least about 10 channels, preferably at least about 20 channels. Such channel may have typical microfluidic dimensions, e.g., about 30-50 µm wide, 5-15 µm deep and 3-7 mm long. Another compartment may represent the liver, comprising two or more parallel channels, usually from about 50-150 µm wide, 15-25 µm deep and 5-15 cm long in a serpentine shape.

The device will usually include a mechanism for obtaining signals from the cells and culture medium. The signals from different chambers and channels can be monitored in real time. For example, biosensors can be integrated or external to the device, which permit real-time readout of the physiological status of the cells in the system.

The pharmacokinetic culture device of the present invention may be provided as a chip or substrate. In addition to enhancing the fluid dynamics, such microsystems save on space, particularly when used in highly parallel systems, and can be produced inexpensively. The culture device can be formed from a polymer such as but not limited to polystyrene, and disposed of after one use, eliminating the need for sterilization. As a result, the in vitro subsystem can be produced inexpensively and widely used. In addition, the cells may be grown in a three-dimensional manner, e.g., to form a tube, which more closely replicates the in vivo environment.

To model the metabolic response of an animal for any particular agent, a bank of parallel or multiplex arrays comprising a plurality (i.e., at least two) of the cell culture systems, where each system can be identical, or can be varied with predetermined parameter values or input agents and concentrations. The array may comprise at least about 10, or may even be as many as 100 or more systems. Advantageously, the cell culture systems on microchips can be housed within a single chamber so that all the cell culture systems under are exposed to the same conditions during an assay.

Alternatively, multiple chips may be interconnected to form a single device, e.g., to mimic gastrointestinal barriers or the blood brain barrier.

Cells: Cells for use in the assays of the invention can be an organism, a single cell type derived from an organism, and can be a mixture of cell types, as is typical of in vivo situations. The culture conditions may include, for example, temperature, pH, presence of factors, presence of other cell types, and the like. A variety of animal cells can be used, including any of the animals for which pharmacokinetic parameter values can be obtained, as previously described.

The invention is suitable for use with any cell type, including primary cells, stem cells, progenitor cells, normal, genetically-modified, genetically altered, immortalized, and transformed cell lines. The present invention is suitable for use with single cell types or cell lines, or with combinations of different cell types. Preferably the cultured cells maintain the ability to respond to stimuli that elicit a response in their naturally occurring counterparts. These may be derived from all sources such as eukaryotic or prokaryotic cells. The eukaryotic cells can be plant, or animal in nature, such as human, simian, or rodent. They may be of any tissue type (e.g., heart, stomach, kidney, intestine, lung, liver, fat, bone, cartilage, skeletal muscle, smooth muscle, cardiac muscle, bone marrow, muscle, brain, pancreas), and cell type (e.g., epithelial, endothelial, mesenchymal, adipocyte, hematopoietic). Further, a cross-section of tissue or an organ can be used. For example, a cross-section of an artery, vein, gastrointestinal tract, esophagus, or colon could be used.

In addition, cells that have been genetically altered or modified so as to contain a non-native "recombinant" (also called "exogenous") nucleic acid sequence, or modified by antisense technology to provide a gain or loss of genetic function may be utilized with the invention. Methods for generating genetically modified cells are known in the art, see for example "Current Protocols in Molecular Biology," Ausubel et al., eds, John Wiley & Sons, New York, N.Y., 2000. The cells could be terminally differentiated or undifferentiated, such as a stem cell. The cells of the present invention could be cultured cells from a variety of genetically diverse individuals who may respond differently to biologic and pharmacologic agents. Genetic diversity can have indirect and direct effects on disease susceptibility. In a direct case, even a single nucleotide change, resulting in a single nucleotide polymorphism (SNP), can alter the amino acid sequence of a protein and directly contribute to disease or disease susceptibility. For example, certain APO-lipoprotein E genotypes have been associated with onset and progression of Alzheimer's disease in some individuals.

When certain polymorphisms are associated with a particular disease phenotype, cells from individuals identified as carriers of the polymorphism can be studied for developmental anomalies, using cells from non-carriers as a control. The present invention provide an experimental system for studying developmental anomalies associated with particular genetic disease presentations since several different cell types can be studied simultaneously, and linked to related cells. For example, neuronal precursors, glial cells, or other cells of neural origin, can be used in a device to characterize the cellular effects of a compound on the nervous system. Also, systems can be set up so that cells can be studied to identify genetic elements that affect drug sensitivity, chemokine and cytokine response, response to growth factors, hormones, and inhibitors, as well as responses to changes in receptor expression and/or function. This information can be invaluable in designing treatment methodologies for diseases of genetic origin or for which there is a genetic predisposition.

In one embodiment of the invention, the cells are involved in the detoxification and metabolism of pharmaceutically active compounds, e.g., liver cells, including hepatocytes; kidney cells including tubule cells; fat cells including adipocytes that can retain organic compounds for long periods of time. These cells may be combined in a culture system with cells such as lung cells, which are involved in respiration and oxygenation processes. These cells may also be combined with cells that are particularly sensitive to damage from an agent of interest, e.g., gut epithelial cells, bone marrow cells, and other normally rapidly dividing cells for agents that affect cell division. Neural cells may be present to monitor for the effect of an agent for neurotoxicity, and the like.

The growth characteristics of tumors, and the response of surrounding tissues and the immune system to tumor growth are also of interest. Degenerative diseases, including affected tissues and surrounding areas may be exploited to determine both the response of the affected tissue, and the interactions with other parts of the body.

The term "environment" or "culture condition" encompasses cells, media, factors, time and temperature. Environments may also include drugs and other compounds, particular atmospheric conditions, pH, salt composition, minerals, etc. Cell culturing is typically performed in a sterile environment mimicking physiological conditions, for example, at 37° C. in an incubator containing a humidified 92-95% air/5-8% $CO_2$ atmosphere. Cell culturing may be carried out in nutrient mixtures containing undefined biological fluids such a fetal calf serum, or media that is fully defined and serum free. A variety of culture media are known in the art and are commercially available.

The term "physiological conditions" as used herein is defined to mean that the cell culturing conditions are very specifically monitored to mimic as closely as possible the natural tissue conditions for a particular type of cell in vivo. These conditions include such parameters as liquid residence time (i.e., the time that a liquid stays in an organ); cell to blood volume ratio, sheer stress on the cells, size of compartment comparable to natural organ.

Screening Assays: Drugs, toxins, cells, pathogens, samples, etc., herein referred to generically as "input variables" are screened for biological activity by adding to the pharmacokinetic-based culture system, and then assessing the cultured cells for changes in output variables of interest, e.g., consumption of $O_2$, production of $CO_2$, cell viability, or expression of proteins of interest. The input variables are typically added in solution, or readily soluble form, to the medium of cells in culture. The input variables may be added using a flow through system, or alternatively, adding a bolus to an otherwise static solution. In a flow-through system, two fluids are used, where one is a physiologically neutral solution, and the other is the same solution with the test compound added. The first fluid is passed over the cells, followed by the second. In a single solution method, a bolus of the test input variables is added to the volume of medium surrounding the cells. The overall composition of the culture medium should not change significantly with the addition of the bolus, or between the two solutions in a flow through method.

Preferred input variables formulations do not include additional components, such as preservatives, that have a significant effect on the overall formulation. Thus, preferred formulations include a biologically active agent and a physiologically acceptable carrier, e.g., water, ethanol, or DMSO. However, if an agent is liquid without an excipient, the formulation may be only the compound itself.

Preferred input variables include, but are not limited to, viruses, viral particles, liposomes, nanoparticles, biodegradable polymers, radiolabeled particles, radiolabeled biomolecules, toxin-conjugated particles, toxin-conjugated biomolecules, and particles or biomolecules conjugated with stabilizing agents. A "stabilizing agent" is an agent used to stabilize drugs and provide a controlled release. Such agents include albumin, polyethyleneglycol, poly(ethylene-co-vinyl acetate), and poly(lactide-co-glycolide).

A plurality of assays may be run in parallel with different input variable concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e., at zero concentration or below the level of detection.

Input variables of interest encompass numerous chemical classes, though frequently they are organic molecules. A preferred embodiment is the use of the methods of the invention to screen samples for toxicity, e.g., environmental samples or drug. Candidate agents may comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Included are pharmacologically active drugs and genetically active molecules. Compounds of interest include chemotherapeutic agents, anti-inflammatory agents, hormones or hormone antagonists, ion channel modifiers, and neuroactive agents. Exemplary of pharmaceutical agents suitable for this invention are those described in "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming Organs; Hormones and Hormone Antagonists; Vitamins, Dermatology; and Toxicology, all incorporated-herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. While many samples will comprise compounds in solution, solid samples that can be dissolved in a suitable solvent may also be assayed. Samples of interest include environmental samples, e.g., ground water, sea water, or mining waste; biological samples, e.g., lysates prepared from crops or tissue samples; manufacturing samples, e.g., time course during preparation of pharmaceuticals; as well as libraries of compounds prepared for analysis; and the like. Samples of interest include compounds being assessed for potential therapeutic value, e.g., drug candidates from plant or fungal cells.

The term "samples" also includes the fluids described above to which additional components have been added, for example, components that affect the ionic strength, pH, or total protein concentration. In addition, the samples may be treated to achieve at least partial fractionation or concentration. Biological samples may be stored if care is taken to reduce degradation of the compound, e.g., under nitrogen, frozen, or a combination thereof. The volume of sample used is sufficient to allow for measurable detection, usually from about 0.1 µl to 1 ml of a biological sample is sufficient.

Compounds and candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, naturally or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification to produce structural analogs.

Output variables: Output variables are quantifiable elements of cells, particularly elements that can be accurately measured in a high throughput system. An output can be any cell component or cell product including, e.g., viability, respiration, metabolism, cell surface determinant, receptor, protein or conformational or posttranslational modification thereof, lipid, carbohydrate, organic or inorganic molecule, mRNA, DNA, or a portion derived from such a cell component. While most outputs will provide a quantitative readout, in some instances a semi-quantitative or qualitative result will be obtained. Readouts may include a single determined value, or may include mean, median value or the variance. Characteristically a range of readout values will be obtained for each output. Variability is expected and a range of values for a set of test outputs can be established using standard statistical methods.

Various methods can be utilized for quantifying the presence of the selected markers. For measuring the amount of a molecule that is present, a convenient method is to label the molecule with a detectable moiety, which may be fluorescent, luminescent, radioactive, or enzymatically active. Fluorescent and luminescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g., by expressing them as green fluorescent protein chimeras inside cells (for a review, see Jones et al. (1999) Trends Biotechnol. 17 (12):477-81).

Output variables may be measured by immunoassay techniques such as, immunohistochemistry, radioimmunoassay (RIA) or enzyme linked immunosorbance assay (ELISA) and related non-enzymatic techniques. These techniques utilize specific antibodies as reporter molecules that are particularly useful due to their high degree of specificity for attaching to a single molecular target. Cell based ELISA or related non-enzymatic or fluorescence-based methods enable measurement of cell surface parameters. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Data analysis: The results of screening assays may be compared to results obtained from reference compounds, concentration curves, controls, etc. The comparison of results is accomplished by the use of suitable deduction protocols, AI systems, statistical comparisons, etc.

A database of reference output data can be compiled. These databases may include results from known agents or combinations of agents, as well as references from the analysis of cells treated under environmental conditions in which single or multiple environmental conditions or parameters are removed or specifically altered. A data matrix may be generated, where each point of the data matrix corresponds to a readout from a output variable, where data for each output may come from replicate determinations, e.g., multiple individual cells of the same type.

The readout may be a mean, average, median or the variance or other statistically or mathematically derived value associated with the measurement. The output readout information may be further refined by direct comparison with the corresponding reference readout. The absolute values obtained for each output under identical conditions will display a variability that is inherent in live biological systems and also reflects individual cellular variability as well as the variability inherent between individuals.

Cell Cultures and Cell Culture Devices

The culture devices of the invention comprise a microfluidic network of channels segregated into one or more discrete but interconnected chambers, preferably integrated into a chip format. The specific chamber geometry is designed to provide cellular interactions, liquid flow, and liquid residence parameters that correlate with those found for the corresponding cells, tissue, or organ systems in vivo.

Optimized chamber geometries can be developed by repeating the procedure of testing parameter values in response to fluid flows and changes in dimensions, until the selected values are obtained. Optimization of the substrate includes selecting the number of chambers, choosing a chamber geometry that provides the proper cell to volume ratio, selecting a chamber size that provides the proper tissue or organ size ratio, choosing the optimal fluid flow rates that provides for the correct liquid residence time, then calculating the cell shear stress based on these values. If the cell shear stress is over the maximum allowable value, new parameter values are selected and the process is repeated. Another embodiment of the CCA device includes where the cells are grown within hollow tubes rather than on the bottom and sides of channels or chambers. It has been demonstrated that cells growing in such a three-dimensional tissue construct are more authentic with respect to certain in vivo tissues (Griffith (1998) PhARMA Biol. Biotech. Conf., Coronado, Calif., March 15-18).

Three primary design parameters are considered in creating the 3-D culture device. The first is the residence time that the fluid is in contact with a particular tissue or within a well. The residence times are chosen to reflect the amount of time blood stays in contact with organ tissue, represented by a well, in one pass of the circulatory system. The second is the radius of the tubes the cells are grown in. For example, the radius of the tubes for replicating liver are within a range of 200-400 µm. It should be noted that if the radius of the tubes gets too large, the cells will essentially see a flat surface and will form a monolayer on the tube.

The third parameter is the proportion of flow that arrives at each module. Adjusting the geometry of the flow channels partitions the flow from the chambers. The channels or tubes to each module or chamber are typically of different lengths to equilibrate the pressure drops and balance the flow. After the fluid leaves the other tissues, it can be re-circulated by a pump. The flow rate through the tubes was calculated from the tube dimensions and the residence time. Given a flow rate, the shear stress on the cells was calculated to ensure that the value did not exceed the cells' stress limit. The very short residence time required in the lung tissue makes it impossible to use a well and tube approach for this organ. The shear stress is too high and therefore, the lung tissue section remains flow-over with a lung tissue monolayer.

Since the system of the present invention is interactive (i.e., the computer not only senses but also controls the conditions within the test), corrections can be dynamically instituted into the system and appropriately noted and documented for apprising researchers of the dynamics of the test being run.

Data gathering by the computer consists of the collection of data required for continuous in-line monitoring of test chemical effluent from each compartment. Sensors, preferably of the flow-through type, are disposed in-line with the outflow from each compartment, to thus detect, analyze and provide quantitative data regarding the test chemical effluent from each compartment.

Microprocessors can also serve to compute a physiologically-based pharmacokinetic (PBPK) model for a particular test chemical. These calculations may serve as the basis for setting the flow rates among compartments and excretion rates for the test chemical from the system. However, they may also serve as a theoretical estimate for the test chemical. At the conclusion of the experiment, predictions concerning the concentrations of test chemicals and metabolites made by the PBPK determination can be compared to the sensor data. Hard copy output compares the PBPK model with experimental results.

Figure 17A:
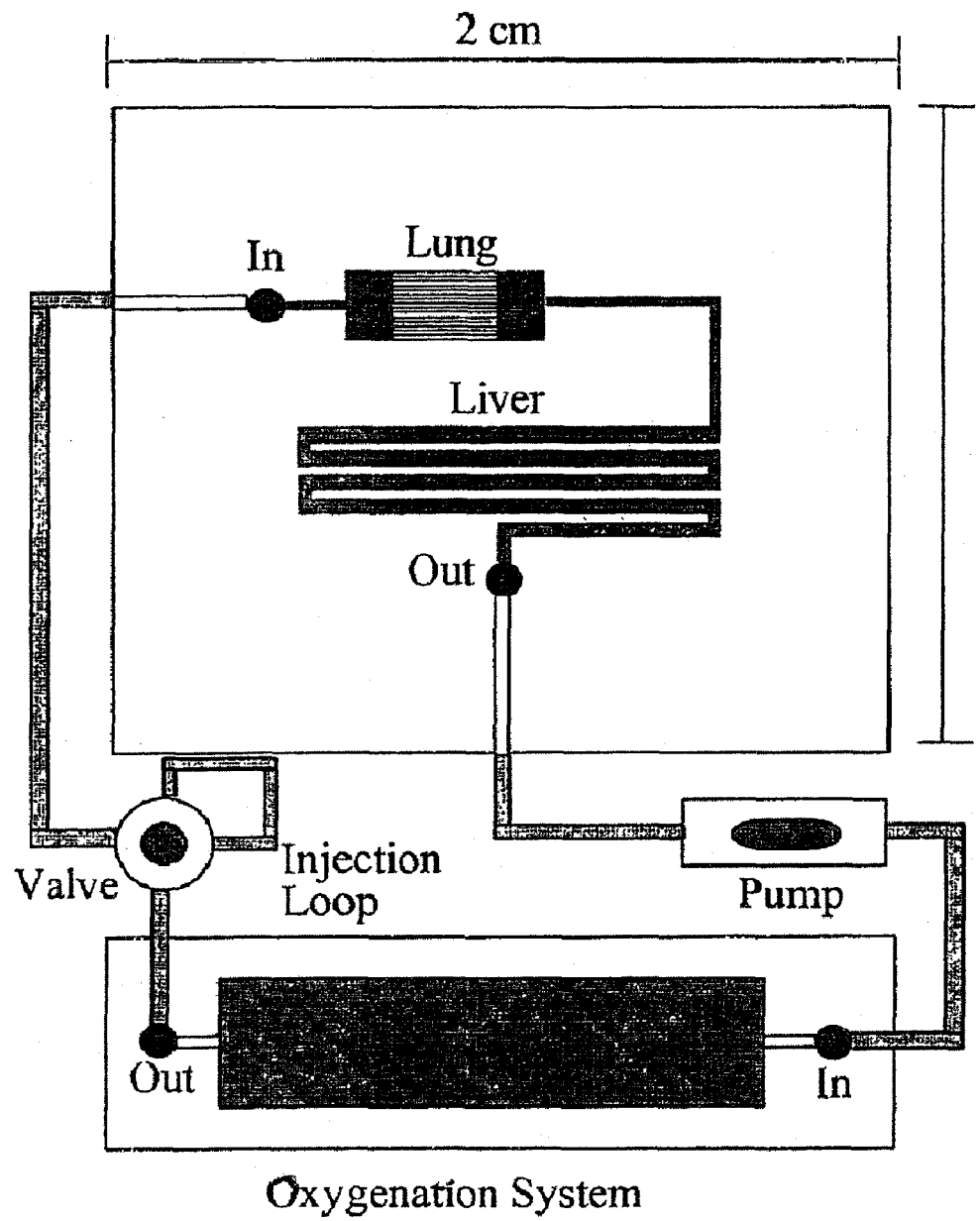
FIG. 17A depicts a "first generation" three compartment device.
Figure 17B:
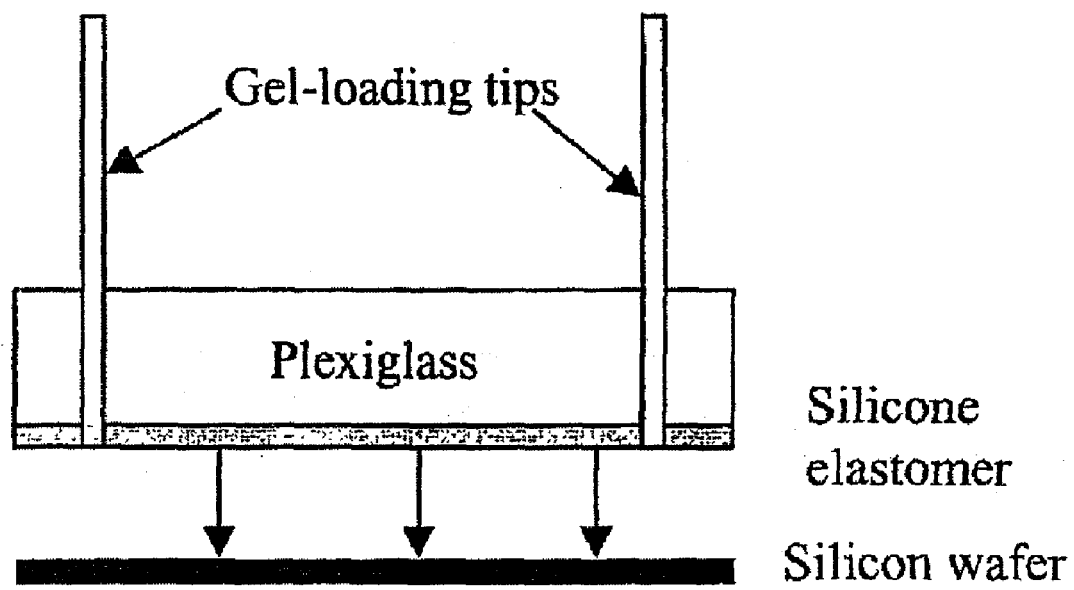
FIG. 17B shows a cross-sectional view of the device.

Several prototype CCA systems have been constructed and tested. FIG. 17A depicts a "first generation" three compartment device. The dimensions were as follows: wafer was 2 cm×2 cm; lung chamber had 20 channels (5 mm long) 40 µm×20 µm (w×d); liver chamber had 2 channels (100 mm long) 100 µm×20 µm (w×d). The first step in using this device is to inject the fluid using a syringe pump until all the channels filled up. Second, a peristaltic pump is used to recirculate the fluid. FIG. 17B shows a cross-sectional view of the device, demonstrating the fluidics of the system. It was found that 400 µm thick elastomer gave a better seal, and that plexiglass and gel-loading tips are much less fragile than other materials. This device had problems with a high pressure drop and leaks occurred at 90° bends.

Cell attachment studies were performed using this "first generation" device. L2 cells were placed in the lung chamber and H4IIE cells were placed in the liver chamber. Poly-D-lysine was adsorbed to the surface of the chambers to promote attachment of the cells within the channels. Unfortunately, cells attached outside the trenches, so different substrates were tested and surfaces were modified.

FIG. 18A depicts a "second generation" device. The dimensions were as follows: chip was 2 cm×2 cm; etching is 20 μm deep; lung chamber was 2 mm×2 mm (w×l); liver chamber was 7.5 mm×10 mm (w×l). The lung chamber contained 5 μm tall ridges to increase cell attachment (FIG. 18B), and the liver chamber contained 20 μm tall pillars to simulate percolation (FIG. 18C).

Figure 19:
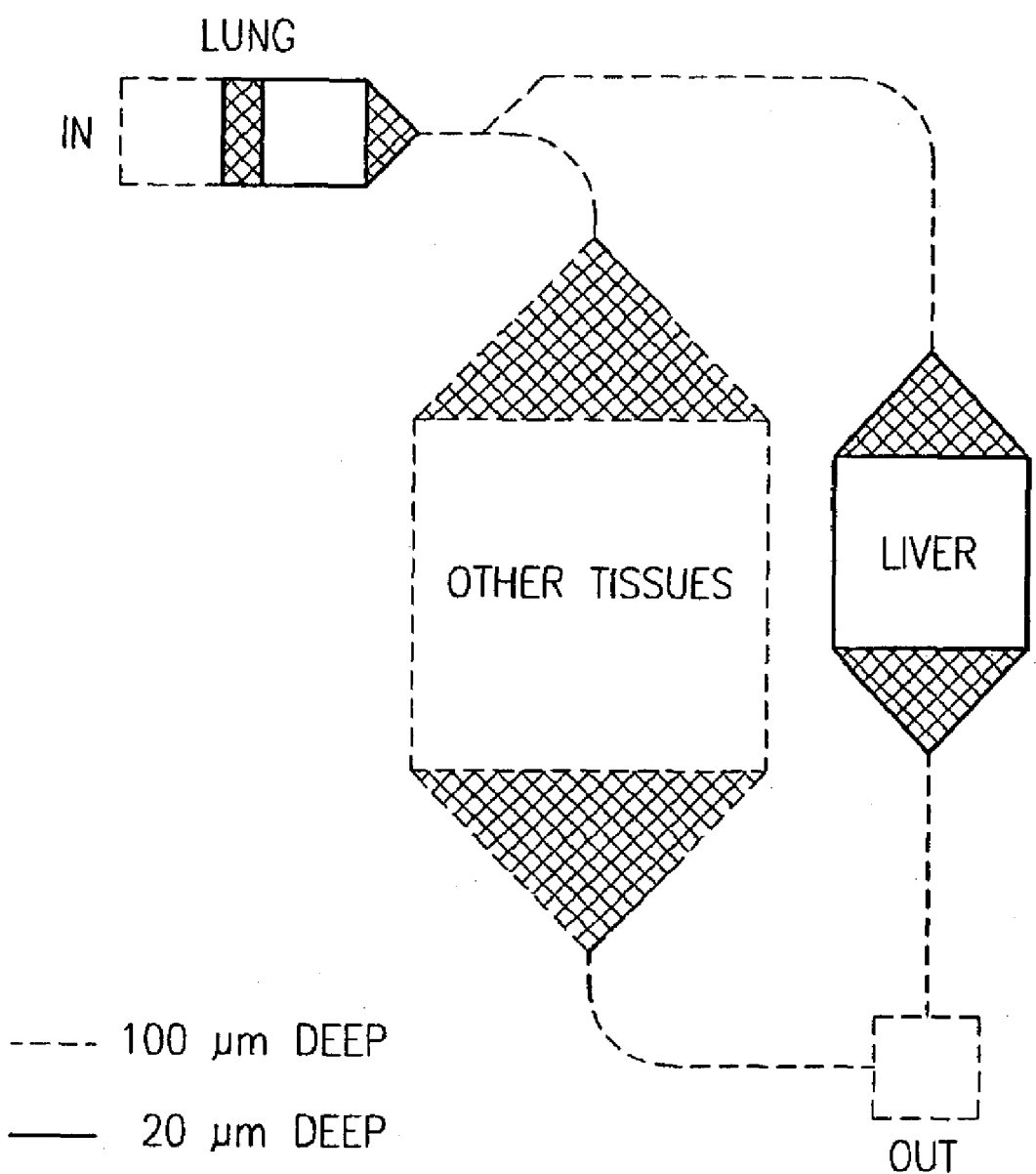
FIG. 19 depicts a "third generation" device.

FIG. 19 depicts a "third generation" device. The dimensions were as follows: chip was 2 cm×2 cm; lung chamber was 2 mm×2 mm (w×l); liver chamber was 3.7 mm×3.8 mm (w×l); and the "other tissue" chamber was 7 mm×7 mm (w×l). Fluid was split from the lung chamber, with 20% going to the liver and 80% to the other tissue chamber Portions of the chambers (dashed) are 100 μm deep to reduce pressure drops, and other portions (solid) are 20 μm deep to give realistic liquid-cell ratios.

Figure 20:
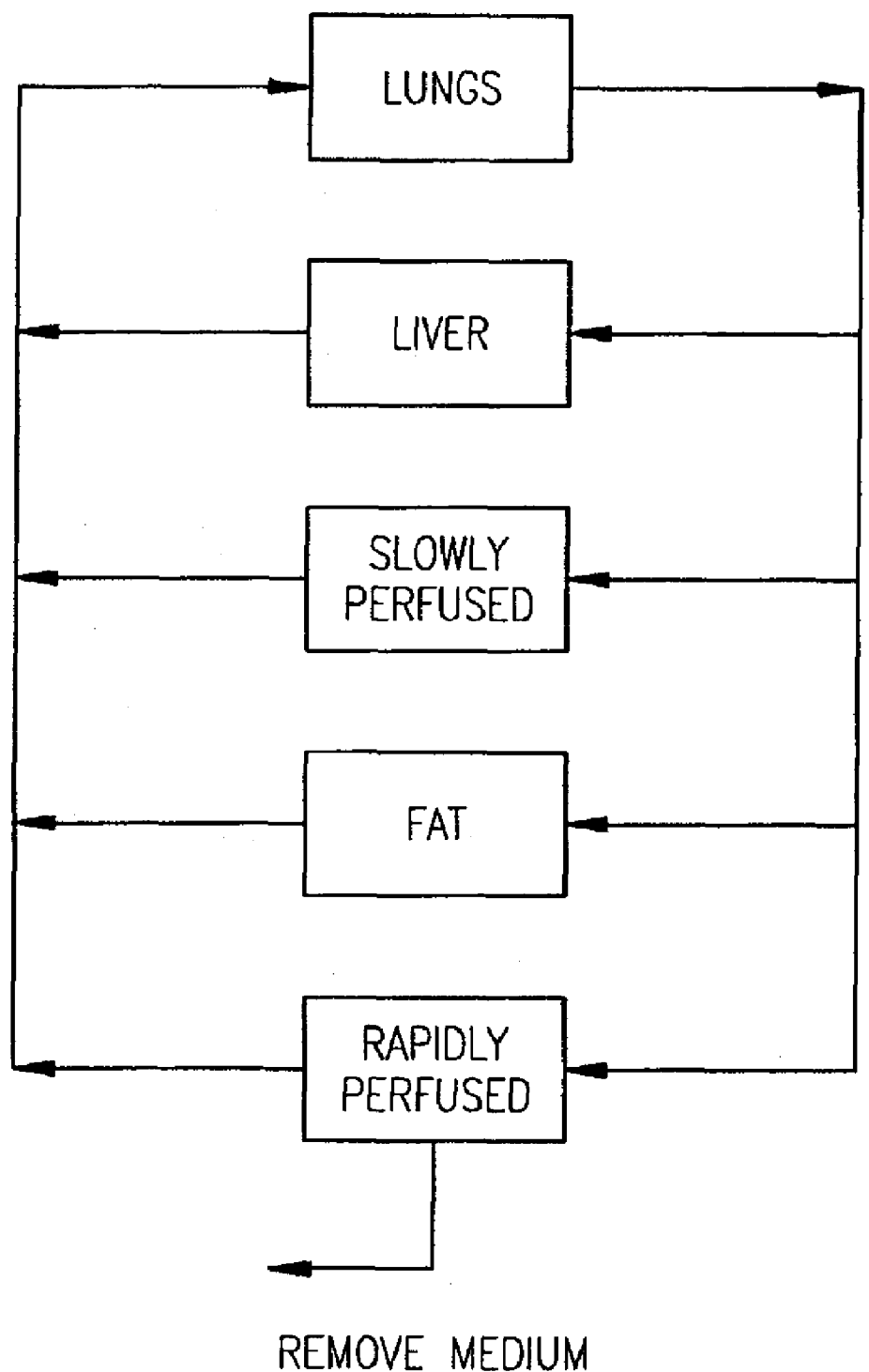
FIG. 20 is a flow diagram for a five compartment PBPK model CCA.
Figure 21:
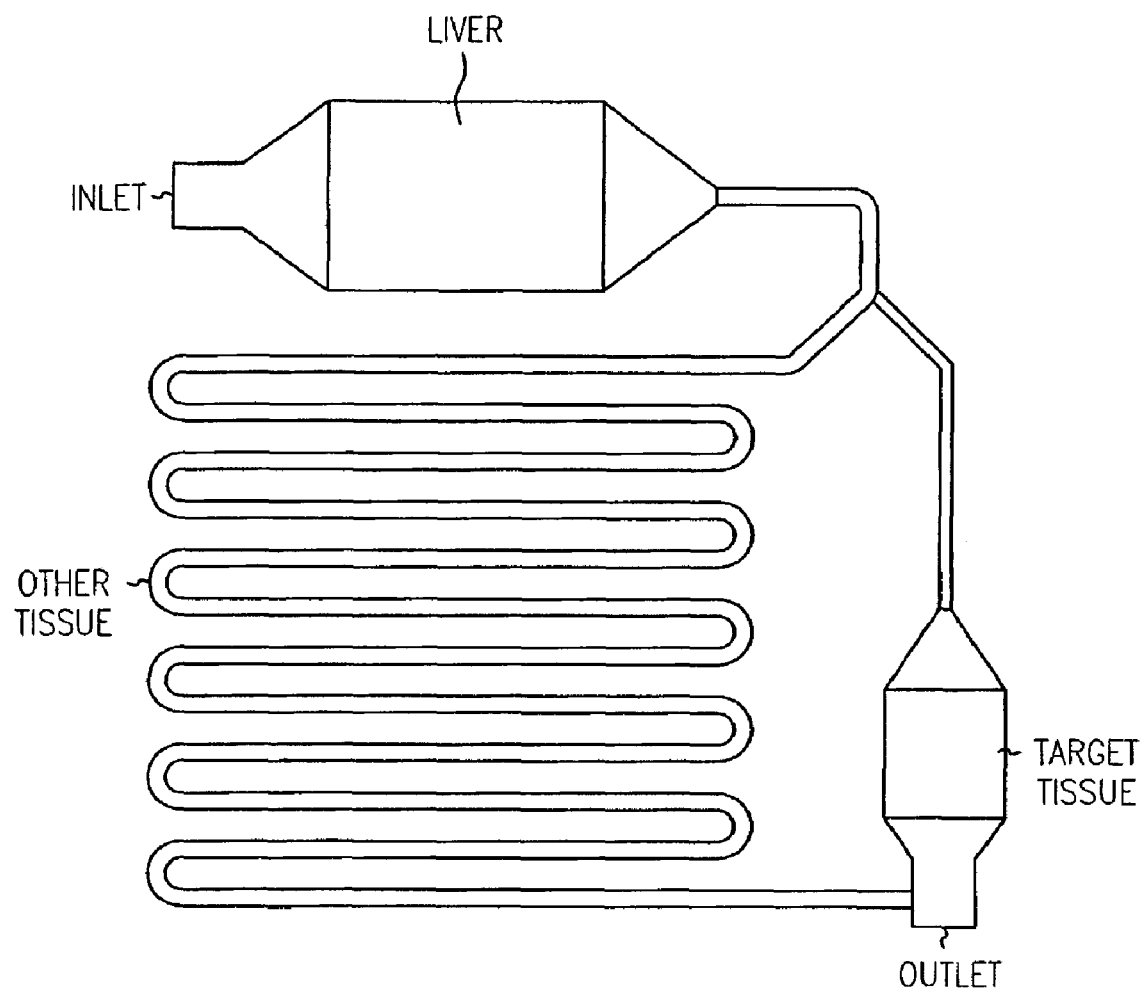
FIG. 21 depicts a human biochip prototype that contains compartments for lung, target tissues, and other tissues. The dimensions of the compartments and channels are as follows:
  Inlet: 1 mm by 1 mm
  Liver: 3.2 mm wide by 4 mm long
  Target Tissues: 2 mm wide by 2 mm long
  Other Tissues: 340 µµm wide by 110 mm long
  Outlet: 1 mm by 1 mm
  Channel Connecting Liver to Y connection: 440 µµm wide
  Channel from Y connection to Target Tissue: 100 µµm wide

FIG. 20 is a flow diagram for a five compartment PBPK model CCA. This device adds chambers for fat cells, a chamber for slowly perfused fluid and for rapidly perfused fluid. Such a device can be used for bioaccumulation studies, cytotoxicity studies and metabolic activities. Other devices can be developed with various permutations. For example, a diaphragm pump with gas exchange can be added, or an online biosensor, or a microelectromechanical (MEM) pump, or a biosensor and electronic interface. A device can be developed to mimic oral delivery of a pharmaceutical. Alternatively, a device can be developed to mimic the blood-brain barrier.

Fabrication

The cell culture device typically comprises an aggregation of separate elements, e.g., chambers, channels, inlet, or outlets, which when appropriately mated or joined together, form the culture device of the invention. Preferably the elements are provided in an integrated, "chip-based" format.

The fluidics of a device are appropriately scaled for the size of the device. In a chip-based format, the fluidic connections are "microfluidic," such a system contains a fluidic element, such as a passage, chamber or conduit that has at least one internal cross-sectional dimension, e.g., depth or width, of between about 0.1 μm and 500 μm. In the devices of the present invention, the channels between chambers typically include at least one microscale channel.

Typically, microfluidic devices comprise a top portion, a bottom portion, and an interior portion, wherein the interior portion substantially defines the channels and chambers of the device. In preferred aspects, the bottom portion will comprise a solid substrate that is substantially planar in structure, and which has at least one substantially flat upper surface. A variety of substrate materials may be employed as the bottom portion. Typically, because the devices are microfabricated, substrate materials will generally be selected based upon their compatibility with known microfabrication techniques, e.g., photolithography, thin-film deposition, wet chemical etching, reactive ion etching, inductively coupled plasma deep silicon etching, laser ablation, air abrasion techniques, injection molding, embossing, and other techniques.

The substrate materials of the present invention comprise polymeric materials, e.g., plastics, such as polystyrene, polymethylmethacrylate (PMMA), polycarbonate, polytetrafluoroethylene (TEFLON™), polyvinylchloride (PVC), polydimethylsiloxane (PDMS), polysulfone, and the like. Such substrates are readily manufactured from microfabricated masters, using well known molding techniques, such as injection molding, embossing or stamping, or by polymerizing the polymeric precursor material within the mold. Such polymeric substrate materials are preferred for their ease of manufacture, low cost and disposability, as well as their general inertness to most extreme reaction conditions. These polymeric materials may include treated surfaces, e.g., derivatized or coated surfaces, to enhance their utility in the system, e.g., provide enhanced fluid direction, cellular attachment or cellular segregation.

The channels and/or chambers of the microfluidic devices are typically fabricated into the upper surface of the substrate, or bottom portion, using the above described microfabrication techniques, as microscale grooves or indentations. The lower surface of the top portion of the microfluidic device, which top portion typically comprises a second planar substrate, is then overlaid upon and bonded to the surface of the bottom substrate, sealing the channels and/or chambers (the interior portion) of the device at the interface of these two components. Bonding of the top portion to the bottom portion may be carried out using a variety of known methods, depending upon the nature of the substrate material. For example, in the case of glass substrates, thermal bonding techniques may be used that employ elevated temperatures and pressure to bond the top portion of the device to the bottom portion. Polymeric substrates may be bonded using similar techniques, except that the temperatures used are generally lower to prevent excessive melting of the substrate material. Alternative methods may also be used to bond polymeric parts of the device together, including acoustic welding techniques, or the use of adhesives, e.g., UV curable adhesives, and the like.

The device will generally comprise a pump, such as a low flow rate peristaltic pump. A small bore flexible tubing would be attached to the outlet of the device, passing through the peristaltic pump and attached to the inlet of the device, thus forming a closed loop system. The pump generally operates at flow rates on the order of 1 μL/min. The pump system can be any fluid pump device, such as a diaphragm, and can be either integral to the CCA device (chip-based system) or a separate component as described above.

The device can be connected to or interfaced with a processor, which stores and/or analyzes the signal from each the biosensors. The processor in turn forwards the data to computer memory (either hard disk or RAM) from where it can be used by a software program to further analyze, print and/or display the results.

Description of Exemplary Embodiments

In the following detailed description of specific embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention.

Figure 1:
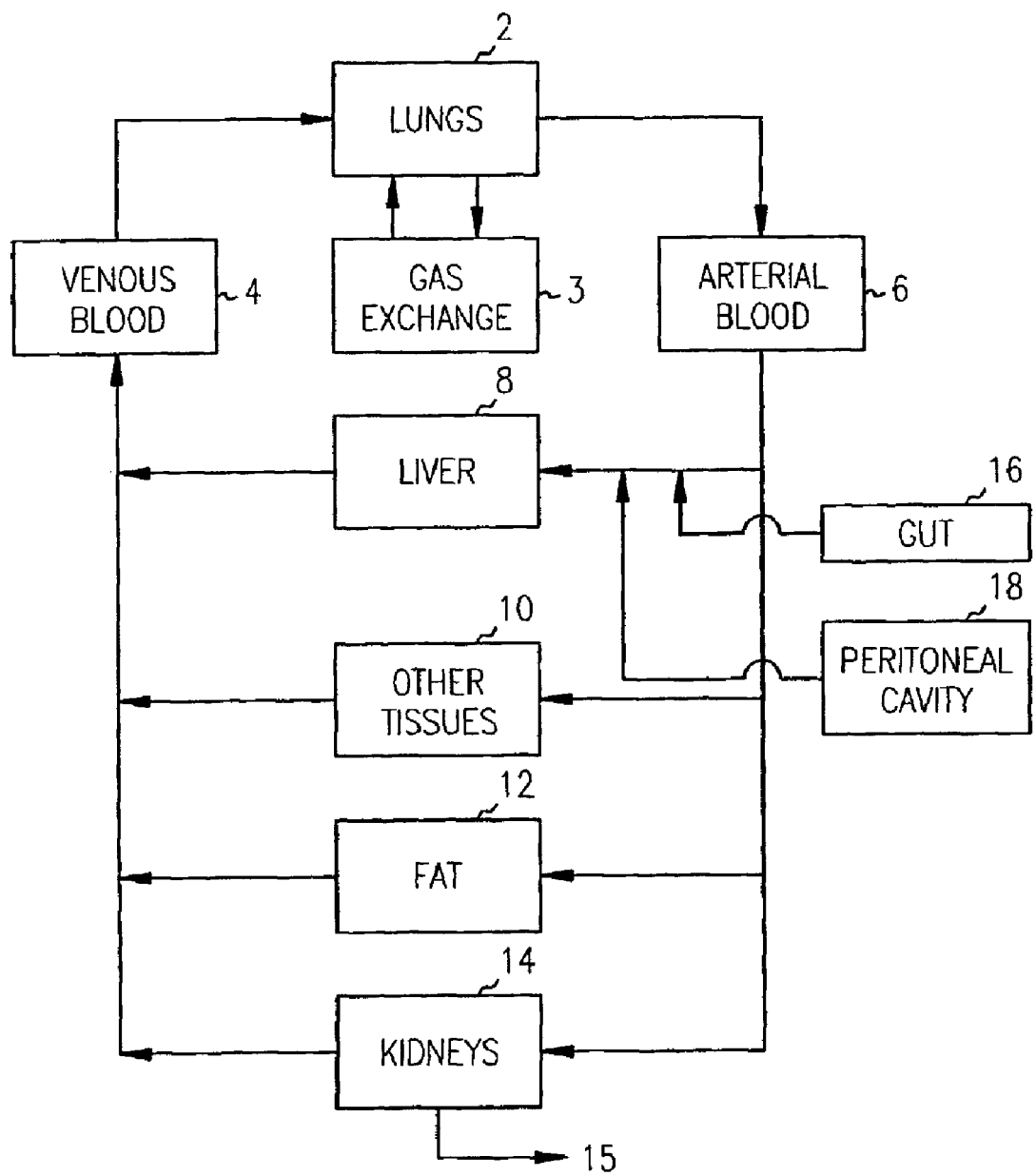
FIG. 1 is a block diagram of a system in accordance with the present invention.

FIG. 1 is a block diagram of an in vitro system in accordance with the present invention. Lung cell simulating chamber 102 receives oxygenated culture medium from gas exchange device 103. Such oxygenated medium is obtained by contacting culture medium with oxygen-containing gas so that the culture medium absorbs oxygen-containing gas and desorbs carbon dioxide-containing gas. The culture medium exiting lung cell simulating chamber 102 is analogous to arterial blood 106 in mammals. The oxygen-containing culture medium constituting arterial blood 106 is then supplied to liver simulating chamber 108, other tissue simulating chamber 110, fat simulating chamber 112, and kidney simulating chamber 114. The culture medium departing from liver simulating chamber 108, other tissue simulating chamber 110, fat simulating chamber 112, and kidney simulating chamber 114 is analogous to venous blood 104 in mammals. As shown in FIG. 1, the culture medium corresponding to venous blood 104 is returned to lung cell simulating chamber 102. The system of the present invention also includes gut simulating chamber 116 and peritoneal cavity simulating chamber 118, both of which constitute sites for introduction of test compounds. As in mammals, waste liquid 115 is withdrawn from kidney simulating chamber 114.

Figure 2:
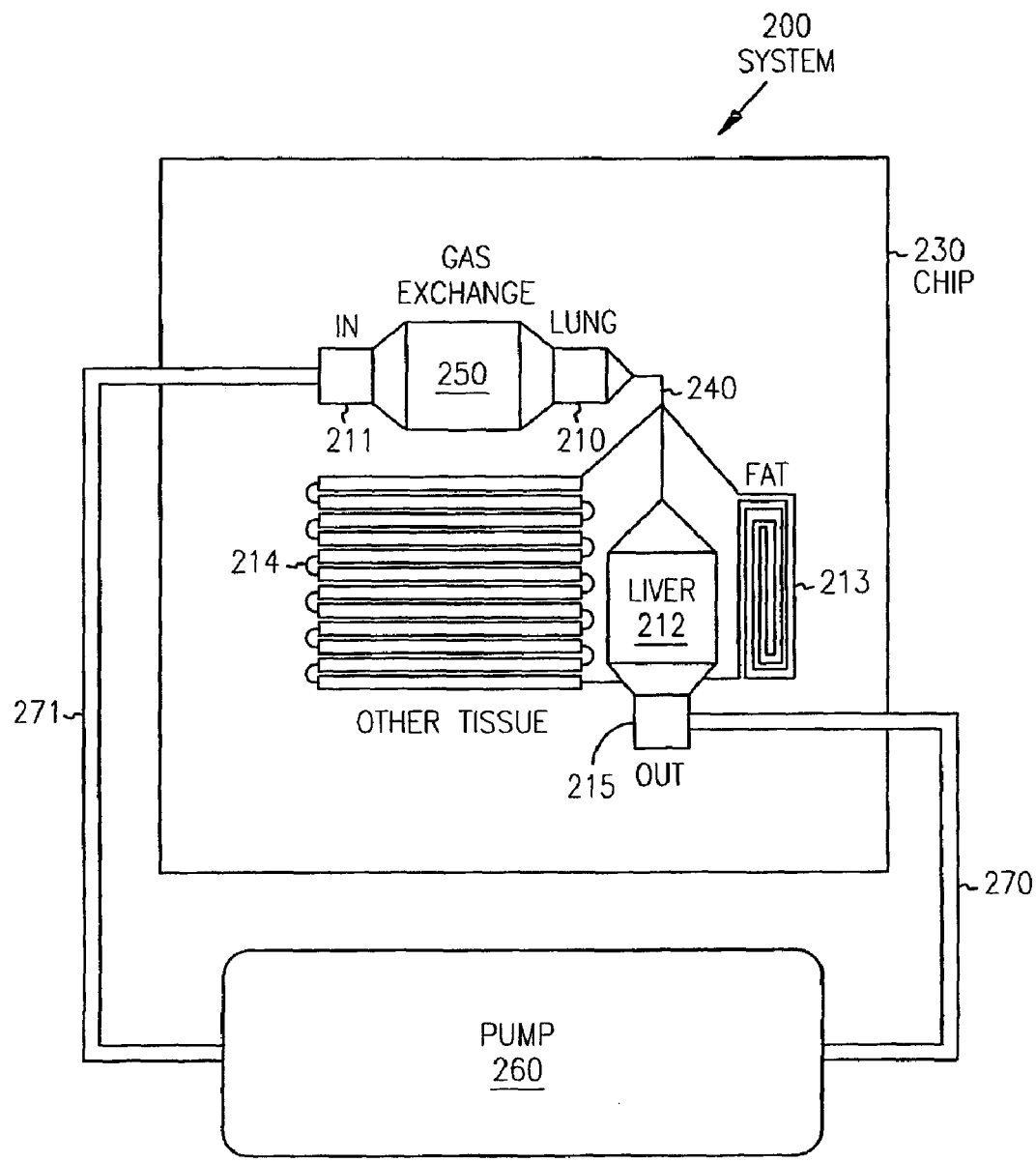
FIG. 2 is a simplified perspective view of one embodiment of the exterior of the system of the present invention.

FIG. 2 is a simplified schematic view of one embodiment of the system 200 of the present invention. The system 200 includes a lung cell culture chamber 210, a liver cell culture chamber 212, a fat cell culture chamber 213, an other tissues chamber 214, and a gas exchange chamber 250. The chambers 210, 212, 213, 214, and 250 are formed on a substrate of silicon that is commonly referred to as a chip 230. It should be noted that more than four cell culture chambers may be housed or formed on a single chip 230. A fluid path 240 connects the chambers 210, 212, 213, 214, and 250.

The chambers have an inlet 211 and an outlet 215. The inlet 211 is located at one end of the gas exchange chamber 250. The outlet 215 is located at one end of the liver cell culture chamber 212. The chambers 210, 212, 213, 214, and 250 and the fluid path 240 are located substantially between the inlet 211 and the outlet 215. The system includes a pump 260 for circulating the fluid in the system 200. A microtube 270 connects between the outlet 215 and the inlet side of the pump 260. A microtube 271 connects the outlet side of the pump 260 to the inlet 211. The cell culture chambers 210, 212, 213, 214 the gas exchange chamber 250, the fluid path 240, and the pump 260 form the system 200. The system may include additional cell culture chambers. One common cell culture chamber added is one simulating kidney.

Figure 3:
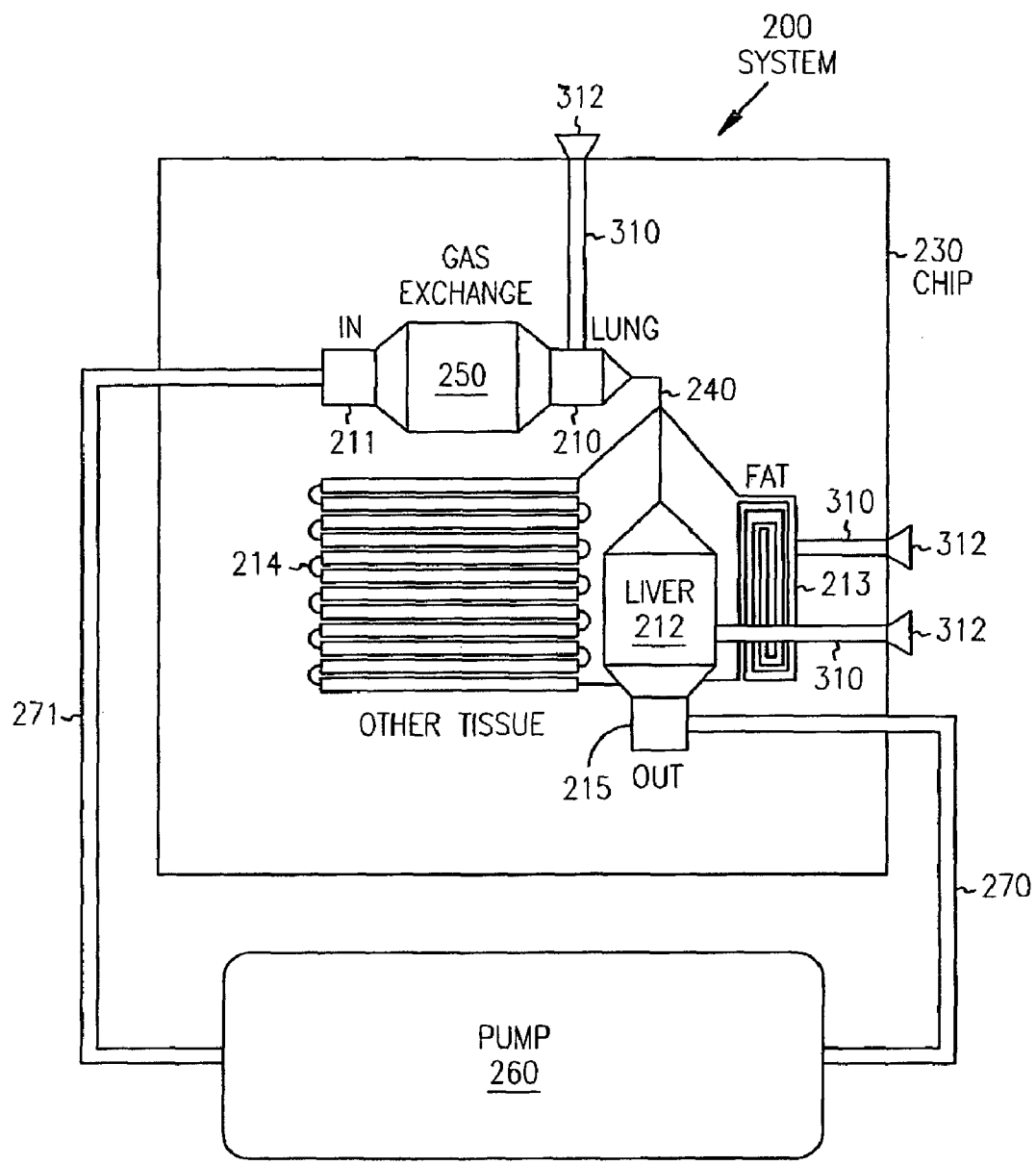
FIG. 3 is a detailed schematic view of another embodiment of the system of the present invention.

FIG. 3 is a schematic of another embodiment of the invention. In FIG. 3 a first signal path 310, a second signal path 320, and a third signal path 330 are provided on the chip 230. Signals for monitoring various aspects of each cell culture system 200 can be taken from the chip 230 and at specific locations on the chip 230 and moved to outputs off the chip 230. One example, the signal paths 310, 320, 330 on the chip 230 are integrated buried waveguides. The chip 230, in such an embodiment, could be made of silicon, glass or a polymer. The waveguide 310, 320, 330 would carry light to the edge of the chip where a transducer 312, 322, 332 would be located to transform the light signal to an electrical signal. The cells within the system 200 could then be monitored for fluorescence, luminescence, or absorption or all these properties to interrogate and monitor the cells within the system 200. Checking fluorescence requires a light source. The light source is used to interrogate the molecule and the signal carrier, such as a waveguide 310, 320, 330 or a fiber optic captures the signal and sends it off the chip 230. The signal carrier, 310, 320, 330 would direct light to a photodetector near the end of the signal carrying portion of the chip 310, 320, 330.

Figure 4:
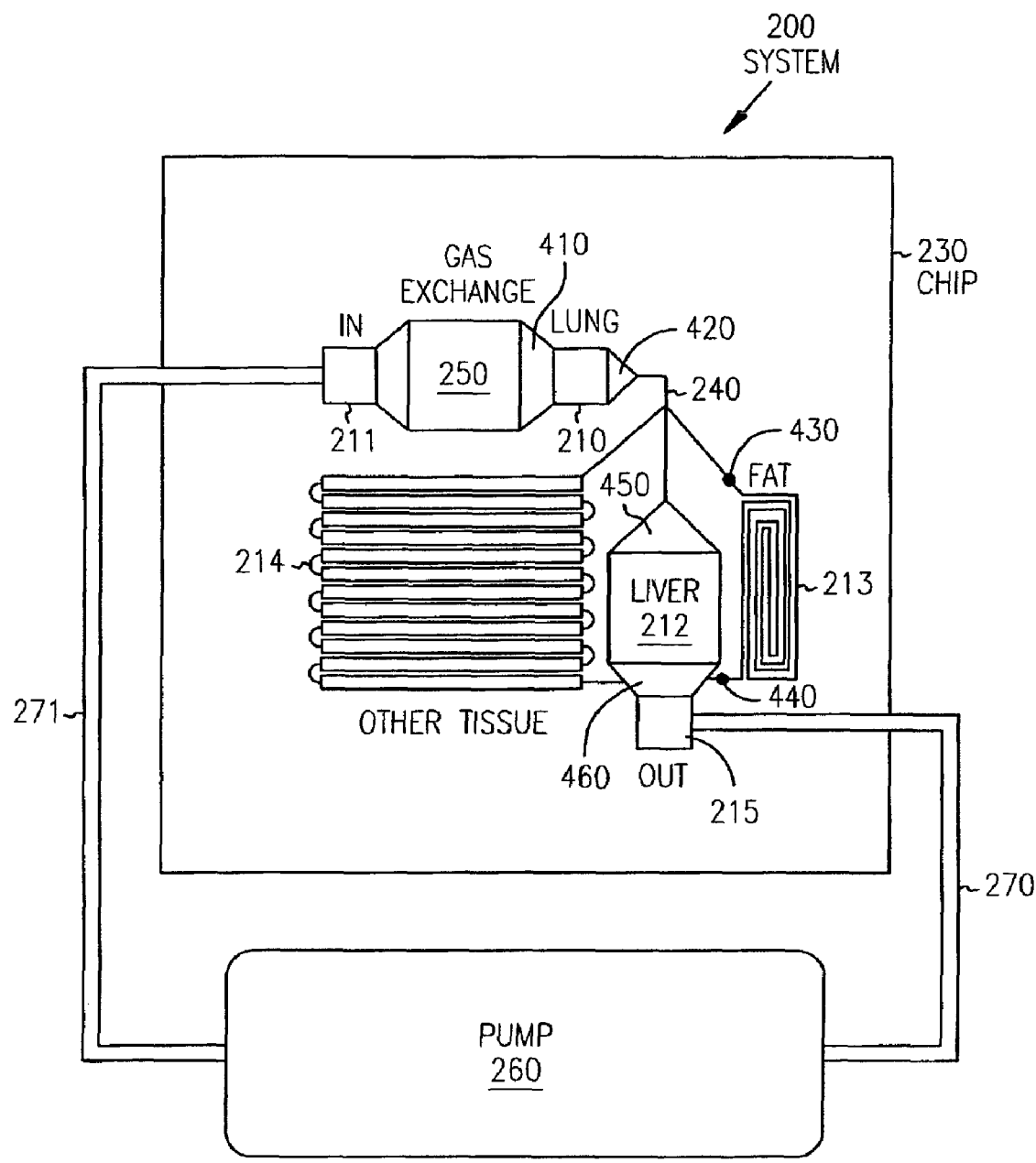
FIG. 4 is a schematic view of yet another embodiment of the system of the present invention.

FIG. 4 is a schematic view of another embodiment of the system 200 of the present invention. In this embodiment, biosensors 410, 420, 430, 440, 450, and 460 are positioned on the chip upstream and downstream of each of the cell culture chambers of the chip 230. The biosensors 410, 420, 430, 440, 450, 460 monitor the oxygen, carbon dioxide, and/or pH of the medium. These sensors allow monitoring of the system 200 and adjustment of gas levels as needed to maintain a healthy environment. In addition, if positioned just upstream and downstream of each cell compartment, biosensors provide useful information on cellular metabolism and viability.

Figure 5A:
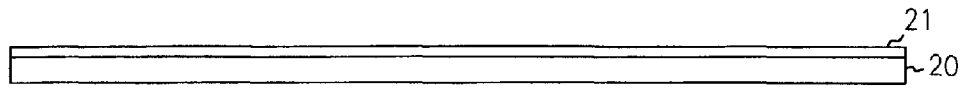
FIGS. 5A through 5G show steps used to fabricate a chip from plastic.
Figure 5B:
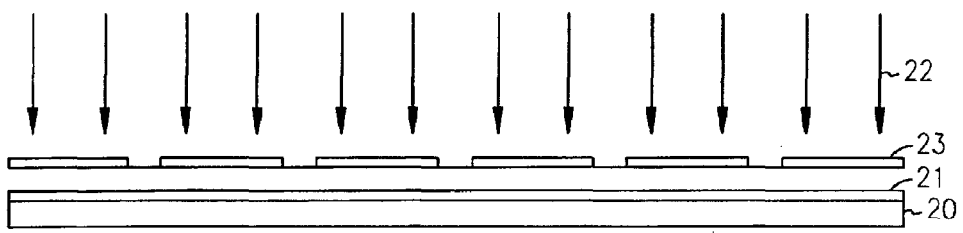
Figure 5C:
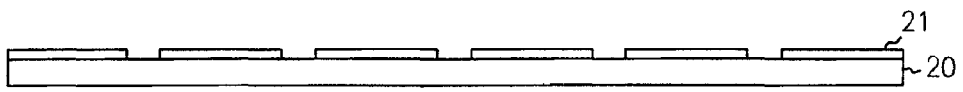
Figure 5D:
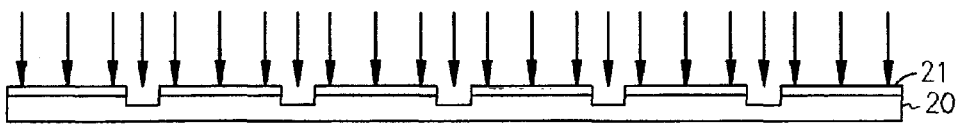
Figure 5E:
Figure 5F:
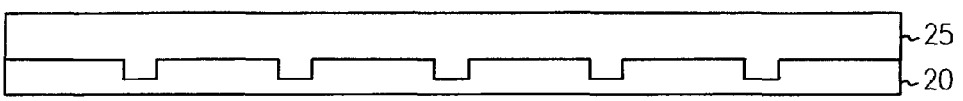
Figure 5G:
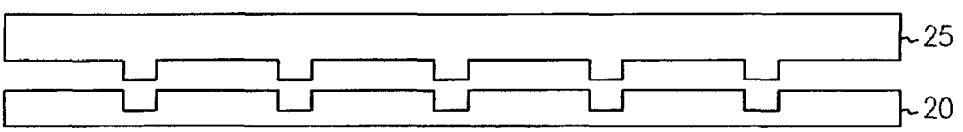

FIGS. 5A through 5G show steps used to fabricate a polymer-based disposable chip 230. A silicon wafer 20 is spin coated with a thin layer of photoresist 21 (FIG. 5A). The photoresist 21 is exposed to UV light 22 through a photomask 23 containing the desired features (FIG. 5B). The UV exposed photoresist 21 is developed away in an appropriate solvent thus exposing the silicon 20 (FIG. 5C). The silicon 20 is etched to a desired depth using an inductively coupled plasma etching system (FIG. 5D). The remaining photoresist is removed with an appropriate solvent (FIG. 5E). A very thin gold (or Ti) plating base 24 is deposited on the silicon substrate 20 creating a template for the electroplating process, as shown in FIG. 5E. The sample is immersed in a nickel sulfamate type plating bath and nickel 25 is electroplated onto the silicon template 20 until the nickel thickness is sufficient, with the gold acting as a conducting layer. The nickel master grows off the gold layer, and the gold becomes a part of the nickel master. This forms Ni features 25, shown in FIG. 5F. The plating rate, which is a function of plating current, template diameter and template thickness, is calibrated for about 45 nm/min. After fabrication, the features 25 are examined using a microscope to verify the feature dimensions. The resulting nickel features 25 must be uniform and have the desired shape. The nickel master 25 and the polymer substrate 26 are heated to just above the glass transition temperature of the polymer. The nickel master 25 and polymer 26 are brought into contact and the features of the nickel master 25 are embossed into the polymer substrate 26. The nickel master 25 is removed thus producing a polymer 26 containing the identical features of the original silicon wafer 20 (FIG. 5G).

Figure 6:
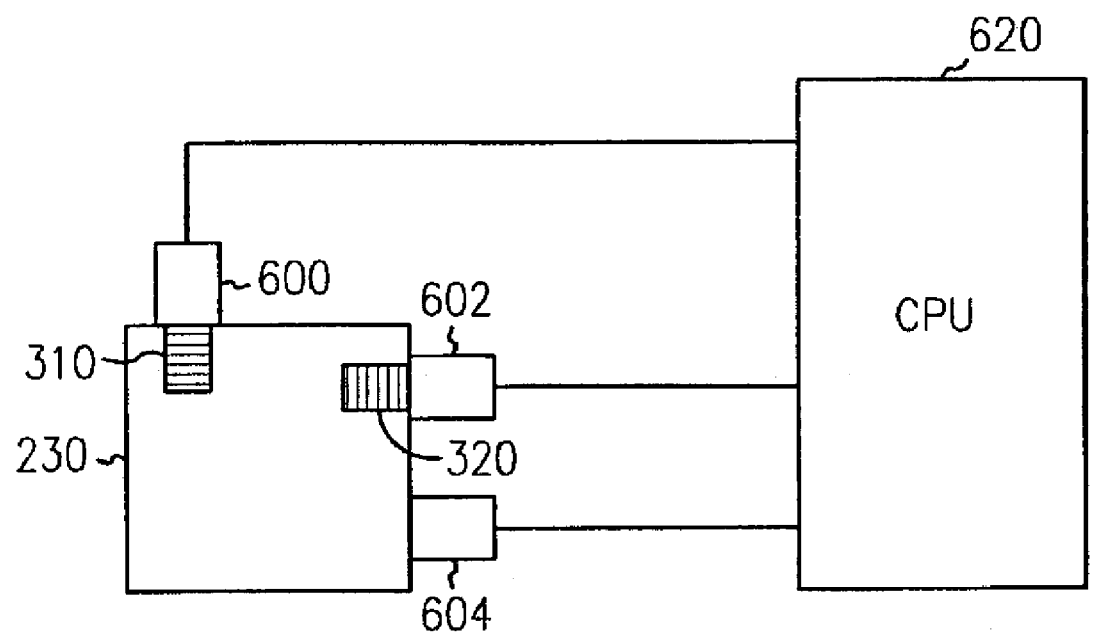
FIG. 6 is a schematic view of still another embodiment of the system of the present invention.

FIG. 6 is a schematic view of a third embodiment of the system 200 of the present invention. In this embodiment, biosensors 600, 602, 604 are positioned about the periphery of the chip 230. The biosensors 600, 602, 604 are used to further monitor the status of the cells of the system 200 created on the chip 230. Advantageously, by positioning the biosensors 600, 602, 604 about the periphery of the chip 230, the chip 230 could be made to be disposable with the least amount of cost. In other words, the biosensors 600, 602, 604 would not have to be thrown away with the chip 230. It should be noted that biosensors 600, 602, 604 may also be provided on board the disposable chip 230. This particular option would not be as cost effective since the biosensors 600, 602, 604 disposing the chip 230 also results in throwing away the biosensors 600, 602, 604. It is more cost effective when the biosensors 600, 602, 604 are positioned off the chip 230 since the biosensors 600, 602, 604 are reused rather than disposed of after each use. Each of the biosensors 600, 602, 604 is connected to the inputs of a computer 620.

Figure 7:
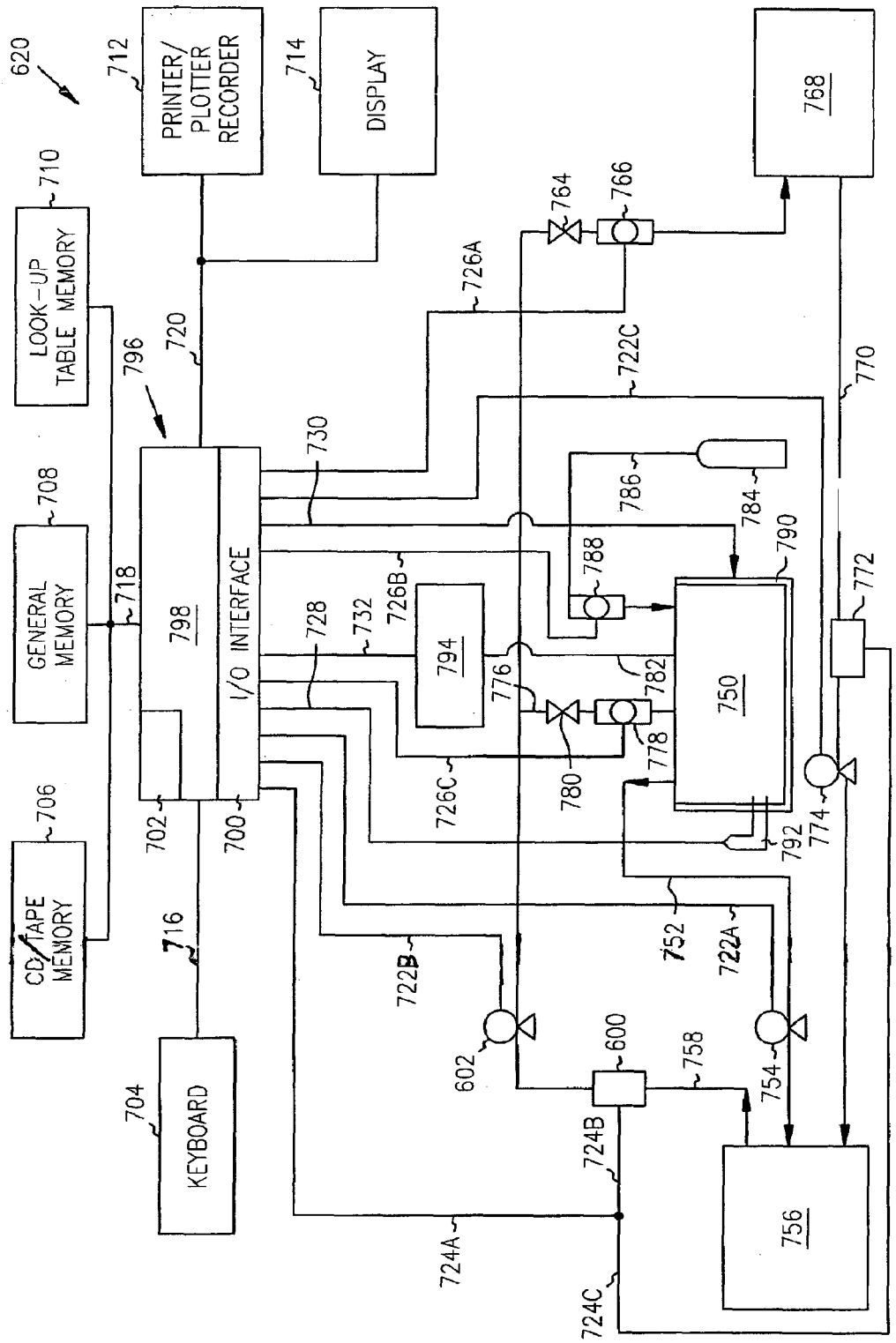
FIG. 7 is a schematic detailing a computer associated with the chips.

FIG. 7 is a schematic further detailing the computer 620. The computer 620 monitors and regulates operations of the system 200 of each chip 230. Computer 620 includes a microprocessor provided with input/output interface 700 and internal register/cache memory 702. As shown, microprocessor 798 interfaces to keyboard 704 through connection 716, to non-volatile storage memory 706, general purpose memory 708, and look-up tables 710 through connector 718, and to printer/plotter recorder 712 and display 714 through connector 720.

Non-volatile storage memory 706 may be in the form of a CD writeable memory, a magnetic tape memory, disk drive, or the like. Look-up tables 710 may physically comprise a portion of general purpose memory 708 that is set aside for storage of a set of mass balance equations applicable to various substances to be modeled in the system. These equations represent physiologically-based pharmacokinetic models for various biological/chemical substances in systems. Internal register/cache memory 702 and general purpose memory 708 contain a system program in the form of a plurality of program instructions and special data for automatically controlling virtually every function in the system 200 of each chip 230. The computer can also control and regulate the pump 260 associated with the system 200.

Fluid flow may also be provided as inputs to microprocessor 798 through input/output interface 700 from flow meters. This permits precise control over fluid flow rates within the system by adjustment of program commands that are transmitted to pumps 260 through pump control lines, respectively. For example, the flow rates may be set to 9.5 µL/min. in conduit 58, 2.5 µL/min. through flow meter 66, 7 µL/min. through flow meter 78, and 2.5 µL/min. in conduit 70. The temperature of culture medium in reservoir 50 may also be regulated by microprocessor 798, which receives, through input/output interface 700 and temperature indicator line 728, temperature measurements from temperature probe 792. In response to these signals, heater coil 790 is turned on and off by microprocessor 798 through input/output interface 700 and heater coil control line 730.

Biological and toxicological reactions/changes in cell culture chambers 210 and 212 are detected by sensors 600, 602 and 604, respectively, and communicated to microprocessor 798 through control lines as well as input/output interface 700. The sensors can be designed to represent test results in terms of specific values or ranges of wavelengths to represent test results.

Microprocessor 798 is also quite easily adaptable to include a program to provide the researcher with interactive control via keyboard 704. This permits, for example, directing the computer to specifically check on the conditions of any of the culture compartments at any given time.

A further option provided by the present invention is the ability to recall previously stored test results for similar experiments by recalling information from the CD/tape memory 706. Thus, memory 706 may be preprogrammed to hold historical data taken from published information, data gathered from previously run tests conducted with the system of the present invention or data derived from theoretical calculations. The provision of the CD/tape memory also permits the system to be used as an information researching tool. It can, for example, obtain the research data pertaining to a particular test chemical, or to a particular culture line, based on selection information inputted into microprocessor 798 via keyboard 704. By including or developing a large library of information in memory 706, researchers will be able to configure and plan test runs more intelligently.

Figure 8:
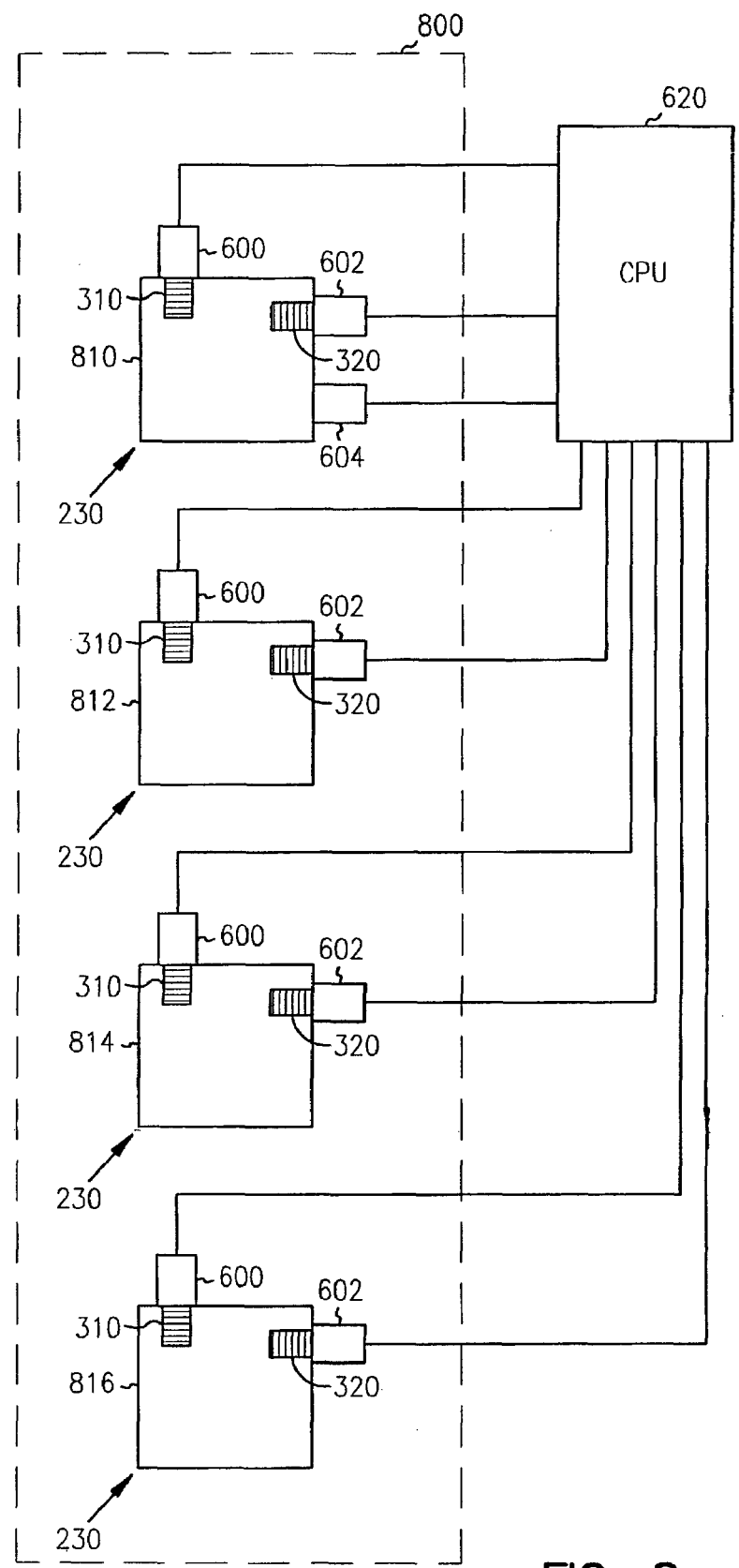
FIG. 8 is a schematic showing more than one chip located within a housing.

FIG. 8 is a schematic showing that more than one chip 230 can be housed within a single housing 800. The housing 800 can be an environmental chamber that maintains the same conditions for each of the chips 230 within the housing. The housing 800 includes a plurality of chip locations 810, 812, 814, 816. The outputs from each chip 230 or chip location 810, 812, 814, 816 is input to a computer 620. The computer 620 is then able to monitor the systems 200 from multiple chips 230 in real time.

Figure 9:
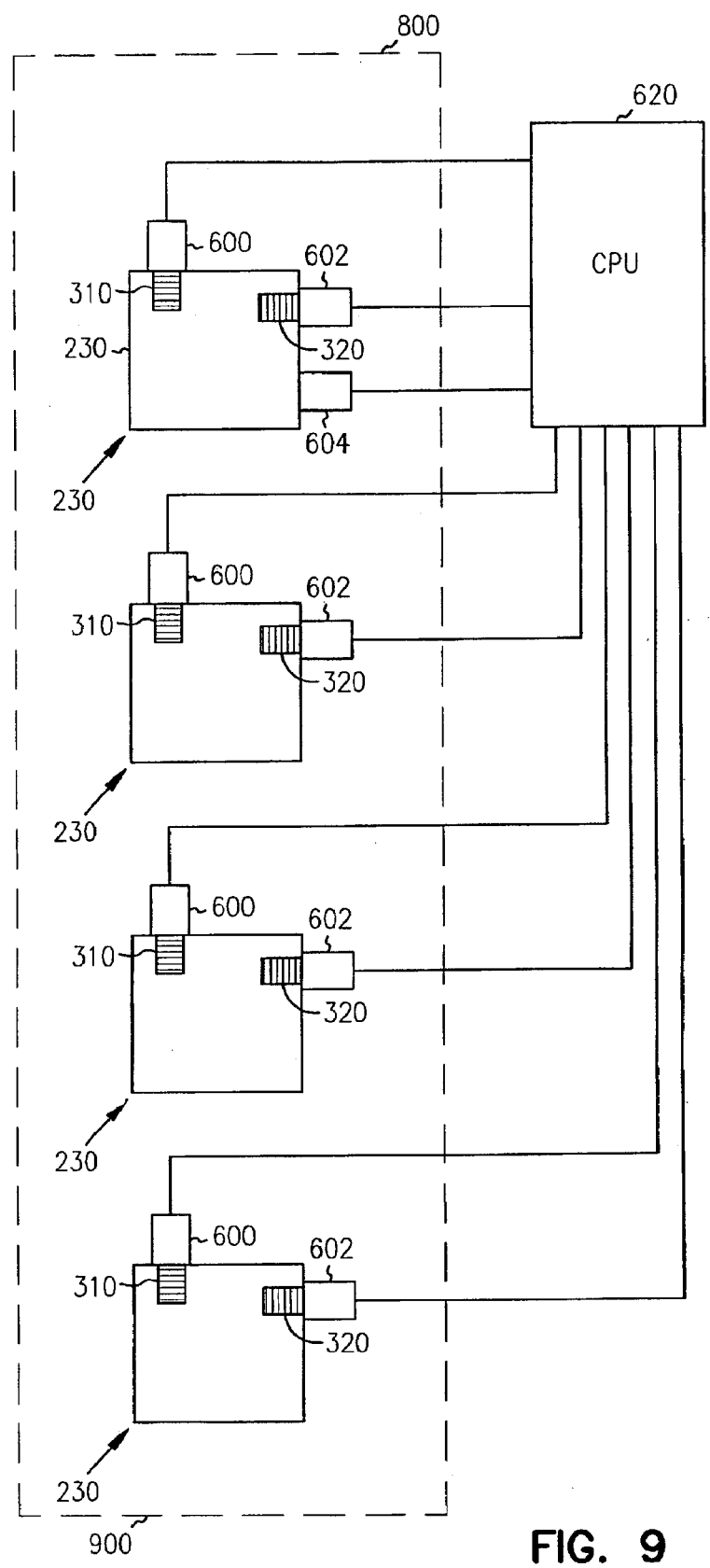
FIG. 9 is a schematic of a system that includes sets of chips from different housings.

FIG. 9 is a schematic showing that a test may include sets of chips 230 in different housings 800, 900. The outputs of each of the chips 230 can be monitored for changes in the environment, such as when temperature is slightly elevated, or the like. It is further contemplated that each of the chips in one housing may have the same cell culture thereon or that the chips 230 in the housing 800 may have chips interconnected to one another to form different portions of a mammal or interdependent organs within a housing.

The chips 230 discussed with respect to FIGS. 2-4 and 6-9 use two dimensional cell culture chambers 210, 212, 213, 214. Since three dimensional tissue culture constructs may be more authentic in their metabolism, yet another of the chip 1000 addresses the inclusion of three dimensional constructs. The following describes the creation of a microscale cell culture analogous device ("CCA"), which incorporates three dimensional tissues in a modular format. The CCA device or chip 1000 incorporates a flow over approach for lung cell chambers and a flow-through approach for other organs. The flow-through approach to CCA design is further discussed below.

Figure 10:
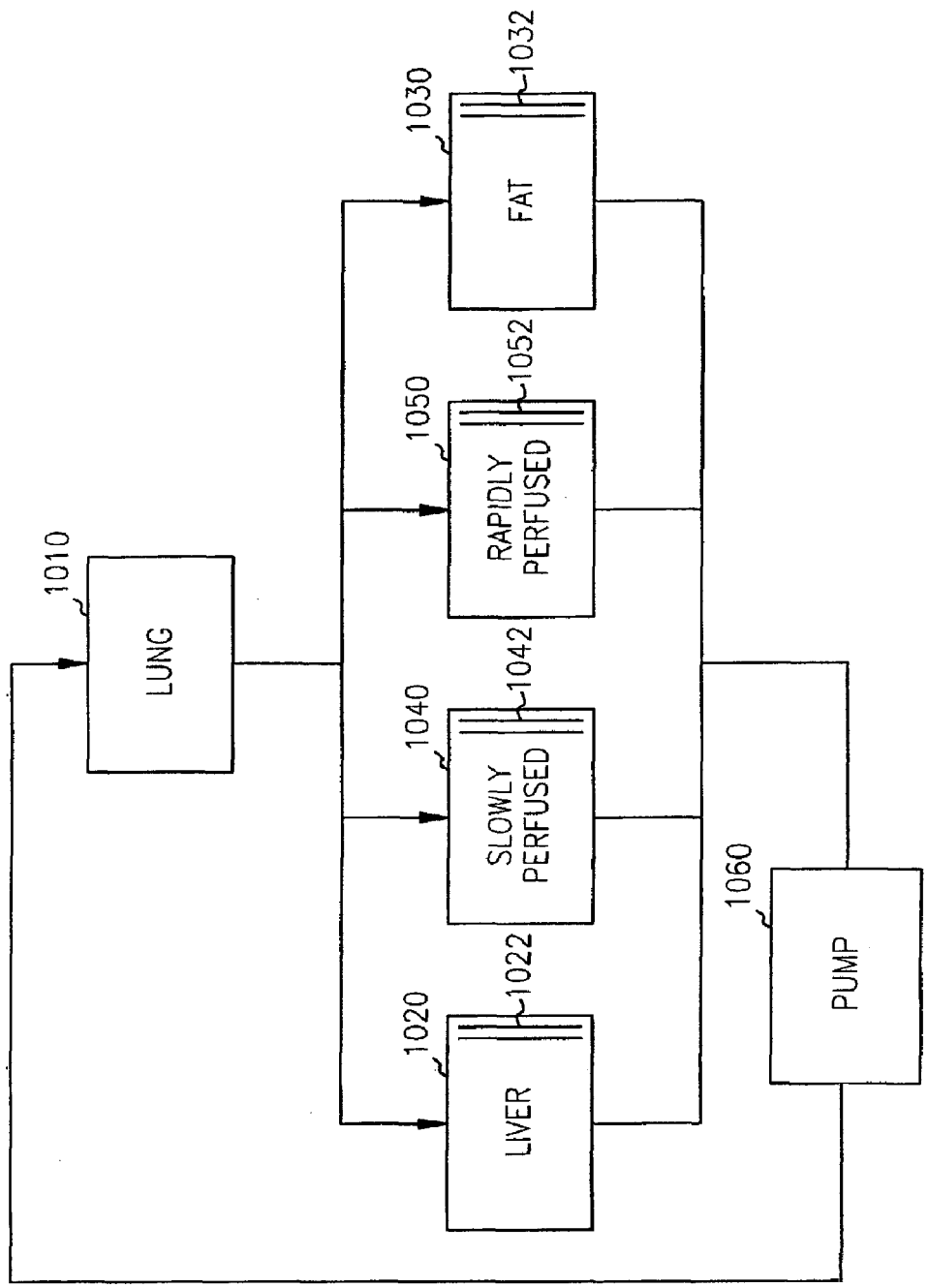
FIG. 10 is a schematic of yet another embodiment of a chip.

FIG. 10 shows a schematic and flow regime for a chip 1000. The chip 1000 includes four wells or tissue modules. The chip 1000 includes a lung well 1010, a liver well 1020, a fat well 1030, and a slowly perfused well 1040, and a rapidly perfused well 1050. Tubes are used to circulate a fluid through the chip 1000. A pump 1060 moves the fluid through the tubes. The lung well 1010 initially receives all of the flow. After the lung 1010, the fluid will partition into the four tissue modules. The liver module will get 25% of the flow, the fat module 9%, the slowly perfused module 15% and the rapidly perfused section 51%. Adjusting the geometry of the flow channels will partition the flow from the lung well 1010. The channels to each module will be of different lengths to equilibrate the pressure drops and balance the flow. After the fluid leaves the other tissues, it will be re-circulated back into the lung compartment via the pump 1060. Each of the wells or tissue modules 1020, 1030, 1040, 1050 holds tissue. The tissue is held in microscale tubes 1022, 1032, 1042, 1052 within the wells 1020, 1030, 1040, 1050. As shown in FIG. 10, there is only one microscale tube 1022, 1032, 1042, 1052 per well 1020, 1030, 1040, 1050. It should be noted that a plurality of microtubes may be placed in a well.

In operation, there are two methods that allow three dimensional tissue to be incorporated into a CCA device or chip 1000. Both methods involve the flow of inoculated medium through microscale tubes of polystyrene or glass. The cells under test adhere to the inside of the tubes and aggregate into three dimensional tissue. The tubes are collected, bundled and placed into wells on a chip 1000. Each well becomes an organ module that the aqueous drug will flow through to contact the tissue.

The first method to allow incorporation of three dimensional tissue involves a flow-through reactor strategy. Openings are formed in a silicon wafer and channeled medium is then passed through the openings. The silicon on the inside surface of the openings provided a scaffold for the cells and they aggregated into three dimensional tissue. To apply this technique to a polymer CCA 1000, the polymer tubes can either be treated with an adhesion protein or the cells can be cultured in serum-added medium. Both serum and an adhesion protein allow the cells to stick to the inside surface of the tube.

The second method involves culturing the cells in a HARV microgravity reactor. By scaffolding the tubes in the center of the rotating reactor, or by introducing free-floating tubes into the culture medium, the cells form three dimensional aggregates in some of the tubes. Due to the heightened activity of cells grown in microgravity, these tissue constructs have superior function compared to two dimensional tissue or the tissue formed in the method above. The tubes with tissue inside of them can be separated according to weight or density and placed on the device.

Figure 11:
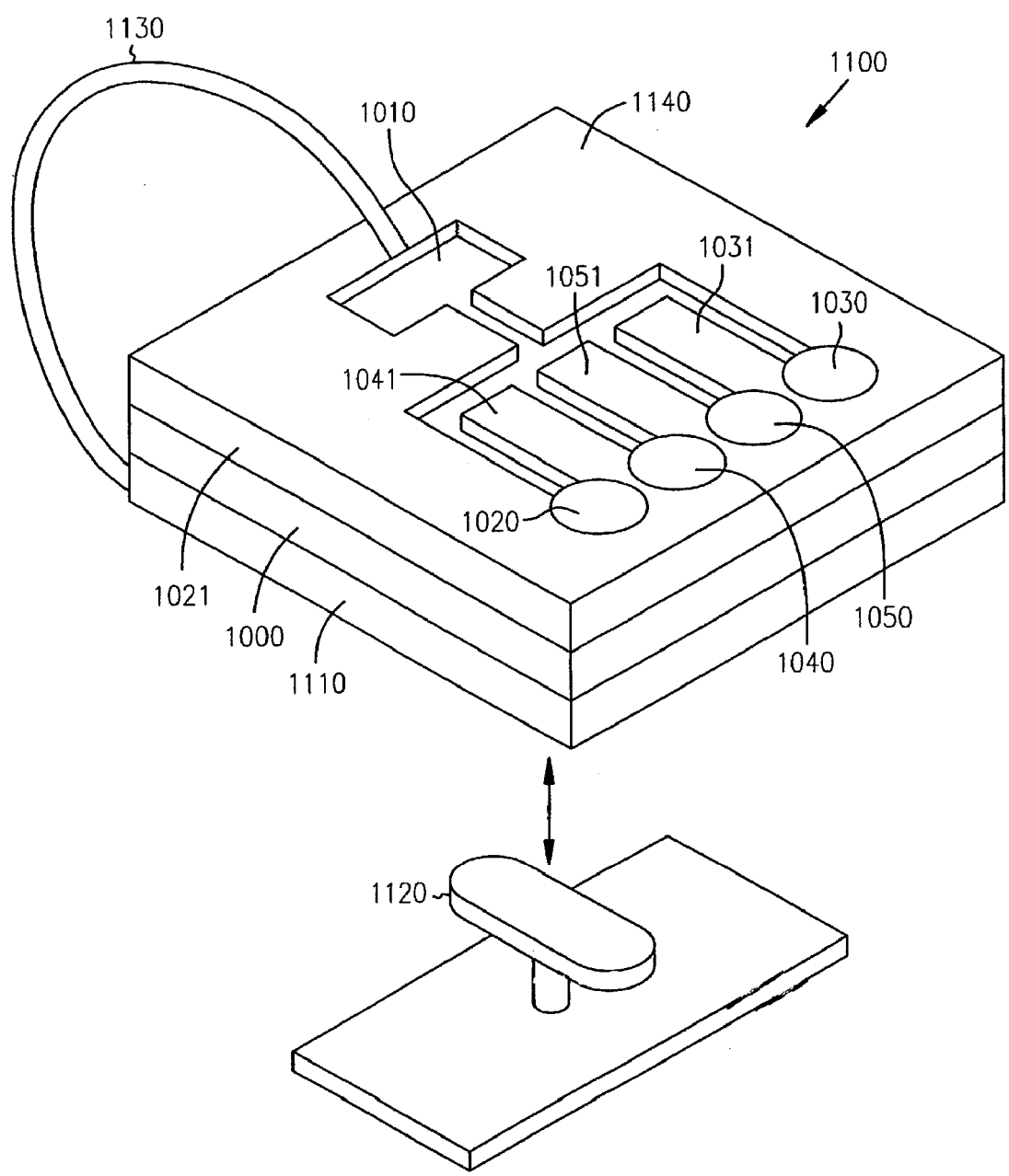
FIG. 11 is an isometric partially exploded view of a system.

FIG. 11 is a partially exploded isometric view of a cell culture analog device 1100 that incorporates chip 1000. The chip 1000 includes a lung cell culture area 1010 and a plurality of wells that are connected to the lung cell culture area 1010. The wells include a liver tissue well 1020, a fat tissue well 1030, a slowly perfused well 1040, and a rapidly perfused well 1050. Microscale tubes containing the various tissues fit within the well 1020, 1030, 1040, and 1050. Each well includes an output to an elastomeric bottom 1110 that is attached to the chip 1000. The elastomer 1110 is part of a pump. An actuator 1120 presses against the elastomer to produce a pumping action to move the fluid of the system 1100 or to circulate the fluid of the system 1100 from the wells back to the lung tissue module 1010 via a return line 1130. A glass layer is placed over the top of the chip to cover the lung tissue module 1010 and the various wells 1020, 1030, 1040, and 1050. It should be noted that the channels 1021, 1031, 1041, and 1051 are dimensioned to produce certain flow rates through the various wells 1020, 1030, 1040, and 1050. Rather than adjust the length and width of the various channels 1021, 1031, 1041, 1051 it is contemplated that other flow restrictors can be placed along the channel in order to provide for variability within the flow rates to the various wells 1020, 1030, 1040, and 1050. The glass top 1140 can be replaced with a membrane that flexes and plunger ball-type valves can be added so that the flows in the channels 1021, 1031, 1041, and 1051 can be regulated by other than the dimensions of the channel.

The chip 1100 can be made out of silicon but is more cost effective to make the chip 1000 out of polystyrene or some other suitable plastic. Each chip is first formed in silicon by conventional means. A nickel master is then formed from the silicon. In other words, the chip 1000 is manufactured by replica molding polystyrene and silicone elastomer on silicon and nickel masters. Of course, the first step in the manufacture of a polymer chip is to produce the chip on a silicon wafer. Initially, a layer of photoresist 1210 is placed on a silicon wafer 1200. A mask is placed over the photoresist 1210. The mask contains the pattern of a lung tissue culture area 1010. The mask allows UV light to pass to the photoresist to expose just the portion corresponding to the lung area 1010. The photoresist is then developed to produce an opening 1211, which corresponds to the lung tissue culture area 1010. The silicon wafer with the photoresist is then etched to produce the lung opening 1010 within the silicon wafer 1200. The photoresist 1210 is then removed from the silicon wafer 1200 leaving the silicon wafer with the lung well 1010. Another layer of photoresist 1220 is then placed onto the wafer 1200. A mask is placed over the wafer. The mask allows for exposure of the various wells or fluid channels including 1021, 1031, 1041, and 1051, which are used to connect the lung well 1010 with the various wells 1020, 1030, 1040, and 1050. The mask exposes the photoresist in the area of the fluid channel. The photoresist is then developed to remove the exposed photoresist corresponding to the fluid flow channels. The exposed area is then etched to a desired depth. Afterwards, the remaining photoresist 1220 is removed leaving a silicon wafer 1200 with a lung well 1010 and other wells 1020, 1030, 1040, and 1050. The next step is to apply yet a third layer of photoresist 1230. A mask is placed over the photoresist and the mask has openings corresponding to the various wells 1020, 1030, 1040, and 1050. The photoresist is masked and exposed to UV light to produce openings corresponding to the various wells. The photoresist is developed leaving the exposed silicon areas for wells 1020, 1030, 1040, and 1050.

The chip and the photoresist 1230 are then etched to produce the wells 4020, 1030, 1040, and 1050. The openings corresponding to the tissue modules 1020, 1030, 1040, 1050 is etched with plasma to a depth of approximately 750 micrometers. The openings are then wet etched another 250 micrometers with KOH to form a tapered end. The KOH will etch silicon along its crystallographic plane at an angle of 54.7 degrees. The photoresist is then removed and a silicon wafer has been formed from which the nickel master can be made.

Figure 12:
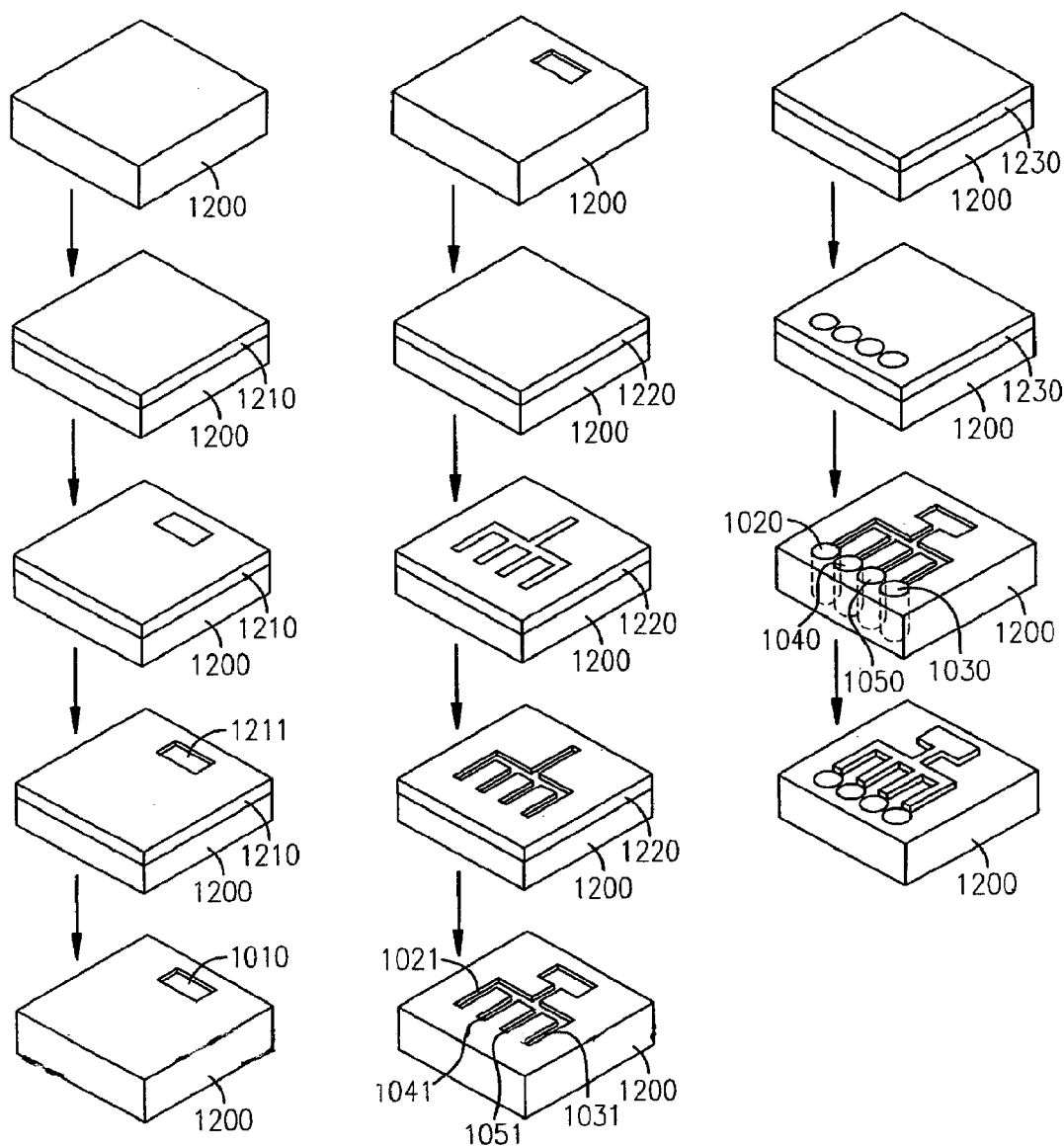
FIG. 12 is an isometric view of the steps for fabricating the chin associated with the system shown in FIG. 11.

Nickel is electroplated onto the silicon chip to create a nickel master 1250. The nickel master is then used to cast or emboss the polymer substrate 1000. For replica molding, the polymer is melted or solubilized in an appropriate solvent and poured onto the nickel master 1250 and solidifies in the same shape as the initial silicon chip. For embossing refer to FIG. 5. The polymer chip 1000 is then mounted on a silicone elastomer trough 1110. The polymer and silicone are self-sealing so the layers will form a single unit. A pneumatic actuator 1120 is put below the chip to pump fluid collected from the various tissue modules 1020, 1030, 1040, 1050. Every second, the trough will fill up with 0.032 microliters of fluid. The actuator will then push up on the silicone and cause the fluid to escape through the microtubes back to the lung compartment 1010. The elastomeric trough 1110 and the actuator 1120 form the pump 260 (shown in FIG. 12). The elastomer-coated polymethylmethacrylate (PLEXIGLAS™) 1140 is then sealed to the top of the wafer or chip 1000.

To balance the pressure pull created as the silicone fills up with liquid, the polymethylmethacrylate (PLEXIGLAS™) over the lung cell compartment 1010 is removed and replaced with a silicone membrane. This membrane rises and falls in response to the action of the silicone pump and keeps the pressure in the device balanced. The various microscale tubes are placed into the wells prior to placing the elastomer-coated polymethylmethacrylate (PLEXIGLAS™) over the chip 1000. A machine for handling the microtubes includes an adhesive arm that lowers and collects a specific number of tissue-laden tubes. The machine transports the tubes to the device and tightly packs the tubes into the respective module wells 1020, 1030, 1040, 1050. The tight packing allows the force of friction to keep the tubes in place regardless of any agitation to the cell culture analog device. This minimizes leakage of fluid flow around the tubes in the respective wells 1020, 1030, 1040, 1050. Even with a tight fit, approximately 5-10% of the fluid flow circumvents the tubes and flows directly to the silicone base or elastomer trough 1110.

Figure 13:
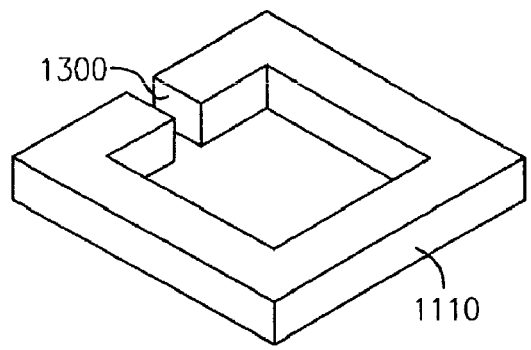
FIG. 13 is an isometric view of a single trough elastomeric portion of a pump associated with the system shown in FIG. 11.

FIG. 13 shows the elastomer trough. The elastomer trough is a piece of silicone elastomer with an essentially rectangular opening therein. The rectangular opening acts as a fluid reservoir for the fluids coming from the wells 1020, 1030, 1040, and 1050. The elastomer trough 1110 has an opening in one side designated by reference numeral 1300. The return line 1130 has one end that attaches to the opening 1300 in the elastomer trough 1110 and another end that attaches to the lung well 1010 of the chip 1000.

Figure 14:
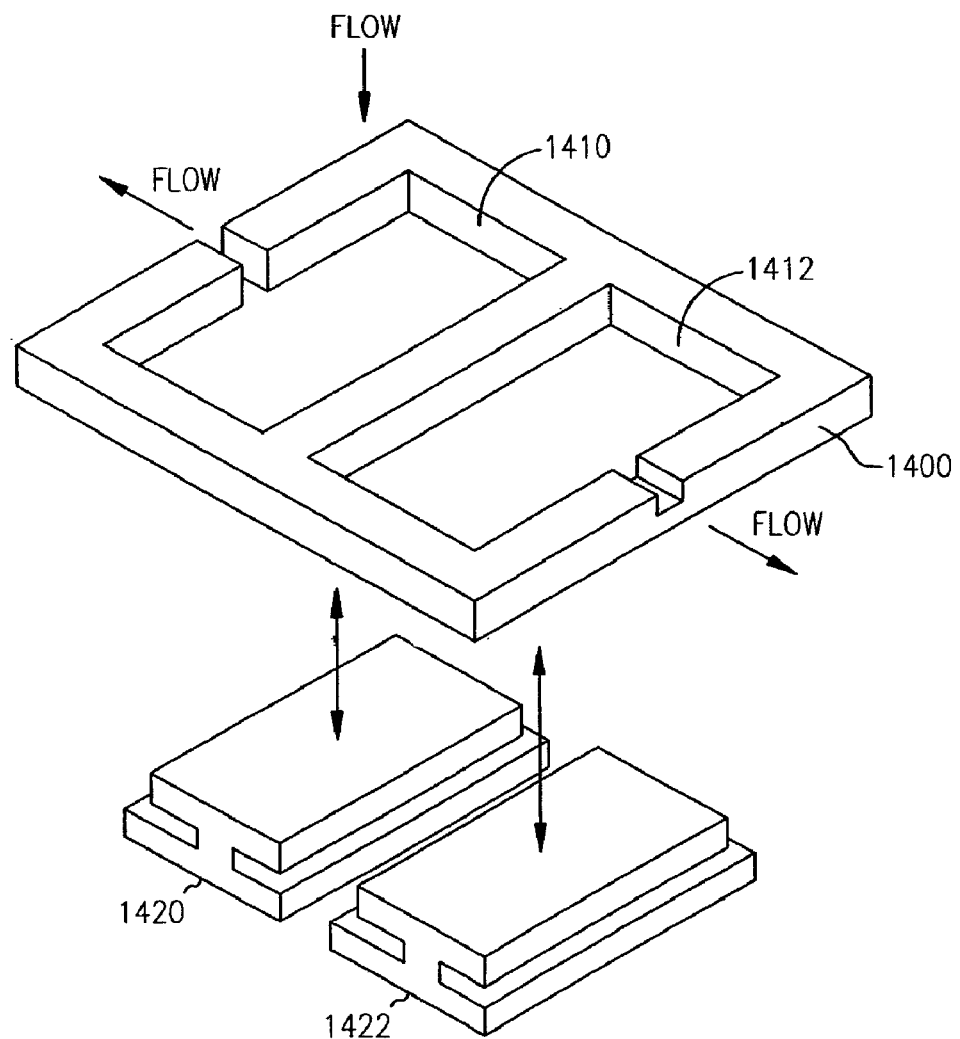
FIG. 14 is an isometric view of a multiple trough elastomeric portion of a pump.

In yet another embodiment, the elastomer trough 1110 is replaced with a silicone elastomer pump 1400, which is shown in FIG. 14. The silicone elastomer pump 1400 is designed to more accurately reproduce the circulatory system flow on the chip 1000 and throughout the system depicted by reference numeral 1100. The pump 1400 includes a first pulmonary chamber 1410 and a second system chamber 1412, which are actuated by separate actuators 1420 and 1422. With the multiple chambers 1410 and 1412 a more physiologically realistic pumping pattern is created with the multi-trough elastomeric base on the bottom of the chip 1000. By creating the multiple chambers 1410 and 1412 in the silicone elastomer trough 1400 by having actuators that push up on the section of the base at specific time intervals, the pumping action of a heart is replicated.

Figure 28A:
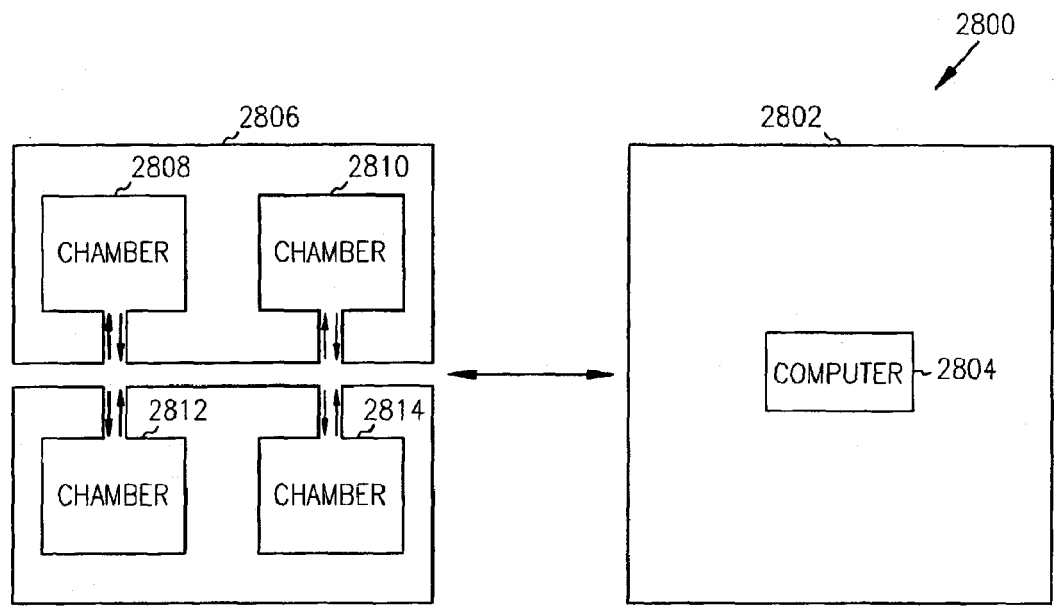
FIG. 28A is a block-diagram view illustrating a system for controlling a microscale culture device, according to one embodiment of the present invention.

FIG. 28A is a block-diagram view illustrating a system for controlling a microscale culture device, according to one embodiment of the present invention. In this embodiment, the system 2800 includes a first microscale culture device 2806 coupled to a control instrument 2802. The first microscale culture device 2806 includes a number of microscale chambers (2808, 2810, 2812, and 2814) with geometries that simulate a number of in vivo interactions with a culture medium, wherein each chamber includes an inlet and an outlet for flow of the culture medium, and a microfluidic channel interconnecting the chambers. The control instrument 2802 includes a computer 2804 to acquire data from, and control pharmacokinetic parameters of, the first microscale culture device 2806.

In another embodiment, the first microscale culture device 2806 is formed on a computerized chip. The first microscale culture device 2806 further includes one or more sensors coupled to the control instrument 2802 for measuring physiological events in the chambers. The sensors include one or more biosensors that monitor the oxygen, carbon dioxide, or pH of the culture medium. The control instrument 2802 holds the first microscale culture device 2806, and seals a top of the first microscale culture device 2806 to establish the microfluidic channel. The control instrument 2802 provides the microfluid interconnects, so that microfluid flows into and out of the device. In another implementation, the computer 2804 controls a pharmacokinetic parameter selected from a group consisting of group pump speed, temperature, length of experiment, and frequency of data acquisition of the first microscale culture device 2806. In one implementation, the computer 2804 provides a set-up screen so that an operator may also manually specify pump speed, device temperature, length of experiment, and frequency of data acquisition (e.g., every fifteen minutes). In another implementation, the computer 2804 controls a pharmacokinetic parameter selected from a group consisting of flow rate, chamber geometry, and number of cells in the first microscale culture device 2806. In this implementation, the system 2800 provides more rapid and more sensitive responses as compared to whole animal studies and traditional tissue culture studies. By controlling parameters, the system 2800 is no longer physiologically-based. In another implementation, the computer 2804 further controls one or more pumps in the first microscale culture device 2806 to create culture medium residence times in the chambers (2808, 2810, 2812, and 2814) comparable to those encountered in the living body. In another implementation, the computer 2804 further controls one or more valves distributed along the microfluidic channel in a manner that is consistent with a pharmacokinetic parameter value associated with a simulated part of a living body.

In another embodiment, the system 2800 further includes a second microscale culture device having a number of microscale chambers with geometries that simulate a number of in vivo interactions with a culture medium, wherein each chamber includes an inlet and an outlet for flow of the culture medium, and a microfluidic channel interconnecting the chambers. The control instrument 2802 is coupled to the second microscale culture device.

Figure 28B:
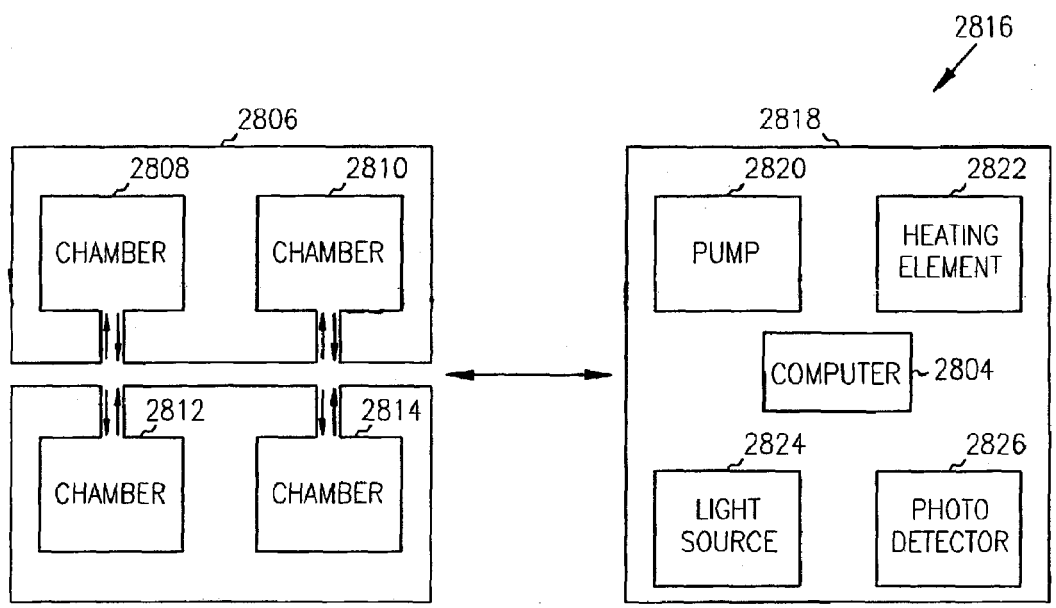
FIG. 28B is a block-diagram view illustrating a system for controlling a microscale culture device, according to another embodiment of the present invention.

FIG. 28B is a block-diagram view illustrating another embodiment of a system for controlling a microscale culture device. In this embodiment, the system 2816 includes the first microscale culture device 2806 coupled to a control instrument 2818. The control instrument 2818 includes the computer 2804, a pump 2820 to control circulation of microfluid in the microfluidic channel of the first microscale culture device 2806, a heating element 2822 to control the temperature of the first microscale culture device 2806, a light source 2824, and a photodetector 2826 to detect fluorescent emissions from cell compartments within the first microscale culture device 2806. In one implementation, the computer 2804 records data for fluorescent intensity using a measuring instrument of a type that is selected from a group consisting of calorimetric, fluorometric, luminescent, and radiometric. In another implementation, the heating element 2822 maintains the first microscale culture device 2806 at a temperature of thirty-seven degrees Celsius.

Figure 29:
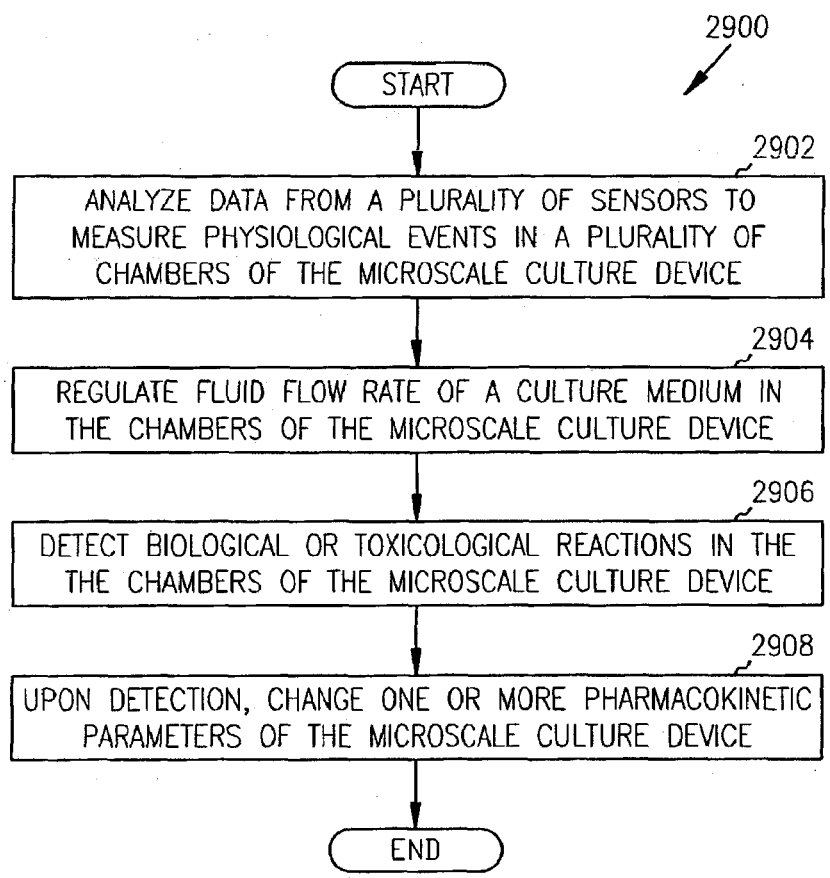
FIG. 29 is a flow-diagram view illustrating a computerized method for dynamically controlling a microscale culture device, according to one embodiment of the present invention.

FIG. 29 is a flow-diagram view illustrating a computerized method for dynamically controlling a microscale culture device, according to one embodiment of the present invention. In this embodiment, the computerized method 2900 includes blocks 2902, 2904, 2906, and 2908. Block 2902 includes analyzing data from a number of sensors to measure physiological events in a number of chambers of the microscale culture device. Block 2904 includes regulating fluid flow rates of a culture medium in the chambers of the microscale culture device. Block 2906 includes detecting biological or toxicological reactions in the chambers of the microscale culture device. Upon such detection, block 2908 includes changing one or more pharmacokinetic parameters of the microscale culture device.

In one embodiment, block 2906 (i.e., the detecting) includes detecting a change in dimension of a cell compartment of the microscale culture device. In one implementation, block 2908 (i.e., the changing) includes changing a pharmacokinetic parameter selected from a group consisting of interactions between cells, liquid residence time, liquid to cell ratios, metabolism by cells, and shear stress in the microscale culture device. In another implementation, block 2908 includes changing a pharmacokinetic parameter selected from a group consisting of flow rate, chamber geometry, and number of cells in the microscale culture device.

In another embodiment, the computerized method 2900 further includes optimizing chamber geometry within the microscale culture device, wherein the optimizing includes selecting a quantity of chambers, choosing a chamber geometry that provides a proper tissue or organ size ratio, choosing an optimal fluid flow rate that provides a proper liquid residence time, and calculating a cell shear stress.

In another embodiment, the computerized method 2900 further includes regulating a temperature of the culture medium. In yet another embodiment, the computerized method 2900 further includes detecting fluorescent emissions from a cell compartment of the microscale culture device.

In another embodiment, a computer-readable medium includes computer-executable instructions stored thereon to perform the various embodiments of the computerized method described above. In one implementation, the computer-readable medium includes a memory or a storage device. In another implementation, the computer-readable medium includes a computer data signal embodied in a carrier wave.

Figure 30:
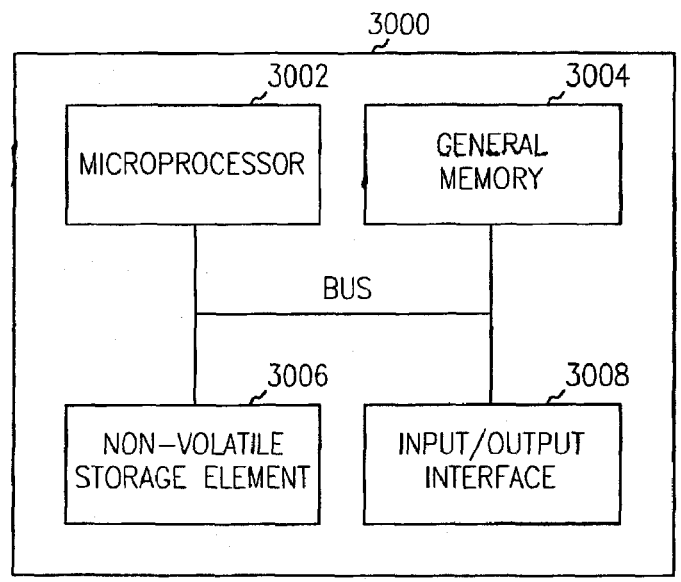
FIG. 30 is a block-diagram view illustrating a computer for controlling a microscale culture device, according to one embodiment of the present invention.

FIG. 30 is a block-diagram view illustrating a computer for controlling a microscale culture device, according to one embodiment of the present invention. In this embodiment, the computer 3000 includes a microprocessor 3002, a general memory 3004, a non-volatile storage element 3006, an input/output interface 3008 that includes an interface to a microscale culture device having one or more sensors, and computer software. The computer software is executable on the microprocessor 3002 to regulate fluid flow rates of a culture medium in a number of chambers in the microscale culture device, detect biological or toxicological reactions in the chambers of the microscale culture device, and upon detection, change one or more pharmacokinetic parameters of the microscale culture device.

In one embodiment, the non-volatile storage element 3006 includes historical data taken from published information, data gathered from previously run tests, or data derived from theoretical calculations. The computer software regulates the fluid flow rates by transmitting commands to one or more pumps of the microscale culture device through pump control lines. In one implementation, the computer software is further executable on the microprocessor 3002 to regulate a temperature of the culture medium. The computer software regulates the temperature by transmitting commands to a heater coil of the microscale culture device through heater coil control lines.

In another embodiment, the computer 3000 further includes a look-up table memory coupled to the general memory 3004 for storing a set of mass balance equations that represent physiologically-based pharmacokinetic models for various biological or chemical substances in the system, and a cache memory coupled to the microprocessor 3002 for storing the computer software.

In another embodiment, the input/output interface 3008 further includes a keyboard interface, a display interface, and a printer/plotter recorder interface. In one implementation, the computer 3000 uses these input/output interfaces to connect to keyboard, display, and printer/plotter recorder peripheral devices.

Experimental

The following examples are put forth so as to provide those of ordinary skill in the art with a complete disclosure and description of how to make and use the subject invention, and are not intended to limit the scope of what is regarded as the invention.

Efforts have been made to insure accuracy with respect to the numbers used (e.g., amounts, temperature, concentrations) but some experimental errors and deviations arise. Unless otherwise indicated, parts are parts by weight, molecular weight is weight average molecular weight, temperature is in degrees centigrade; and pressure is at or near atmospheric.

Methods

The following methods were used in the experimental process:

Cell culture. Cells were obtained from American Type Culture Collection (Manassas, Va.) and propagated in the recommended complete growth medium in a tissue culture incubator (95% $O_2$/5% $CO_2$). For HepG2 and HepG2/C3A cells, the recommended media is Eagle's Minimum Essential medium (with Earle's balanced salts solution, 2 mM L-glutamine, 1.0 mM sodium pyruvate, 0.1 mM nonessential amino aids, 1.5 g/L sodium bicarbonate, and 10% fetal bovine serum) (EMEM). McCoy's 5a medium with 1.5 mM L-glutamine, 1.5 g/L sodium bicarbonate and 10% fetal bovine serum is recommended for the HCT116.

Growth curves. Growth curves were determined by plating the cells at an initial low density in 35 mm dishes. Each day, cells were detached with trypsin-EDTA and cell number was determined by visually counting the cells using a hemacytometer. Determinations were done in triplicate.

Reverse transcriptase-polymerase chain reaction (RT-PCR). Cells were cultured on glass coverslips treated with collagen, MATRIGEL™, or poly-lysine as appropriate. HepG2/C3A grown to a ~90% confluent monolayer were detached with trypsin-EDTA and pelleted at ~500 g for 5 min. RNA was isolated and purified with RNEASY™ kit (Qiagen) according to manufacturer's protocol. Adult human liver total RNA was purchased from Ambion. The quantity and purity (260/280 nm ratio) of isolated RNA was measured on a BIO-PHOTOMETER™ spectrophotometer (Eppendorf). The isolated RNA was then incubated at 37° C. for 25 min with 2 U of DNase I and subsequently inactivated with DNase Inactivation Reagent (Ambion).

The RT reaction was performed using a mixture of 5 µg RNA, 10 µM oligo dT primers heated to 72° C. for 2 minutes followed by 2 minute on ice. Next, 5 mM DTT, 600 µM dNTP mix, 40 U rRNasin, 200 U SUPERSCRIPT II™ in reverse transcriptase buffer were combined and incubated at 42° C. for 1 hour.

2.0 µl of first strand cDNA was used in 50 µl PCR reactions using cytochrome P450 isoform specific primers (Rodriguez-Antona, C., Jover, R., Gomez-Lechon, M.-J., and Castell, J. V. (2000). Quantitative RT-PCR measurement of human cytochrome P-450s: application to drug induction studies. *Arch. Biochem. Biophys.*, 376:109-116). PCR conditions were: 94° C. for 4 minutes followed by 28 cycles of 40 seconds at 94° C., 45 seconds at 60° C., 50 seconds at 72° C., and a final 4 minutes extension at 72° C.

PCR products were separated by electrophoresis on a 1.2% agarose gel and visualized by staining with SYBR Gold and compared to appropriate molecular weight standards for authenticity. To quantify the amplified cDNA, 15 µl of each PCR reaction was diluted with 0.1× Tris-EDTA buffer and stained with PICOGREEN™ (Molecular Probes) at a final concentration of 1:400. Fluorescence was measured at 480 nm excitation and 520 nm emission. Results were standardized against µ-actin and done in triplicate from at least two separate experiments.

Cell viability, death and apoptosis assays. Cell viability and cell death were determined using trypan blue exclusion or LIVE/DEAD stain (Molecular Probes). Trypan blue (GIBCO), normally excluded from the cytoplasm, identifies cells with compromised membranes by visibly staining dead or dying cells blue. A 1:1 dilution of a 0.4% (w/v) solution of trypan blue is added to the recirculating culture medium of the chip device at the conclusion of the experiment. This solution was pumped through the chip to waste for 30 minutes at room temperature. The housing was removed from the pump and visualized under a reflecting microscope (Micromaster, Fisher).

LIVE/DEAD stain is a two-component stain consisting of calcein AM and ethidium homodimer. Living cells actively hydrolyze the acetoxymethyl ester (AM) moiety of calcein AM to produce bright green fluorescence of calcein. In contrast, cells that have compromised membrane integrity allow the normally membrane impermeant ethidium homodimer to stain the nucleus of dead or dying cells fluorescent red. The cell permeant nuclear stain, Hoechst 33342 acts as a general stain for all cells. Together with the appropriate filter sets, living cells fluoresce green, dying or dead cells red, and all cells are quantified by a blue nuclear fluorescence. For experiments described herein, trypan blue was used at 0.2% (w/v), calcein AM at 1:20,000, propidium iodide at 1:5,000, and Hoechst 33342 at 10 µg/ml. Cells were visualized with a M2Bio stereofluorescence microscope (Zeiss). All experiments were repeated at least three times and measurements done in triplicate.

Apoptosis, or programmed cell death, can be monitored using a number of methods (Smyth, P. G., Berman, S. A., and Bursztajn, S. (2000). Markers of apoptosis: methods for elucidating the mechanism of apoptotic cell death from the nervous system. *Biotechniques*, 32:648-665). To distinguish apoptosis from necrosis, at least two separate indicators of apoptosis are required (Wronski, R., Golob, N., and Gryger, E., (2002). Two-color, fluorescence-based microplate assay for apoptosis detection. *Biotechniques*, 32:666-668. One method, annexin V-FITC binding, relies on the observation that annexin V binds tightly to phosphatidylserine in the presence of divalent calcium (Williamson, P., Eijnde, S. v. d., and Schlegel, R. A. (2001). Phosphatidylserine exposure and phagocytosis of apoptotic cells. In Apoptosis, L. M. Schwartz, and J. D. Ashwell, eds. (San Diego, Academic Press), pp. 339-364). Normally, phosphatidylserine is present on the inner leaflet of cell membranes, but translocates to the cell membrane early in apoptosis. Apoptotic cells exposed to fluorophore-labeled annexin exhibit distinct membrane staining. With the microscale chip, annexin V-FITC labeling was visualized directly on-chip, by first flushing the system with PBS, then recirculating annexin V-FITC (10 µg/ml in annexin V binding buffer, Clontech) for 30 min. Cells were then visualized directly using a FITC filter set.

In contrast to annexin V labeling, the APOPTAG™ kit (Intergen Co., MA) uses terminal deoxynucleotidyl transferase to label free 3'-OH DNA termini exposed during apoptotic DNA degradation and visualization using immunofluorescence (Li, X., Traganos, F., Melamed, M. R., and Darzynkiewicz, Z. (1995). Single-step procedure for labeling DNA strand breaks with flourescein or BODIPY-conjugated deoxynucleotides: detection of apoptosis and bromodeoxyuridine incorporation. Cytometry 20, 172-180). Although this method is highly specific for apoptosis, the procedure cannot be done on-chip due to the fixation and incubation steps. Briefly, microscale chips were run under specified experimental conditions, the cell chips were removed from their housing units, fixed in 1% paraformaldehyde and processed with the APOPTAG™ kit using the manufacturer's protocol.

Microscale Chip Fabrication and Experimental Methods. Microscale chips were fabricated as follows: A pattern using a computer assisted design (CAD) software (Cadence) was designed and a chrome photomask using a GCA/Mann 3600F Optical Pattern Generator was created. This high-resolution pattern was then transferred to a silicon wafer (3 inch diameter) containing a thin coat (~1 µm) of positive photoresist (Shipley 1813) by exposing the wafer to UV light through the photomask using a Karl Suss MA6 Contact Aligner. Following exposure, the photoresist was developed, thus exposing the silicon through the photoresist layer in the defined pattern. The exposed silicon was etched to a specified depth (20 to 100 µm) using a PlasmaTherm SLR 770 ICP Deep Silicon Etch System. The photoresist was stripped from the wafer with acetone. Individual 22 mm square microscale chips were diced from the wafer, washed in Nanostrip (Cyantek), rinsed in distilled water, and dried in a drying oven at 170° C.

Figure 22:
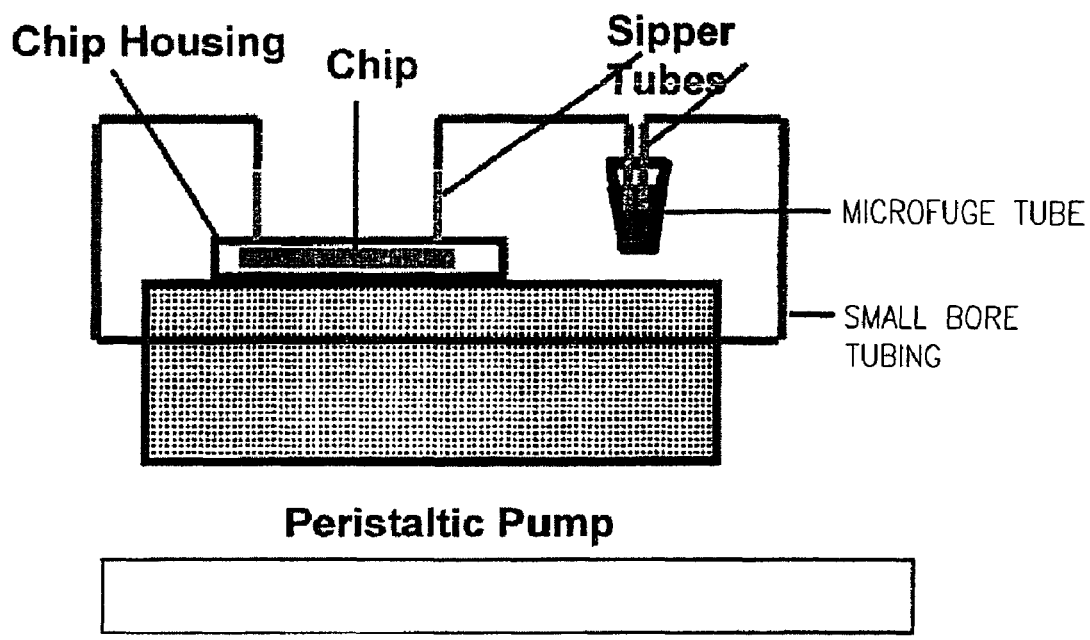
FIG. 22 depicts a schematic drawing of the microscale chip system.

The surface of the silicon in the organ compartments was treated with collagen to facilitate cell attachment. Approximately 10 µl of a 1 mg/ml solution of collagen Type I was deposited onto the surface of the microscale chip and incubated at room temperature for 30 minutes. The collagen solution was removed and the organ compartments were rinsed with cell culture medium. Cells were dissociated from the tissue culture dishes, cell number was determined, and the concentration was adjusted such that there would be a confluent monolayer of cells in each cell compartment. For example, for the microscale chip described in FIG. 2 (hereinabove), 10 µl of a 2,400 cells/µl suspension of the L2 cells was deposited onto the lung chamber of the cell chip and 15 µl of a 3,400 cells/µl suspension of the H4IIE cells was deposited onto the liver chamber. Cells were allowed to attach in a $CO_2$ incubator overnight. Once the cells were attached, the chip was assembled in acrylic chip housings. The top of the housings contain fluid interconnects to provide cell culture medium to the chip. Stainless steel tubes are connected to micro-bore pump tubing and inserted into a small hole in the top of a micro-centrifuge tube containing culture medium with or without test compound. The pump tubing is connected to the peristaltic pump, primed with this solution, and connected to the inlet ports of the chip housing. A small section of pump tubing with a stainless steel tube connected to the end is connected to the outlet port and the tube is inserted into a small hole in the top of the micro-tube, thus completing the re-circulation fluid circuit. The entire instrument is placed in a $CO_2$ incubator at 37° C. A schematic diagram of this setup is presented in FIG. 22.

Example 1

Calculations for a System Replicating a Rat

In designing the chip 1000 all necessary chambers were fit onto a silicon chip no larger than 2 cm by 2 cm. This size of chip is easy to manufacture and is compatible with the sizes of connective tubing and pumping devices intended for use to direct fluid flow. There were also several other important factors constraining the design of the device listed below, along with acceptable values for each variable. This one embodiment of the device consists of a two compartment system, one compartment representing the liver of a rat and one compartment representing the lung of a rat. The total size of the chip is 2 cm by 2 cm and consists of an interconnected array of 20 parallel channels 40 µm wide, 10 µm deep and 5 mm long to serve as the "lung" chamber and two parallel channels 100 µm wide, 20 µm deep and 10 cm long in a serpentine shape to serve as the "liver" chamber. The two organ compartments are connected by a channel 100 µm wide and 20 µm deep. There are many other possible geometries, dimensions, number of chambers, etc. This design was chosen as one example.

TABLE 1

Constraining variables in device design.

| Constraining variable | Acceptable values |
|---|---|
| Chip size | 2 cm × 2 cm |
| "Lung" liquid residence time | 1.5 seconds |
| "Liver" liquid residence time | 25 seconds |
| "Other tissues" liquid residence time | 204 seconds |
| Number of each cell type | >10,000 |
| Cell shear stress | 8-14 dyne/cm$^2$ |
| Channel liquid-to-cell volume ratio | 1 to 2 |

Sample Calculations
Channel or Chamber Calculations:

These calculations assume we have obtained a flow rate from a previous iteration by the method described above with respect to chip 1000 for system 1100.

By this, Q=8.05×10⁵ μm³/trench-second.

The liquid residence time in a trench was then calculated in the following manner:

$$\upsilon R = \frac{V_{Channel}}{Q}$$

Next, the number of cells in a "cell-length" was calculated $$\upsilon_R = \frac{(40\ \mu m) \cdot (10\ \mu m) \cdot (5000\ \mu m)}{\left(8.05 \times 10^5 \frac{\mu m}{sec}\right)}$$

$$\upsilon_R = 2.48\ sec$$

$$N_{Length} = \frac{Channel\_Width}{Cell\_Diameter} + \frac{2 \cdot Wall\_Height}{Cell\_Diameter}$$

$$N_{Length} = \frac{40\ \mu m}{7.41\ \mu m} + \frac{20\ \mu m}{7.41\ \mu m}$$

$N_{Length} = 7$ Cells (Each term is separately rounded down)

Then, a channel/chamber cell-length volume was calculated, $V_{TCL}$=(Cell Diameter)·(Trench Cross Sectional Area)

$V_{TCL}$=(7.41 μm)·(400 μm²)

$V_{TCL}$=2960 μm³

The cell-length volume was also determined.

$$V_{CCL} = \frac{(N_{Length}) \cdot (V_{Cell})}{2}$$

$$V_{CCL} = (7\ Cells) \cdot \left(\frac{320\ \mu m^3}{2\ cell}\right)$$

$$V_{CCL} = 1120\ \mu m^3$$

The liquid cell-length volume is simply the cell cell-length volume subtracted from the channel/chamber cell-length volume. The ratio of the cell cell-length volume and the liquid cell-length volume gives the liquid-to-cell volume ratio for the system:

$$\text{Liquid-to-cell ratio} = \left(\frac{V_{LCL}}{V_{CCL}}\right)$$

$$\text{Ratio} = \left(\frac{2960\ \mu m^3 - 1120\ \mu m^3}{1120\ \mu m^3}\right)$$

Ratio = 1.65

The shear forces on individual cells associated with a given flow rate were determined. Based on the liquid cell-length volume and cell diameter, an average surface area available for liquid to flow through was calculated.

$$\text{Average Liquid Surface Area} = \frac{V_{LCL}}{D_{Cell}}$$

$$A_{LS} = \frac{(1844\ \mu m^3)}{7.41\ \mu m}$$

$$A_{LS} = 249\ \mu m^2$$

An average linear velocity of fluid in the channel was then calculated.

$$V_{avg} = \frac{Q}{A_{LS}}$$

$$V_{avg} = \frac{\left(8.05 \times 10^5 \frac{\mu m^3}{sec}\right)}{249\ \mu m^2}$$

$$V_{avg} = 3.23 \times 10^3 \frac{\mu m}{sec}$$

Assuming laminar flow, Stokes' law was used for calculating the drag on a sphere to estimate the total shear force experienced by an individual cell, $$\Gamma_s = \frac{(3\pi\eta D_{Cell} V_{avg})}{A_{Cell}}$$

$$\Gamma_s = \frac{\left(3 \cdot \pi \cdot \left(9.60 \times 10^{-4} \frac{N-sec}{m^2}\right) \cdot (7.41\ \mu m) \cdot \left(3.23 \times 10^{-3} \frac{\mu m}{sec}\right)\right)}{\frac{4}{2} \cdot \pi \cdot \left(\frac{7.41\ \mu m}{2}\right)^2}$$

$$\Gamma_s = 12.6 \frac{dyne}{cm^2}$$

Next, the actual residence time of the liquid in a channel/chamber was verified and calculated to total number of cells in the channel/chamber, $$N_{Cells} = \frac{L_{Trench} \cdot N_{Trenches} \cdot N_{Length}}{D_{Cell}}$$

$$N_{Cells} = \frac{(5000\ \mu m) \cdot (20\ trenches) \cdot (7\ Cells)}{(7.41\ \mu m)}$$

$$N_{Cells} = 9.45 \times 10^4\ Cells$$

I. B. Membrane Oxygenation Calculations:

The area of silicone membrane for oxygenation was determined in the following manner:

First, approximate the Oxygen Uptake Rate (OUR) for the cells:

$$OUR = q_{O_2} \cdot X$$

$$OUR = \left(7.00 \frac{\mu g O_2}{10^6\ cells - hr}\right) \cdot (2 \times 10^5\ cells)$$

$$OUR = 4.4 \times 10^{-5} \frac{mmol O_2}{hr}$$

Then calculate the partial pressure of oxygen on the inside of the membrane to determine if it is sufficient to re-oxygenate the liquid medium. This was done using an equation for the flux of a gas through a porous membrane, where Q is the membrane permeability. J represents the flux of gas into the cells, and z is the thickness of the membrane:

$$J_{O_2} A_{Membrane} = OUR = \frac{Q_{O_2} \cdot (P_{O_2,Out} - P_{O_2,In})}{z}$$

$$\left(4.4 \times 10^{-5} \frac{mmolO_2}{hr}\right) \cdot (55 \text{ mm}^2) =$$

$$\frac{\left(5.00 \times 10^{-8} \frac{[cm^3(STP) \cdot cm]}{(cm^2 \cdot s \cdot cmHg)}\right) \cdot (P_{O_2Out} - 16 \, cmHg)}{0.05 \, cm}$$

$$P_{O_2Out} = 15.5 \, cmHg$$

This pressure is sufficient to saturate the liquid medium with oxygen in the 200 seconds it is in contact with the membrane. The area of membrane was determined in an iterative manner so as to maximize the inside oxygen partial pressure.

Principle Design Calculations

Rat Model:

| Primary cell characteristics | Lung (L2) | Liver (H4IIE) |
|---|---|---|
| Surface area (cm²/organ) | 4890 | 21100 |
| Cell volume (μm³/cell) | 320 | 4940 |
| Plating area (μm²/cell) | 320 | 988 |
| Cell Diameter (μm) | 7.41 | 18.5 |

Stokes' law: $3\pi\eta DU = F_D$ (Plating area is the inverse of experimentally determined saturation densities for L2 and H4IIE cells.)

LUNG CELL CALCULATIONS:

Calculation of cell and liquid volumes in one cell-length of channel/chamber:

| | | |
|---|---|---|
| Cell diameter | 7.41 μM | (a cell-length included the diameter of the cell as well as spacing on either side equal to the "distance between cells") |
| Cell volume | 320 μm³/cell | |
| Channel width | 40 μm | |
| Channel depth | 10 μm | |
| Spacing between channels | 30 μm | |
| Channel X-sectional area | 400 μm² | |
| Cells across channel | 5 | |
| Cells on side of channel | 1 | |
| Total cells in one cell-length | 7 | |
| Channel cell-length volume | 2964 μm³ | |
| Cell cell-length volume | 1120 μm³ | |
| Liquid cell-length volume | 1844 μm³ | |
| Liquid-to-cell volume ratio | 1.65 | |

Determination of liquid velocity and shear on individuals cells:

| | | |
|---|---|---|
| Viscosity of cell plasma medium | 9.60E−04 N-s/m² | |
| Number of channels | 20 | (this number picked to give adequate # of cells and feasible flows) |
| Liquid flow rate per channel | 8.05E+05 μm³/sec | (this number picked to give a stress of 12 dyne) |
| Average liquid surface area | 249 μm² | |
| Average liquid linear Velocity, U | 3.23E+03 μM/SEC<br>3.23E−03 M/SEC | |
| Drag force on individual cell | 1.08E−10 Newtons<br>1.08E−04 μN<br>1.08E−05 dyne | (for a half-sphere) |
| Surface area of individual cell | 8.63E+01 μm²<br>8.63E−07 cm² | (for a half-sphere) |

LUNG CELL CALCULATIONS:

| | | |
|---|---|---|
| Shear stress on individual cell | 12.6 dyne/cm² | (This result assumes smooth half-spherical geometry for the cells; it is likely the actual number is small due to larger surface area or surface irregularities) |
| Total flow rate | 1.61E+07 μm³/sec | |
| Desired residence time | 1.5 seconds | |
| Channel length | 5 mm | (this number is chosen to give the desired residence time) |
| Total Channel liquid volume | 2.49E+07 μm³ | |
| Actual Residence time | 1.55 seconds | |
| Total number of cells | 9.45+04 cells | |

LIVER CELL CALCULATIONS:

Calculation of cell and liquid volumes in one cell-length of channel/chamber

| | |
|---|---|
| Cell diameter | 18.5 μm |
| Cell volume | 4940 μm³/cell |
| Channel width | 100 μm |
| Channel depth | 20 μm |
| Spacing between channels | 50 μm |
| Channel X-sectional area | 2000 μm² |
| Cells across channel | 5 |
| Cells on side of channel | 1 |
| Total cells in one cell-length | 7 |
| Channel cell-length volume | 36918 μm³ |
| Cell cell-length volume | 17290 μm³ |
| Liquid cell-length volume | 19628 μm³ |
| Liquid-to-cell volume ratio | 1.14 |

Determination of liquid velocity and shear on individual cells:

| | | |
|---|---|---|
| Viscosity of cell plasma medium | 9.60E−04 N-s/m² | |
| Total liquid flow rate from Lung Calcs. | 1.61E+07 μm³/sec | (from above calcs.) |
| Number of channels | 2 | |
| Liquid flow rate per channel | 8.05E+06 μm³/sec | |
| Average liquid surface area | 1063 μm² | |
| Average liquid linear velocity | U7.57E+03 μm/sec<br>7.57E−03 m/sec | |
| Drag force on individual cell | 6.32E−10 Newtons<br>6.32E−05 dyne | Stokes' law:<br>$3\pi\eta DU = F_D$ |
| Surface area of individual cell | 535.24 μm²<br>5.35E−06 cm² | |
| Shear stress on individual cell | 11.81 dyne/cm² | |
| Desired residence time | 25 sec | |
| channel length | 100 mm | |
| Total Channel liquid volume | 4.00E+08 μm³ | |
| Actual Residence time | 24.86 sec | |
| Total number of cells | 7.58E+04 cells | |

Residence Time Calculations

Actual (Target) Residence Times in Rat Tissues:

| | |
|---|---|
| Lung | 1.5 sec |
| Liver | 25 sec |
| Other Tissues | 204 sec |

Actual Organ Characteristics:

|  | Blood Flow Rate (mL/min) | Volume (mL) |
|---|---|---|
| Lung | 73.3 | 1.2 |
| Liver | 18.3 | 7.4 |
| Other Tissues | 55 | 190 |
| Preliminary flow rate | 0.85 µL/min | |
| | 0.0142 µL/sec | |

Unit Conversions:

| 1 µm | 1 µL |
|---|---|
| 0.000001 m | 1.00E−06 L |
| | 1.00E−09 m$^3$ |
| | 1.00E+09 µm$^3$ |

Calculations Using Serpentine Patterning:

Preliminary Residence Time Calculations for Liver/Lung:

| Channel Depth | 310 µm |
|---|---|
| Channel Width | 500 µm |
| Channel X-sectional Area | 0.155 mm$^2$ |
| | 155000 µm$^2$ |
| Cells per area | 3200 cells/mm$^2$ |

| | Residence Time (sec) | Channel Volume (µL) | Channel Length (mm) | Surface Area (mm$^2$) | Max # cells |
|---|---|---|---|---|---|
| Lung | 1.5 | 0.02125 | 0.1 | 6.85E+01 | 2.58E+04 |
| Liver | 25 | 0.4 | 2 | 1.14E+03 | 3.66E+06 |

Preliminary Residence Time Calculations for Other Tissues:

| Channel Depth | 50 µm |
|---|---|
| Channel Width | 2000 µm |
| Channel X-sectional Area | 0.1 mm$^2$ |
| | 100000 µm$^2$ |

| Residence Time (sec) | CHANNEL VOLUME (µL) | Channel Length (mm) | Surface Area (mm$^2$) |
|---|---|---|---|
| 204 | 2.89 | 29 | 57.8 |

Example 2

A Four Organ Compartment Chip

A chip was designed to consist of four organ compartments—a "liver" compartment to represent an organ responsible for xenobiotic metabolism, a "lung" compartment representing a target tissue, a "fat" compartment to provide a site for bio-accumulation of hydrophobic compounds, and an "other tissues" compartment to assist in mimicking the circulatory pattern in non-metabolizing, non-accumulating tissues (FIG. 15). These and other organ compartments (e.g., kidney, cardiac, colon or muscle) can be fully modularized as CAD files and can be fabricated in any configuration or combination. The device itself can be produced in any number of substrates (e.g., silicon, glass, or plastic).

Once the cells were seeded in the appropriate compartments, the chip was assembled in a Lucite manifold. This manifold holds four chips and contained a transparent top so the cells could be observed in situ. The top contained fluid interconnects to provide cell culture medium to the chip. The culture medium was pumped through the chip using a peristaltic pump at a flow rate of 0.5 µl/min. Culture medium was re-circulated in a closed loop consisting of a fluidic reservoir (~15 to 50 µl total volume), micro-bore tubing, and the compartments and channels of the chip.

Using a three compartment system with human HepG2-C3A cells in the liver compartment and HT29 colon cancer cells in the target tissues compartment, it was found that cells remain viable under continuous operation for greater than 144 hours. HepG2-C3A cells are a well characterized human liver cell line known to express various liver metabolizing enzymes at levels comparable to fresh primary human hepatocytes. In these experiments, cells were seeded in the appropriate compartments and a specially formulated cell culture medium was re-circulated through the system for up to 144 hours. At various time points, the culture medium was switched to PBS containing LIVE/DEAD fluorescent reagent (a dual fluorescent stain, [Molecular Probes, Inc., Eugene, Oreg., USA]) for 30 minutes. Cells were visualized under a fluorescent microscope and fluorescent images of identical fields were obtained using the appropriate filter sets. Living cells fluoresced green whereas dead cells were red (data not shown).

Example 3

Drug Metabolism in the Chip

The metabolism of two widely used prodrugs, tegafur and sulindac sulfoxide, was studied using a microscale chip comprising three compartments, liver, target tissue, and other tissues. Both prodrugs require conversion to an active metabolite by enzymes present in the liver, and have a cytotoxic effect on a target organ. For the prodrug sulindac sulfoxide, its anti-inflammatory and cancer chemopreventive properties are derived from its sulfide and sulfone metabolites, catalyzed by the liver enzyme sulfoxide reductase. The sulfide metabolite (and a second sulfone metabolite) have been demonstrated to induce apoptosis in certain cancer cells (e.g., colon cancer).

A proper treatment regimen requires administration of its prodrug, tegafur [5-fluoro-1-(2-tetrahydrofuryl)-2,4(1H,3H)-pyrimidi-nedione] as 5-FU itself is quite toxic to normal cells. Unlike sulindac however, tegafur is converted to 5-FU in the liver primarily by cytochrome P450 2A6.

To test the efficacy of sulindac, the microscale chip was seeded with HepG2-C3A cells in the liver compartment and HT29 human colon cancer cells in the target tissue compartment. One hundred micromoles of Sulindac (need manufacturer) was added to the re-circulating medium for 24 hours and the chip was treated as described above—living cells fluoresced green and dead cells fluoresced red (data not shown). In the absence of the HepG2-C3A liver cells, minimal levels of cell death (similar to vehicle control) was observed. These results demonstrate that a drug can be metabolized in the liver compartment and consequently circulate to a target where its metabolite(s) induce a biological effect much as it would in a living animal or human.

The cancer therapeutic pro-drug tegafur was tested in the microscale chip system. For efficacy, tegafur requires metabolic activation by cytochrome P450 enzymes present in the liver to its active form, 5-fluorouracil (5-FU) (Ikeda, K., Yoshisue, K., Matsushima, E., Nagayama, S., Kobayashi, K., Tyson, C. A., Chiba, K., and Kawaguchi, Y. (2000). Bioactivation of tegafur to 5-fluorouracil is catalyzed by cytochrome P-450 2A6 in human liver microsomes in vitro. *Clin. Cancer Res.*, 6, 4409-4415; Komatsu, T., Yamazaki, H., Shimada, N., Nakajima, M., and Yokoi, T. (2000). Roles of cytochromes P450 1A2, 2A6, and 2C8 in 5-fluorouracil formation from tegafur, an anticancer prodrug, in human liver microsomes. *Drug Met. Disp.*, 28, 1457-1463; Yamazaki, H., Komatsu, T., Takemoto, K., Shimada, N., Nakajima, M., and Yokoi, T. (2001). Rat cytochrome P450 1A and 3A enzymes involved in bioactivation of tegfur to 5-fluorouracil and autoinduced by tegafur liver microsomes. *Drug Met. Disp.*, 29, 794-797. A proper therapeutic regimen requires administration of its prodrug, tegafur, as 5-FU itself is very toxic to normal cells. 5-FU is currently the most effective adjuvant therapy for patients with colon cancer (Hwang, P. M., Bunz, F., Yu, J., Rago, C., Chan, T. A., Murphy, M. P., Kelso, G. F., Smith, R. A. J., Kinzler, K. W., and Vogelstein, B. (2001). Ferredoxin reductase affects p53-dependent, 5-fluorouracil-induced apoptosis in colorectal cancer cells. *Nat. Med.*, 7, 1111-1117.) Like most chemotherapeutic agents, 5-FU induces marked apoptosis in sensitive cells through generation of reactive oxygen species (Hwang, P. M., Bunz, F., Yu, J., Rago, C., Chan, T. A., Murphy, M. P., Kelso, G. F., Smith, R. A. J., Kinzier, K. W., and Vogelstein, B. (2001). Ferredoxin reductase affects p53-dependent, 5-fluorouracil-induced in colorectal cancer cells. *Nat. Med.*, 7, 1111-1117).

Figure 16A:
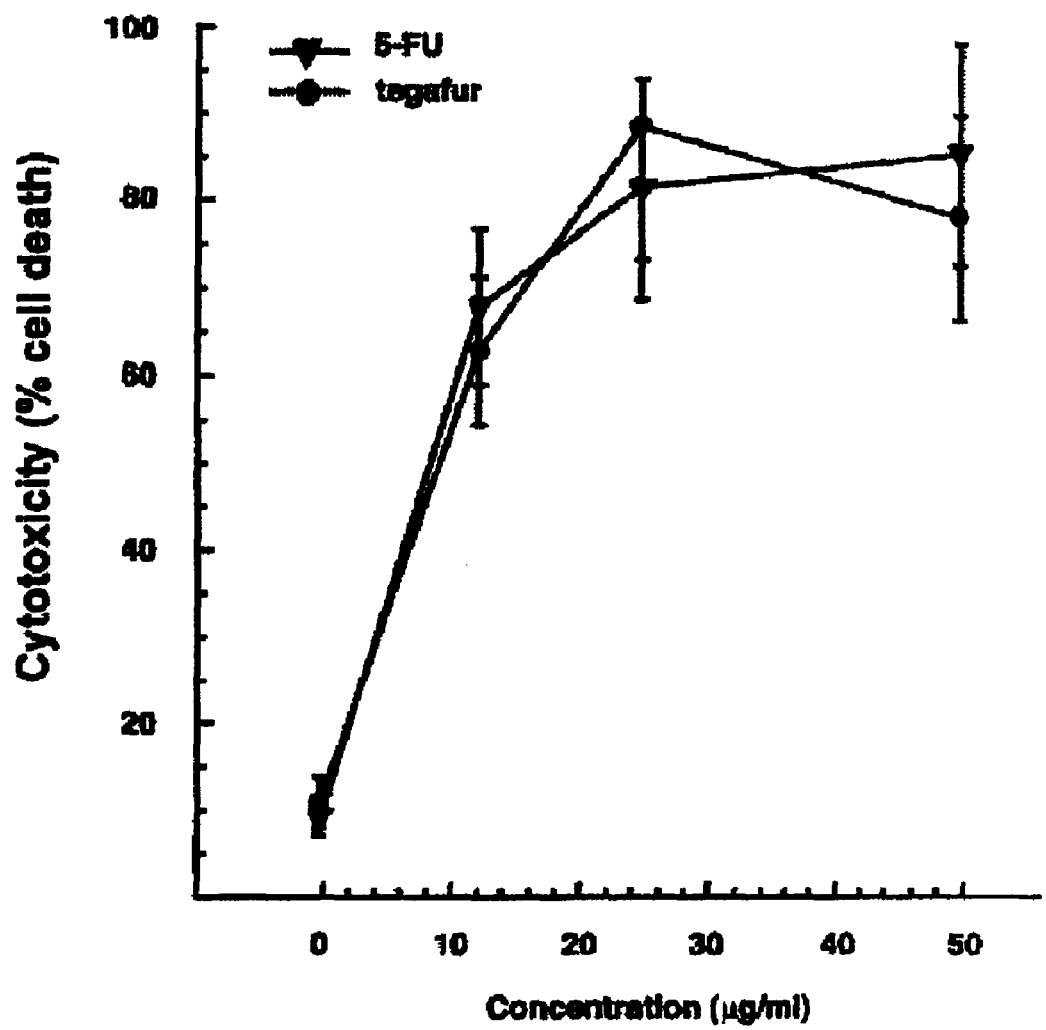
FIG. 16 Tegafur dose response. Chips were seeded with HepG2-C3A cells in the liver compartment and HCT-116 colon cancer cells in the target tissues compartment. The chips were treated with indicated concentrations of tegafur for 24 hours. The first graph (FIG. 16A) is a plot of percentage dead cells vs. tegafur or 5-FU concentration after 24 hours of re-circulation on the chip. The second graph (FIG. 16B) is a similar dose response using a traditional in vitro cell culture assay with HCT116 cells using a 48 hour exposure. HCT-116 cells were seeded on poly-lysine treated glass coverslips and exposed to either tegafur or 5-FU at the indicated concentrations. After a 48 hr incubation, coverslips were treated as described above and the percentage of cell death was determined.
Figure 16B:
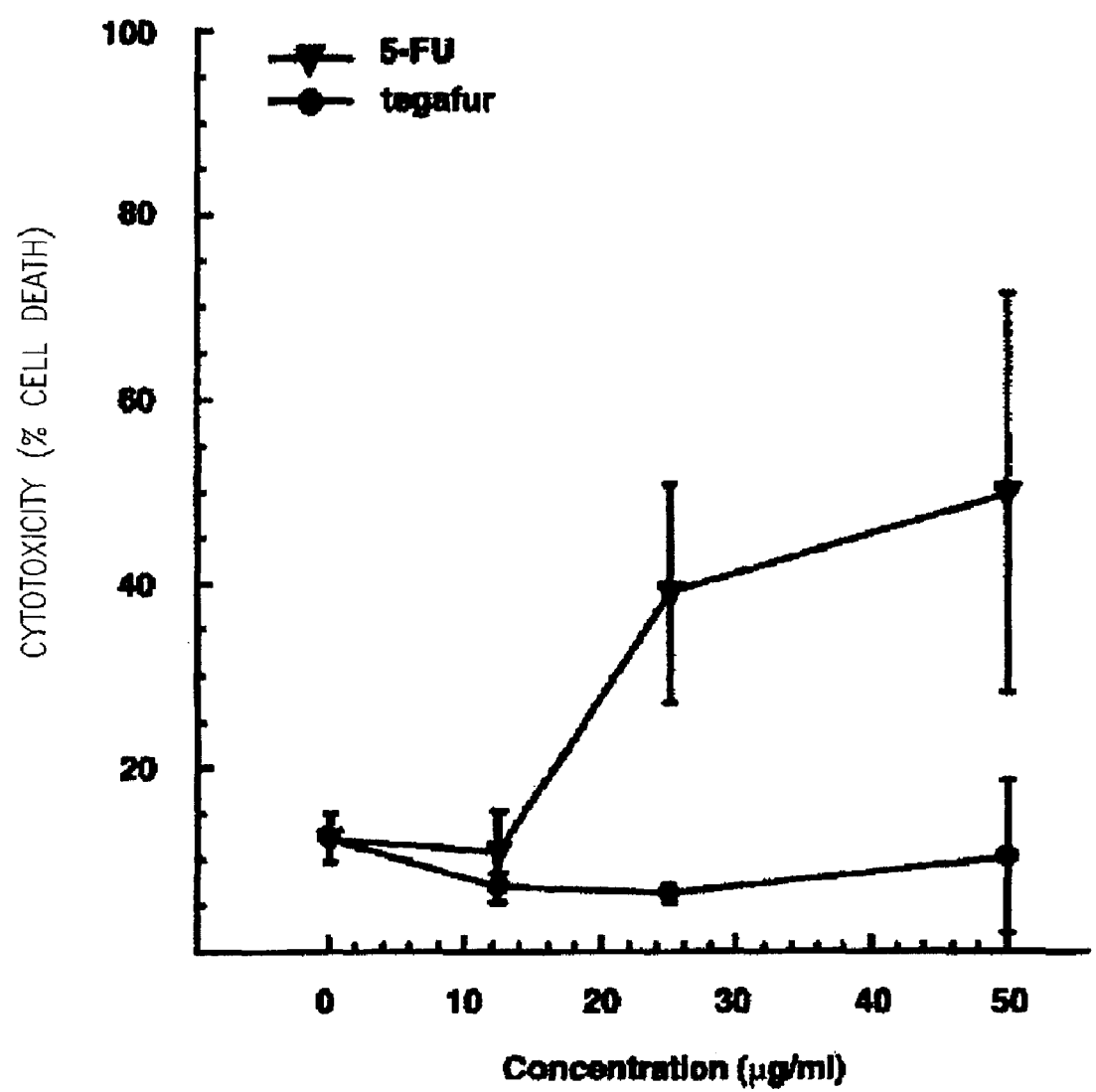

To measure the cytotoxic effects of tegafur against colon cancer cells, the microscale chip was prepared with HepG2-C3A cells in the liver compartment and HCT-116 human colon cancer cells in the target tissue compartment. Tegafur was added to the re-circulating medium at various concentrations for 24 hours and the cells labeled with Hoechst 33342, a membrane permeable DNA dye, and ethidium homodimer, a membrane impermeable DNA dye (see Methods Section). All cells fluoresce blue, but dead cells were marked by the fluorescent red ethidium homodimer (data not shown). Tegafur was cytotoxic to HCT-116 cells in a dose-dependent fashion in this microscale chip system, while it was ineffective with the traditional cell culture assay (FIGS. 16A and 16B). In addition, while 5-FU triggered cell death in the traditional cell culture assay, cytotoxicity was not observed until after 48 hours of exposure compared to 24 hours of exposure to tegafur with the microscale chip.

To demonstrate that the liver compartment was responsible for the bio-activation of tegafur, the microscale chips were seeded with HCT-116 cells only. No cells were in the liver compartment. Tegafur or 5-FU was added to the re-circulating culture medium for 24 hours and the chip was treated as described above (data not shown). Tegafur did not cause significant cell death of the HCT-116 cells in the absence of a liver compartment while the active metabolite 5-FU caused substantial cell death. Further, when HT-29 colon cancer cells are substituted for HCT-116, tegafur was ineffective (data not shown). This was likely due to the mutant p53 present in HT-29 cells, which is necessary for 5-FU cytotoxicity. Together, these experiments demonstrate that tegafur, like sulindac, was metabolized to an active drug in the liver compartment where it circulated to another organ compartment to eliminate the cancer cells. These effects were mechanistically distinguishable with the chip—sulindac was effective even in the absence of an active p53, whereas tegafur was not.

Example 4

Multiple Cell Cultures in a Single Organ Compartment

It is also possible to use a mixture of multiple cell types in a single organ compartment. In one study, the hepatocyte cell line HepG2/C3A (from ATCC) is used in the liver compartment. The cells are propagated in McCoy's 5A medium with 1.5 mM L-glutamine 1.5 g/L sodium bicarbonate and 10% fetal bovine serum. To more closely mimic an in vivo organ, a mixture of primary hepatocytes and fibroblasts can be used at a 1 to 2 ratio along with macrophages (Kupffer cells).

In another example, a mixture of cells or cell lines derived from lung epithelial cells is used to more closely mimic the lung tissue. This includes a mixture of type I epithelial cells, type II epithelial cells (granular pneumocytes), fibroblasts, macrophages and mast cells.

Example 5

Optimization of Tissue Culture Conditions in the Chip-Based System

A tissue culture medium compatible with two different rat cell culture lines, H4IIE (a rat liver cell line) and L2 (a rat lung cell line) was developed. Preliminary experiments indicated that a 1:1 mixture of DMEM and Hams F12K medium supplemented with 2 mM L-glutamine, 1 mM sodium pyruvate and 10% fetal bovine serum (FBS) maintained the viability of both H4IIE cells and L2 cells for up to 20 hours of continuous operation in a microscale chip. This media formulation was used for all rat-based microscale chip studies.

Figure 23:
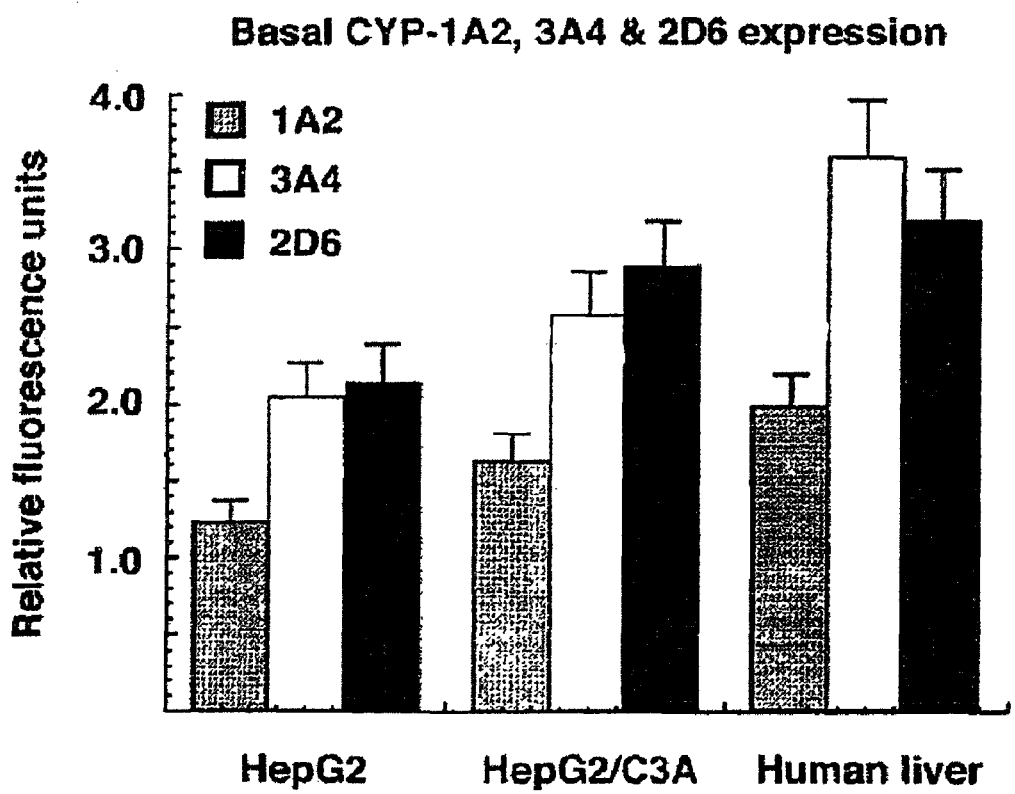
FIG. 23 depicts basal CYP expression levels for Hep G2, HepG2/C3A, and human liver. Std. error from 3 separate determinations.

The proper human liver cell line that realistically mimics human liver function was selected Additionally, the optimum cell culture medium formulation for maintaining human cell lines on a microscale chip was determined. The basal expression levels of three key cytochrome P450 (CYP) isoforms (1A2, 3A4, and 2D6) in HepG2 and HepG2/C3A (a HepG2 subclone) cell lines were examined. CYP-1A2, 2D6, and 3A4 were examined because they account for the metabolism of 80-90% of all known drugs (Hodgson, J., (2001). ADMET—turning chemicals into drugs. *Nat. Biotech.*, 19, 722-726. The C3A subclone of the HepG2 liver cell line was examined as this cell line has been reported to be a highly selected cell line exhibiting more "liver-like" characteristics, particularly much higher CYP expression compared to the parental cell line (Kelly, J. H. (1994). Permanent human hepatocyte cell line and its use in a liver assist device (LAD). U.S. Pat. No. 5,290,684). The RT-PCR analysis confirmed that basal CYP levels in HepG2/C3A cells were significantly greater than HepG2 parentals and comparable to adult human liver (FIG. 23).

HepG2/C3A cells were used as a liver surrogate in all subsequent experiments. To select a common media for use during microscale chip experiments, the components of a number of media were compared (DMEM, McCoy's 5a, RPMI 1640, MEM, F12, F12K, Waymouth's, CMRL, MEM, and Iscove's modified Dulbecco's medium). Analysis of the inorganic salt, glucose, amino acid composition, and vitamin content suggested that EMEM, DMEM, McCoy's 5a and RPMI were the most suitable "common" media of the media examined. After several passages, cells were then split and sub-cultured in the following media:

Eagle's Minimum Essential medium (EMEM) with Earle's balanced salts solution, 2 mM L-glutamine, 1.0 mM sodium pyruvate, 0.1 mM nonessential amino aids, 1.5 g/L sodium bicarbonate, and 10% fetal bovine serum.

Dulbecco's modified Eagle's medium (DMEM) with 4 mM L-glutamine, 4.5 g/L glucose, 1.5 g/L sodium bicarbonate, and 10% fetal bovine serum.

McCoy's 5a medium (McCoy's) with 1.5 mM L-glutamine 1.5 g/L sodium bicarbonate and 10% fetal bovine serum.

RPMI 1640 medium (RPMI) with 2 mM L-glutamine, 4.5 g/L glucose, 1.0 mM sodium pyruvate, 1.5 g/L sodium bicarbonate.

Figure 24A:
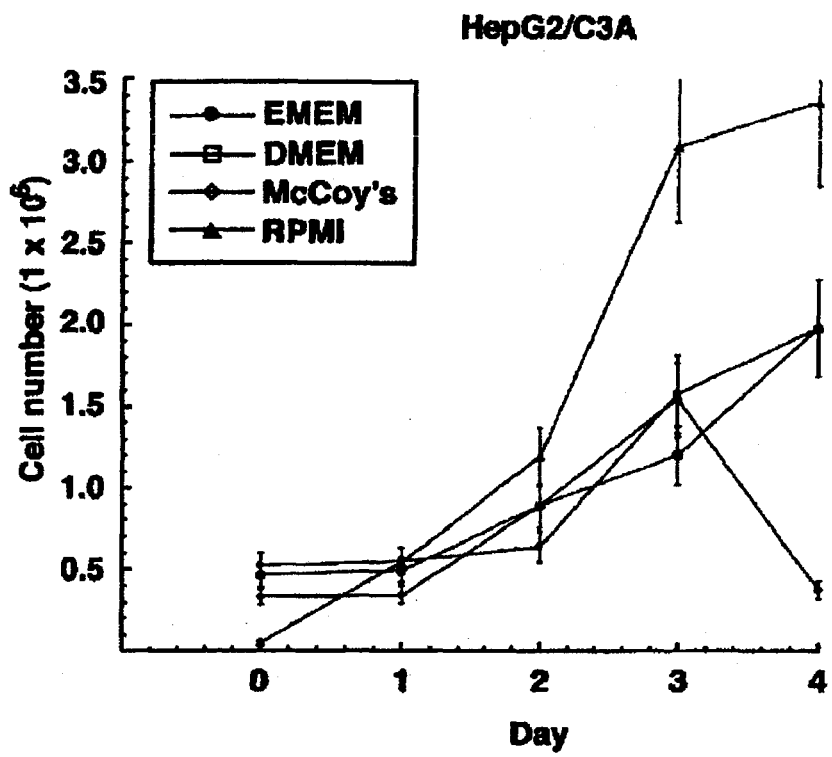
FIG. 24A depicts HepG2/C3A growth curves in EMEM, DMEM, McCoy's and RPMI.
Figure 24B:
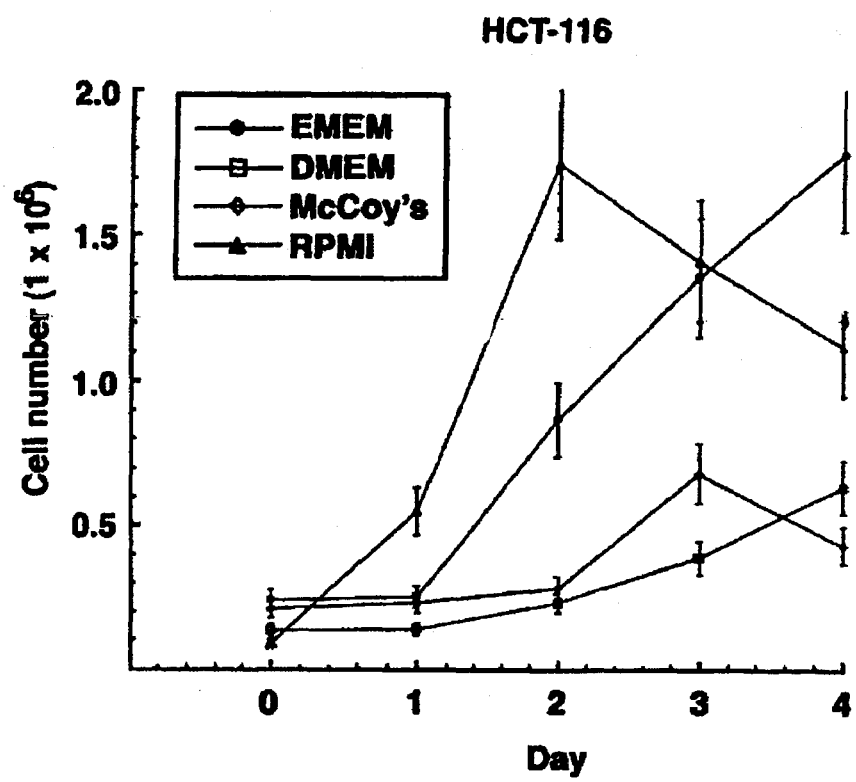
FIG. 24B depicts HCT116 growth curves in EMEM, DMEM, McCoy's and RPMI. Standard error from 3 separate determinations.

Growth curves for both cell lines in each media were then determined as described in the Methods section (FIG. 24). DMEM was found to be inappropriate for the HepG2/C3A cells, as significant changes in cellular morphology and adhesion after ~5 passages were observed (not shown). Similarly, a significant decrease in HepG2/C3A and HCT116 viability and growth after 3 days in RPMI was noticed. Both cell lines grew well in McCoy's and EMEM compared to their preferred medium.

Figure 25:
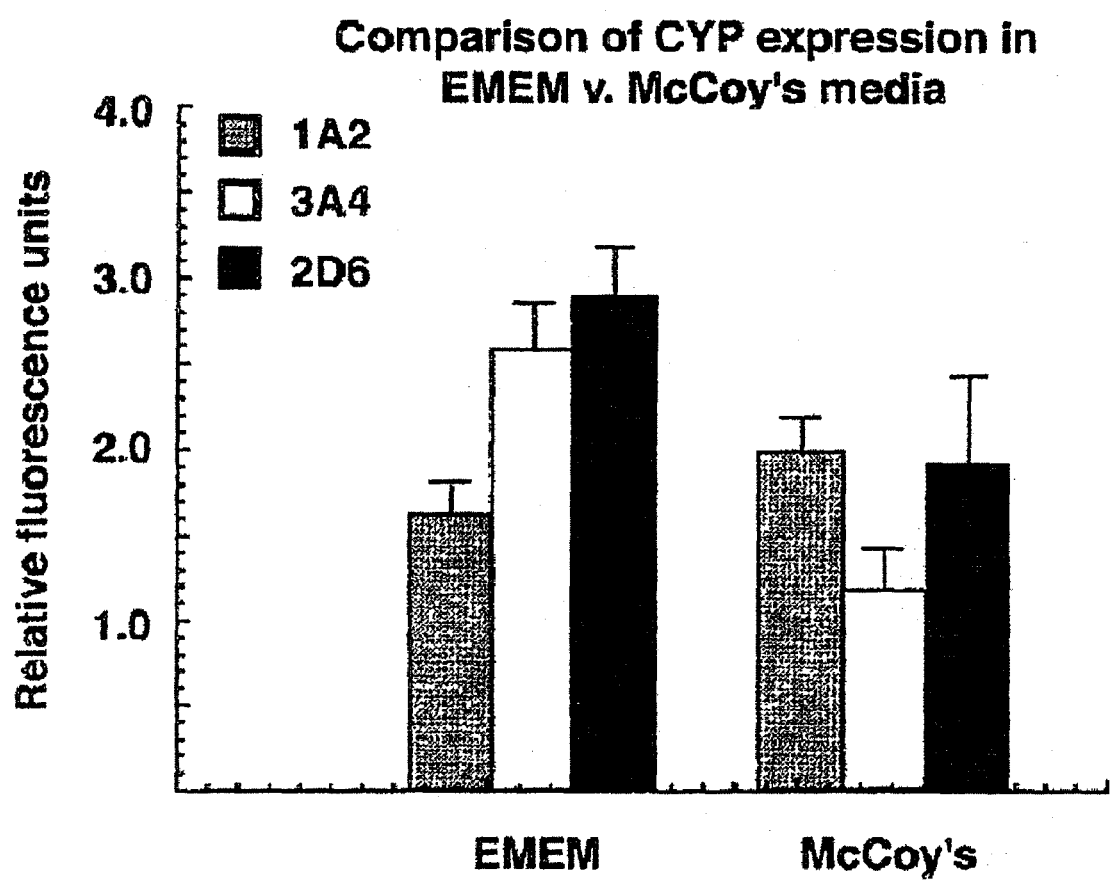
FIG. 25 depicts RT-PCR determination of CYP isoforms expression in HepG2/C3A under different growth media conditions.
Figure 26:
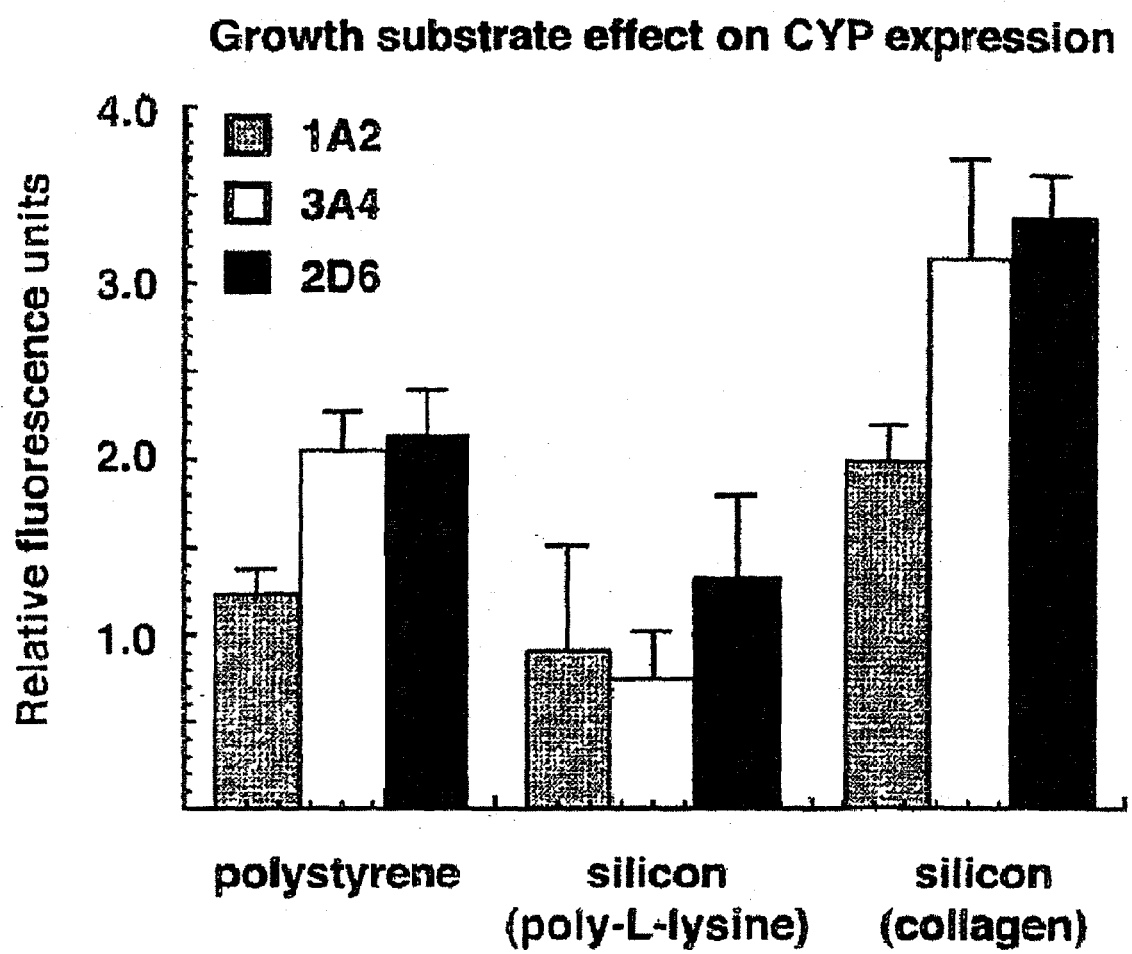
FIG. 26 depicts RT-PCR determination of CYP isoforms expression in HepG2/C3A grown on different substrates.

Next, the expression levels of these CYP isoforms in HepG2/C3A cells growing in either EMEM or McCoy's using RT-PCR were investigated (see Methods section) (FIG. 25). The results indicated that EMEM was superior to McCoy's for maintaining CYP expression and the preferred media for HepG2/C3A. The effect of different growth substrates on CYP expression was studied (FIG. 26). A comparison of silicon treated with either poly-D-lysine or collagen as the attachment substrate against cells grown on standard tissue culture treated polystyrene was performed. Together, the results indicated that EMEM supported the growth of both HepG2/C3A and HCT116 cells and that collagen was the preferred substrate based on RT-PCR CYP expression analysis.

Using these conditions, the long term cell viability of these cells, HepG2/C3A and HCT116, was studied under continuous operation in the microscale chip system. Using a three compartment system with human HepG2/C3A cells in the liver compartment and HCT116 colon cancer cells in the target tissues compartment, it was demonstrated that cells remain viable under continuous operation for greater than 144 hours. In these experiments, cells were seeded in the appropriate compartments and EMEM was re-circulated through the system for up to 144 hours. At various time points (6, 24, 48, 72, 96, 120 and 144 hr), total live or dead cells were visualized using LIVE/DEAD stain (data not shown). Cells were visualized under a fluorescent microscope and fluorescent images of identical fields were obtained using the appropriate filter sets. Living cells fluoresced green whereas dead cells were red (data not shown).

Example 6

Assay for Detection of Cytotoxicity on a Microscale Chip

Trypan blue is the most common stain used to distinguish viable cells from nonviable cells; only nonviable cells absorb the dye and appear blue. Conversely, live, healthy cells appear round and refractile without absorbing the blue dye. Experiments were performed using trypan blue to determine cell viability in a microscale chip. Although trypan blue (see Methods section) is easy to use and requires only a light microscope to visualize, viable cells will absorb trypan blue over time, which can affect results. In addition, trypan blue has a higher affinity for serum proteins than for cellular proteins, thus the background is dark when using serum-containing media. Therefore, alternative methods to distinguish viable cells from dead cells were studied.

The LIVE/DEAD assay was optimized (see Methods section) using cells grown on glass coverslips. Briefly, HepG2/C3A cells were seeded onto poly-D-lysine treated glass coverslips and treated with and without 1 µM staurosporine for 24 hours. Staurosporine is a broad-spectrum protein kinase inhibitor and is known to induce apoptosis in a variety of cell types (Smyth, P. G., Berman, S. A., and Bursztajn, S. (2002). Markers of apoptosis: methods for elucidating the mechanism of apoptotic cell death from the nervous system. *Biotechniques*, 32, 648-665). Coverslips were washed with phosphate buffered saline (PBS) and LIVE/DEAD reagents were added and incubated at room temperature for 30 minutes. The coverslips were removed and visualized (data not shown). Staurosporine was found to clearly cause cell death of HepG2/C3A cells (data not shown).

The assay for detection of cytotoxicity on the microscale chip system was then optimized. Microscale chip cell chips were seeded with HepG2/C3A cells in the liver compartment and HCT116 cells in the target tissues compartment as described in the Methods section. Cell chips were loaded onto the microscale chip system and treated with and without 1 µM staurosporine as described above. After a 24-hour incubation, the recirculating medium was switched to PBS, allowed to flow through the system to waste for 30 minutes, then switched to PBS containing the LIVE/DEAD reagents and flowed through the system for an additional 30 minutes. The acrylic housing containing the cell chips was removed from the system and placed under a stereofluorescence microscope and the cell chip was visualized through the transparent top of the housing (data not shown). Cells were visualized under a fluorescent microscope and fluorescent images of identical fields were obtained using the appropriate filter sets. Living cells fluoresced green whereas dead cells were red (data not shown). Significant cell death of the HCT116 cells was caused by 1 µM staurosporine after a 24 hour treatment compared to untreated control cell chips (data not shown).

Example 7

Chip-Based Assays to Detect the Occurrence of Cell Death and Distinguish Between Apoptosis or Necrosis Two different assays to detect apoptosis were investigated. The first assay was the immunofluorescence-based terminal deoxynucleotidyl transferase BrdU nick end labeling (TUNEL) technique available in kit form as APOPTAG™ (Intergen Co., MA) (see Methods section). The assay was first optimized using cells grown on glass coverslips. Briefly, HepG2/C3A cells were seeded onto poly-D-lysine treated glass coverslips and treated with and without staurosporine. Coverslips were processed as described (see Methods section). Various staurosporine concentrations and treatment times were tested, and the results indicated that 1 µM staurosporine caused significant apoptosis compared to untreated controls after a 24-hour incubation (data not shown). Next, the assay for detection of apoptosis on the microscale chip system was optimized and a comparison of the APOPTAG method to the LIVE/DEAD staining technique was performed. The microscale cell chips were seeded with HepG2/C3A cells in the liver compartment and HCT-116 cells in the target tissues compartment as described in the Methods section. Cell chips were loaded onto the microscale chip system and treated with and without 1 µM staurosporine as described above. After a 24-hour incubation, the recirculating medium was switched to PBS for 30 minutes. Half the cell chips were removed from the housing and the APOPTAG™ assay was performed as described above. The other cell chips were left in the microscale chip system and subjected to the LIVE/DEAD staining technique as previously described. Cells were visualized under a fluorescent microscope and fluorescent images of identical fields were obtained using the appropriate filter sets. Living cells fluoresced green whereas dead cells were red (data not shown). Both techniques produced very similar results, i.e., a 24 hour exposure to 1 µM staurosporine induced significant apoptosis (or cytotoxicity) to the HCT116 cells compared to untreated controls (data not shown).

The annexin V-FITC was used to detect apoptosis in the microscale chip system as described in the Methods section. Briefly, the microscale chip cell chips were seeded with HepG2/C3A cells in the liver compartment and HCT116 cells in the target tissues compartment. Cell chips were loaded onto the microscale chip system and treated with and without 1 µM staurosporine as described above. After a 6-hour incubation, the re-circulating medium was switched to PBS containing Annexin V-FITC and Hoechst 33342 and allowed to flow through the system for 30 minutes. Cell chips were removed from the acrylic housing and visualized under a fluorescent microscope. Cells were visualized under a fluorescent microscope and fluorescent images of identical fields were obtained using the appropriate filter sets. Living cells fluoresced green whereas dead cells were red (data not shown). 1 µM staurosporine caused significant apoptosis after a 6-hour treatment compared to untreated control cell chips (data not shown).

Example 8

Use of Naphthalene as a Model Toxicant

Naphthalene was used to study toxicology because enzymatic conversion in the liver is required for lung toxicity. Therefore, the effects of naphthalene on a rat lung cell line were studied. These experiments used a three compartment (liver, lung, and other tissues) rat-based microscale chip with H4IIE cells in the liver compartment and rat L2 cells in the lung compartment. Microscale chips were fabricated and prepared for experiments as described in the Method section.

The microscale chip system was operated for 20 hours in the presence or absence of 250 µg/ml naphthalene before switching to PBS containing trypan blue. This solution was re-circulated through the cell chip for 30 minutes and the chip visualized under a light microscope (see Methods section). Naphthalene caused significant cell death of the rat L2 cells in the lung compartment of the cell chip while no cell death was observed in the absence of naphthalene (data not shown). No cell death was observed in the H4IIE cell compartment with or without naphthalene or in the L2 cell compartment in the absence of H4IIE cells (data not shown).

These results demonstrate that naphthalene is activated in the "liver" compartment and the toxic metabolites circulate to the "lung" and cause cell death. These results are consistent with data obtained with the benchtop CCA device and expected from the PBPK model (Sweeney, L. M., Shuler, M. L., Babish, J. G., and Ghanem, A. (1995). A cell culture analogue of rodent physiology: application of napthalene toxicology. *Toxicol. in Vitro*, 9, 307-316).

Example 9

A Human Microscale Chip Prototype

Figure 27:
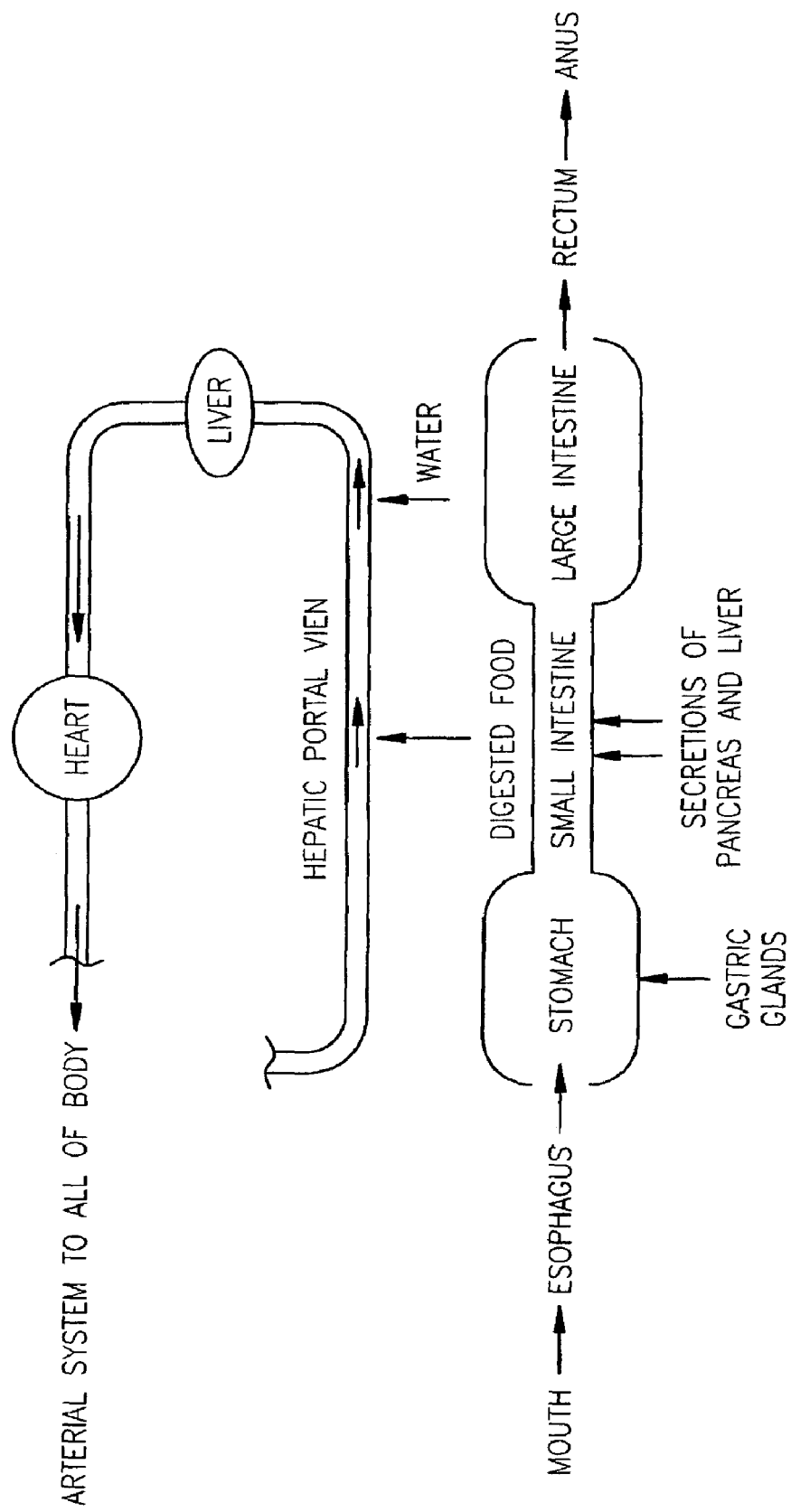
FIG. 27 depicts a human bio-chip prototype.

A human biochip prototype was prepared that contained compartments for lung, target tissues, and other tissues. The dimensions of the compartments and channels were as follows:
Inlet: 1 mm by 1 mm
Liver: 3.2 mm wide by 4 mm long
Target Tissues: 2 mm by 2 mm
Other Tissues: 340 µm wide by 110 mm long
Outlet: 1 mm by 1 mm
Channel Connecting Liver to Y connection: 440 µm wide
Channel from Y connection to Target Tissue: 100 µm wide The human biochip prototype is fabricated as described previously. The placement of the organ compartments is intended to simulate exposure to a compound (drug) that has been ingested orally. When a compound is orally ingested it is absorbed into the blood from the small or large intestine. From here it circulates directly to the liver via the hepatic portal vein then gets distributed throughout the body (FIG. 27). Therefore, with this design, the liver is the first organ compartment, followed by a split to other tissues a compartment and a chamber for the target tissue. The other tissues compartment represented distribution and hold-up of blood in the body, the target tissue compartment represents the therapeutic target of interest (e.g., colon cancer cells representing a colon tumor.

CONCLUSION

The invention provides a pharmacokinetic-based culture device and systems, usually including a first cell culture chamber having a receiving end and an exit end, and a second cell culture chamber having a receiving end and an exit end, and a conduit connecting the exit end of the first cell culture chamber to the receiving end of the second cell culture chamber. Preferably the device is chip-based, i.e., it is microscale in size. A culture medium can be circulated through the first cell culture chamber, through the conduit and through the second culture chamber. The culture medium may also be oxygenated at one or more points in the recirculation loop.

The device may include a mechanism for communicating signals from portions of the device to a position off the chip, e.g., with a waveguide to communicate signals from portions of the device to a position off the chip. Multiple waveguides can be present, e.g., a first waveguide communicating signals from the first chamber, and a second waveguide communicating signals from a second chamber, and so forth.

In one embodiment, at least one of the first cell culture chamber and the second cell culture chamber is three dimensional. In another embodiment, both the first cell culture chamber and the second cell culture chamber are three dimensional.

The device for maintaining cells in a viable state also includes a fluid circulation mechanism, may be a flow through fluid circulation mechanism or a fluid circulation mechanism that recirculates the fluid. The device for maintaining cells in a viable state also includes a fluid path that connects at least the first compartment and the second compartment. In an embodiment, a debubbler removes bubbles in the flow path. The device can further include a pumping mechanism. The pumping mechanism may be located on the substrate.

A method is provided for sizing a substrate to maintain at least two types of cells in a viable state in at least two cell chambers. The method includes the steps of determining the type of cells to be held on the substrate, and applying the constraints from a physiologically based pharmacokinetic model to determine the physical characteristics of the substrate. The step of applying the constraints from a physiologically based pharmacokinetic model includes determining the type of chamber to be formed on the substrate, which may also include determining the geometry of at least one of the cell chambers and determining the geometry of at a flow path interconnecting two cell chambers. The step of applying the constraints from a physiologically based pharmacokinetic model may also include determining the flow media composition of the flow path.

All publications and patent applications cited in this specification are herein incorporated by reference as if each individual publication or patent application were specifically and individually indicated to be incorporated by reference.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A pharmacokinetic-based microscale culture device, comprising:
a first microscale chamber containing a first type of cell, wherein the first microscale chamber is dimensioned to maintain the first type of cell under conditions that give rise to least one pharmacokinetic parameter value in vitro that is comparable to a value for the same at least one pharmacokinetic parameter obtained with respect to the same type of cell in vivo, wherein the at least one pharmacokinetic parameter comprises metabolism by cells, wherein the first microscale chamber comprises a first inlet and a first outlet for flow of culture medium, and wherein metabolism by cells is achieved by at least any one of tissue size ratio, tissue to blood volume ratio, drug residence time, flow rate, circulatory transit time, liquid residence time, and liquid to cell ratio;
a second microscale chamber containing a second type of cell, wherein the second microscale chamber is dimensioned to maintain the second type of cell under conditions that give rise to at least a second pharmacokinetic parameter value in vitro comparable to a value for the same at least a second pharmacokinetic parameter obtained with respect to the same second type of cell in vivo, wherein the second microscale chamber comprises a second inlet and a second outlet for flow of culture medium; and
a microfluidic channel interconnecting the first and second microscale chambers wherein the microfluidic channel is dimensioned to transport a culture medium, and wherein the microscale culture device is dimensioned to maintain at least one desired value for shear stress under a condition of flow of the culture medium.

2. A pharmacokinetic-based microscale culture device comprising:
a microscale chamber containing a first type of cell, wherein said microscale chamber is dimensioned to maintain the first type of cell under conditions that give rise to a value for at least one pharmacokinetic parameter in vitro that is comparable to a value for the same at least one pharmacokinetic parameter obtained with respect to the same type of cell in vivo, wherein the pharmacokinetic parameter is selected from the group consisting of liquid residence time and liquid to cell volume ratio, wherein the microscale chamber comprises a first inlet and a first outlet for flow of culture medium.

3. A pharmacokinetic-based microscale culture device comprising:
a first microscale chamber containing a first type of cell, wherein the first microscale chamber is dimensioned to maintain the first type of cell under conditions that give rise to a value for at least one pharmacokinetic parameter in vitro that is comparable to a value for the same at least one pharmacokinetic parameter obtained with respect to the same type of cell in vivo, wherein the pharmacokinetic parameter is selected from the group consisting of liquid residence time and liquid to cell volume ratio, wherein the first microscale chamber comprises a first inlet and a first outlet for flow of culture medium, and
a second microscale chamber containing a second type of cell, wherein the second microscale chamber comprises a second inlet and a second outlet for flow of culture medium; and
a microfluidic channel interconnecting the first and second microscale chambers wherein the microfluidic channel is dimensioned to transport culture medium.

4. A pharmacokinetic-based microscale culture device comprising:
a microscale chamber containing a first type of cell, wherein said chamber is dimensioned to maintain the first type of cell under conditions that give rise to a value for at least one pharmacokinetic parameter in vitro that is comparable to a value for the same at least one pharmacokinetic parameter obtained with respect to the same type of cell in vivo, wherein the pharmacokinetic parameter is metabolism by cells, wherein metabolism by cells is achieved by at least any one of tissue size ratio, tissue to blood volume ratio, drug residence time, flow rate, circulatory transit time, liquid residence time, and liquid to cell ratio, wherein the chamber comprises a first inlet and a first outlet for flow of culture medium.

5. A pharmacokinetic-based microscale culture device comprising:
a first microscale chamber containing a first type of cell, wherein the first microscale chamber is dimensioned to maintain the first type of cell under conditions that give rise to a value for at least one pharmacokinetic parameter in vitro that is comparable to a value for the same at least one pharmacokinetic parameter obtained with respect to the same type of cell in vivo, wherein the pharmacokinetic parameter is metabolism by cells, wherein metabolism by cells is achieved by at least any one of tissue size ratio, tissue to blood volume ratio, drug residence time, flow rate, circulatory transit time, liquid residence time, and liquid to cell ratio, wherein the first microscale chamber comprises a first inlet and a first outlet for flow of culture medium, and;
a second microscale chamber containing a second type of cell, wherein the second chamber comprises a second inlet and a second outlet for flow of culture medium; and
a microfluidic channel interconnecting the first and second microscale chambers wherein the microfluidic channel is dimensioned to transport culture medium.

6. The device of claim 1, 2, 3, 4, or 5, further comprising a debubbler configured to remove bubbles from fluid that flows in or through the device.

7. The device of claim 6 wherein the debubbler is located within the device.

8. The device of claim 6 wherein the debubbler is located externally to the device.

9. The device of claim 1, 2, 3, 4, or 5, wherein said first type of cell comprises a cell from heart, kidney, stomach, intestine, lung, liver, skin, fat, bone, cartilage, skeletal muscle, smooth muscle, cardiac muscle, bone marrow, muscle, brain, or pancreas.

10. The device of claim 1, 3, or 5, wherein the second type of cell comprises malignant or diseased cells.

11. The device of claim 1, 3, or 5, wherein one of the microscale chambers contains a tumor biopsy.

12. The device of claim 1, 3, or 5, wherein the first and second type of cell are selected to effect the metabolism of a drug.

13. The device of claim 1, 2, 3, 4, or 5, further comprising a sensor for obtaining signals from cultured cells.

14. The device of claim 13 wherein the sensor comprises a biosensor or a waveguide.

15. The device of claim 1, 2, 3, 4, or 5, wherein the first type of cell comprises liver cells.

16. The device of claim 1, 3, or 5, wherein at least one of the first and second type of cell is cultured on collagen or poly-lysine.

17. The device of claim 1, 3, or 5, wherein the first and second type of cells are, independently, circulating, immobilized, or adhered to the device through a biological material.

18. The device of claim 17, wherein said first type of cell and/or said second type of cell is selected from the group consisting of healthy tissue, diseased tissue, a portion of a tissue biopsy, a portion of skin, a portion of tissue, a portion of an artery, a portion of a vein, a portion of a gastrointestinal tract, a portion of an esophagus, a portion of a colon, a portion of a liver, a portion of an organ, a portion of a heart, a portion of a brain, a portion of a kidney, a portion of a lung, a portion of a muscle, a cell culture, an eukaryotic cell, a plant cell, an animal cell, a mammalian cell, a prokaryotic cell, a primary cell, a tumor cell, a stem cell, a genetically altered cell, a transformed cell, and an immortalized cell.

19. The device of claim 1, 2, 3, 4, or 5, wherein the device is further configured to provide a quantitative output.

20. The device of claim 1, 2, 3, 4, or 5, further comprising at least one additional type of cell.

21. The device of claim 1, 3, or 5, wherein the first and second type of cell are the same.

22. The device of claim 1, wherein the at least a second pharmacokinetic parameter comprises metabolism by cells.

23. The device of claim 1, 2, 3, 4, or 5, further comprising a pumping mechanism.

24. The device of claim 23, wherein the pumping mechanism is integrated in the device.

25. The device of claim 23, wherein the pumping mechanism is external to the device.

26. The device of claim 1, 3, or 5, wherein the first and/or second type of cell comprises a circulating or adherent cell.

27. The device of claim 1, 2, 3, 4, or 5, wherein said first type of cell comprises a cell from a tissue biopsy.

28. The device of claim 1, 2, 3, 4, or 5, wherein the device is microfabricated.

29. The device of claim 1, 2, 3, 4, or 5, wherein the device is manufactured from a microfabricated master.

30. The device of claim 1, 2, 3, 4, or 5, wherein the first and/or second type of cell is selected from the group consisting of a portion of healthy tissue, a portion of diseased tissue, a portion of a tissue biopsy, a portion of skin, a portion of tissue, a portion of an artery, a portion of a vein, a portion of a gastrointestinal tract, a portion of an esophagus, a portion of a colon, a portion of a liver, a portion of an organ, a portion of a heart, a portion of a brain, a portion of a kidney, a portion of a lung, a portion of a muscle, a cell culture, an eukaryotic cell, a plant cell, an animal cell, a mammalian cell, a prokaryotic cell, a primary cell, a tumor cell, a stem cell, a genetically altered cell, a transformed cell, and an immortalized cell.

31. The device of claim 1, 3, or 5, wherein the first and second microscale chambers are separated by a barrier.

32. The device of claim 31, wherein the barrier mimics a gastrointestinal barrier or a blood brain barrier.

33. The device of claim 2 or 4, wherein the device is configured for the culture medium to flow re-circulated through the microscale chamber.

34. The device of claim 2 or 4, wherein the first type of cell is cultured on collagen or poly-lysine.

35. The device of claim 2 or 4, wherein the first type of cell is circulating, immobilized, or adhered to the device through a biological material.

36. The device of claim 35, wherein said first type of cell is selected from the group consisting of healthy tissue, diseased tissue, a portion of a tissue biopsy, a portion of skin, a portion of tissue, a portion of an artery, a portion of a vein, a portion of a gastrointestinal tract, a portion of an esophagus, a portion of a colon, a portion of a liver, a portion of an organ, a portion of a heart, a portion of a brain, a portion of a kidney, a portion of a lung, a portion of a muscle, a cell culture, an eukaryotic cell, a plant cell, an animal cell, a mammalian cell, a prokaryotic cell, a primary cell, a tumor cell, a stem cell, a genetically altered cell, a transformed cell, and an immortalized cell.

37. The device of claim 2 or 4, wherein the first type of cell comprises a circulating or adherent cell.

38. A method of culturing cells in a microscale culture device to provide a pharmacokinetic parameter in vitro comparable to that found in vivo comprising:
    maintaining a first type of cell in a first microscale chamber in the microscale culture device, wherein said first microscale chamber is dimensioned to provide a value of at least one pharmacokinetic parameter in vitro that is comparable to a value for the same at least one pharmacokinetic parameter obtained with respect to the same type of cell in vivo, wherein the pharmacokinetic parameter is metabolism by cells, wherein the first microscale chamber comprises a first inlet and a first outlet for flow of culture medium, and wherein metabolism by cells is achieved by at least any one of tissue size ratio, tissue to blood volume ratio, drug residence time, flow rate, circulatory transit time, liquid residence time, and liquid to cell ratio;
    maintaining a second type of cell in a second microscale chamber, wherein said second microscale chamber is dimensioned to provide a value of at least a second pharmacokinetic parameter in vitro that is comparable to a value for the same at least a second pharmacokinetic parameter obtained with respect to the same second type of cell in vivo, wherein the second microscale chamber comprises a second inlet and a second outlet for flow of culture medium;
    and wherein the first and second microscale chambers are interconnected with a microfluidic channel wherein the microfluidic channel is dimensioned to transport the culture medium; and, wherein the microscale culture device is dimensioned to maintain at least one desired value for shear stress under a condition of flow of the culture medium, and
    culturing said first and said second types of cells in said microscale culture device to provide values for metabolism by said first type of cell comparable to in vivo values for metabolism by said first type of cell.

39. The method of claim 38, further comprising removing bubbles from fluid that flows in or through said chambers.

40. The method of claim 38 further comprising contacting the first type of cell with a material to be tested and evaluating the effect of said material.

41. The method of claim 40 wherein said evaluating is performed with a biosensor.

42. The method of claim 40 wherein said material comprises a drug, a cytotoxic substance, a potentially cytotoxic substance, a pharmaceutical composition or an inhibitory compound.

43. The method of claim 42 wherein the material comprises a drug.

44. The method of claim 43 further comprising quantitating the effect of said drug on the metabolism of said first type of cell.

45. The method of claim 38 wherein said first type of cell comprises a cell from heart, stomach, intestine, lung, liver, skin, fat, bone, cartilage, skeletal muscle, smooth muscle, cardiac muscle, bone marrow, muscle, brain, or pancreas.

46. The method of claim 45 wherein said second type of cell comprises malignant or diseased cells.

47. The method of claim 38 wherein said first type of cell comprises liver cells.

48. The method of claim 38 further comprising re-circulating the culture medium.

49. The method of claim 38 wherein the first microscale chamber contains at least one additional type of cell.

50. A method of culturing cells to provide a pharmacokinetic parameter in vitro comparable to that found in vivo comprising:
  maintaining a first type of cell in a first microscale chamber, wherein said first microscale chamber is dimensioned to provide a value of at least one pharmacokinetic parameter in vitro that is comparable to a value for the same at least one pharmacokinetic parameter found for the same type of cell in vivo, wherein the at least one pharmacokinetic parameter is selected from the group consisting of liquid residence time and liquid-to-cell volume ratio, and wherein the first microscale chamber comprises a first inlet and a first outlet for flow of fluid;
  maintaining a second type of cell in a second microscale chamber dimensioned to maintain said second type of cell under conditions that provide a value of at least a second pharmacokinetic parameter in vitro that is comparable to a value of the at least a second pharmacokinetic parameter with respect to said second type of cell in vivo and the second microscale chamber comprises a second inlet and a second outlet for flow of fluid;
  flowing fluid through said first and second microscale chambers through at least one microfluidic interconnecting channel; and
  culturing said first and said second types of cells in said microscale chambers.

51. A method of culturing cells to provide a pharmacokinetic parameter in vitro comparable to that found in vivo comprising:
  maintaining a first type of cell in a first microscale chamber, wherein said chamber is dimensioned to provide a value of at least one pharmacokinetic parameter in vitro that is comparable to a value for the same at least one pharmacokinetic parameter found for the same type of cell in vivo, wherein the at least one pharmacokinetic parameter is metabolism by cells, wherein metabolism by cells is achieved by at least any one of tissue size ratio, tissue to blood volume ratio, drug residence time, flow rate, circulatory transit time, liquid residence time, and liquid to cell ratio, wherein the first microscale chamber comprises a first inlet and a first outlet for flow of fluid, and;
  maintaining a second type of cell in a second microscale chamber dimensioned to maintain said second type of cell under conditions that provide a value of at least a second pharmacokinetic parameter in vitro that is comparable to a value for the same at least a second pharmacokinetic parameter with respect to the second type of cell in vivo and the second microscale chamber comprises a second inlet and a second outlet for flow of fluid;
  flowing fluid through said first and second microscale chambers through at least one microfluidic interconnecting channel; and
  culturing said first type of cell and said second type of cell in said microscale chambers.

52. The method of claim 50 or 51 further comprising contacting the first type of cell with a material to be tested and evaluating the effect of said material.

53. The method of claims 50 or 51 wherein said first type of cell and said second type of cell are selected from at least one of the group consisting of healthy tissue, diseased tissue, a portion of a tissue biopsy, a portion of skin, a portion of tissue, a portion of an artery, a portion of a vein, a portion of a gastrointestinal tract, a portion of an esophagus, a portion of a colon, a portion of a liver, a portion of an organ, a portion of a heart, a portion of a brain, a portion of a kidney, a portion of a lung, a portion of a muscle, a cell culture, an eukaryotic cell, a plant cell, an animal cell, a mammalian cell, a prokaryotic cell, a primary cell, a tumor cell, a stem cell, a genetically altered cell, a transformed cell, and an immortalized cell.

54. The method of claims 50 or 51 wherein the characteristics of the fluid flow are based on a mathematical model.

55. The method of claim 54 wherein the mathematical model is a physiologically-based pharmacokinetic ("PBPK") model.

56. A method comprising:
  forming a first microscale chamber in a device, wherein the first microscale chamber is dimensioned to maintain cells under conditions that provide a value of at least one pharmacokinetic parameter in vitro that is comparable to a value for the same at least one pharmacokinetic parameter found in vivo, wherein the at least one pharmacokinetic parameter comprises metabolism by cells, wherein metabolism by cells is achieved by at least any one of tissue size ratio, tissue to blood volume ratio, drug residence time, flow rate, circulatory transit time, liquid residence time, and liquid to cell ratio;
  forming a second microscale chamber that is dimensioned to maintain cells under conditions that provide a value of at least a second pharmacokinetic parameter in vitro that is comparable to a value for the at least a second pharmacokinetic parameter found in vivo, wherein the at least a second pharmacokinetic parameter comprises metabolism by cells, wherein metabolism by cells is achieved by at least any one of tissue size ratio, tissue to blood volume ratio, drug residence time, flow rate, circulatory transit time, liquid residence time, and liquid to cell ratio;
  adding, forming, or providing at least one microfluidic interconnecting channel in fluid communication with the first and second microscale chambers, wherein said at least one channel is configured to provide fluid flow through said first and second microscale chambers.

57. The method of claim 56 further comprising adding a debubbler that is configured to remove bubbles from fluid that flows in, through, or in proximity to the microscale chambers.

58. The method of claim 57 wherein the debubbler is located within the device.

59. The method of claim 57 wherein the debubbler is located externally to the device.

60. The method of claim 57 wherein adding, forming or providing for the debubbler further comprises forming, containing, assembling, making, constituting, or inserting the debubbler in or into the device.

61. The method of claim 57 wherein the debubbler is located within a portion of the at least one microfluidic channel.

62. A method of culturing cells to provide a pharmacokinetic parameter in vitro comparable to that found in vivo comprising:
- maintaining a first type of cell in a device comprising a first microscale chamber, wherein said first microscale chamber is dimensioned to provide a value of at least one pharmacokinetic parameter in vitro that is comparable to a value for the same at least one pharmacokinetic parameter found for the same type of cell in vivo, wherein the pharmacokinetic parameter is selected from the group consisting of liquid residence time and liquid to cell volume ratio, wherein the first microscale chamber comprises a first inlet and a first outlet for flow of culture medium; and
- culturing said first type of cell in said first microscale chamber.

63. The method of claim 62, wherein said device further comprises
- a second microscale chamber containing a second type of cell, wherein the second microscale chamber comprises a second inlet and a second outlet for flow of culture medium; and
- a microfluidic channel interconnecting the first and second microscale chambers wherein the microfluidic channel is dimensioned to transport culture medium.

64. A method of culturing cells to provide a pharmacokinetic parameter in vitro comparable to that found in vivo comprising:
- maintaining a first type of cell in a device comprising a first microscale chamber, wherein said first microscale chamber is dimensioned to provide a value of at least one pharmacokinetic parameter in vitro that is comparable to a value for the same at least one pharmacokinetic parameter found for the same type of cell in vivo, wherein the pharmacokinetic parameter is metabolism by cells, wherein metabolism by cells is achieved by at least any one of tissue size ratio, tissue to blood volume ratio, drug residence time, flow rate, circulatory transit time, liquid residence time, and liquid to cell ratio, wherein the first microscale chamber comprises a first inlet and a first outlet for flow of culture medium; and
- culturing said first type of cell in said first microscale chamber.

65. The method of claim 64, wherein said device further comprises
- a second microscale chamber containing a second type of cell, wherein the second chamber comprises a second inlet and a second outlet for flow of culture medium; and
- a microfluidic channel interconnecting the first and second microscale chambers wherein the microfluidic channel is dimensioned to transport culture medium.

* * * * *